United States Patent
Housley et al.

(10) Patent No.: US 11,213,671 B2
(45) Date of Patent: Jan. 4, 2022

(54) ELECTROPORATION SYSTEM FOR CONTROLLED LOCALIZED THERAPEUTICS DELIVERY

(71) Applicant: NewSouth Innovations Pty Limited, Sydney (AU)

(72) Inventors: Gary David Housley, Connells Point (AU); Nigel Hamilton Lovell, Coogee (AU); Jeremy Pinyon, Waverton (AU); Edward Norman Crawford, Mortdale (AU); Cherylea Browne, Marrickville (AU)

(73) Assignee: NewSouth Innovations Pty Limited, Sydney (AU)

( * ) Notice: Subject to any disclaimer, the term of this patent is extended or adjusted under 35 U.S.C. 154(b) by 355 days.

(21) Appl. No.: 15/738,443

(22) PCT Filed: Jun. 24, 2016

(86) PCT No.: PCT/AU2016/050546
§ 371 (c)(1),
(2) Date: Dec. 20, 2017

(87) PCT Pub. No.: WO2016/205865
PCT Pub. Date: Dec. 29, 2016

(65) Prior Publication Data
US 2018/0169399 A1    Jun. 21, 2018

(30) Foreign Application Priority Data

Jun. 25, 2015   (AU) ............................... 2015902456

(51) Int. Cl.
*A61N 1/04* (2006.01)
*A61N 1/08* (2006.01)
(Continued)

(52) U.S. Cl.
CPC ............ *A61N 1/0412* (2013.01); *A61B 18/00* (2013.01); *A61B 34/10* (2016.02); *A61N 1/0529* (2013.01);
(Continued)

(58) Field of Classification Search
CPC combination set(s) only.
See application file for complete search history.

(56) References Cited

U.S. PATENT DOCUMENTS

2005/0052630 A1    3/2005  Smith et al.
2008/0045880 A1*   2/2008  Kjeken .................. A61N 1/327
                                                    604/21
(Continued)

FOREIGN PATENT DOCUMENTS

WO    02/100459 A2    12/2002
WO    2011006204      1/2011
WO    2014201511      12/2014

OTHER PUBLICATIONS

CUY21EDIT,https://www.sonidel.com/product_info.php?_id=32 (Year: 2008).*

(Continued)

*Primary Examiner* — Lauren P Farrar
*Assistant Examiner* — Hamza A Darb
(74) *Attorney, Agent, or Firm* — Michael Best & Friedrich LLP

(57) ABSTRACT

Embodiments of the present invention provide an electroporation system comprising an electroporation probe having at least two contiguous electrodes configured to be inserted into biological tissue for electroporation treatment, and a pulse generator electrically connected to the probe and configured to drive the electroporation probe using a sequence of one or more electric pulses to cause current transmission through the probe and induce a non-uniform (Continued)

electric field in the biological tissue proximate the probe electrodes. Treatment tissue can be targeted by controlling the probe configuration, carrier solution characteristics and parameters of the electroporation pulse sequence to achieve predictable electroporation outcomes. This electroporation control method can also reduce potentially toxic effects of electroporation treatment.

20 Claims, 35 Drawing Sheets

(51) Int. Cl.
    *A61N 1/05*         (2006.01)
    *A61N 1/32*         (2006.01)
    *A61B 34/10*        (2016.01)
    *A61B 18/00*        (2006.01)

(52) U.S. Cl.
    CPC ......... *A61N 1/0541* (2013.01); *A61N 1/0575* (2013.01); *A61N 1/08* (2013.01); *A61N 1/327* (2013.01); *A61B 2018/00071* (2013.01); *A61B 2018/00154* (2013.01); *A61B 2018/00767* (2013.01); *A61N 1/0424* (2013.01)

(56) References Cited

U.S. PATENT DOCUMENTS

| | | |
|---|---|---|
| 2011/0106221 A1 | 5/2011 | Neal, II et al. |
| 2012/0089009 A1* | 4/2012 | Omary .................. A61N 1/327 600/411 |
| 2016/0129246 A1* | 5/2016 | Housley ................ A61N 1/327 604/20 |

OTHER PUBLICATIONS

International Search Report for Application No. PCT/AU2016/050546 dated Oct. 4, 2016 (4 pages).
International Preliminary Report on Patentability for Application No. PCT/AU2016/050546 dated Oct. 12, 2017 (23 pages).
Pinyon, J.L. et al., "Close-field electroporation gene delivery using the cochlear implant electrode array enhances the bionic ear," Science Translational Medicine, Apr. 23, 2014, vol. 6, Issue 233, pp. 1-10.
CUY21EDIT In Vivo Square Wave Electroporator [retrieved from internet on Sep. 23, 2016] <URL: http://www.sonidel.com/product_info.php?products_id=32> published on Apr. 20, 2008 as per Wayback Machine.
Search Report issued from the European Patent Office for related Application No. 16813403.9 dated May 8, 2018 (8 pages).

* cited by examiner

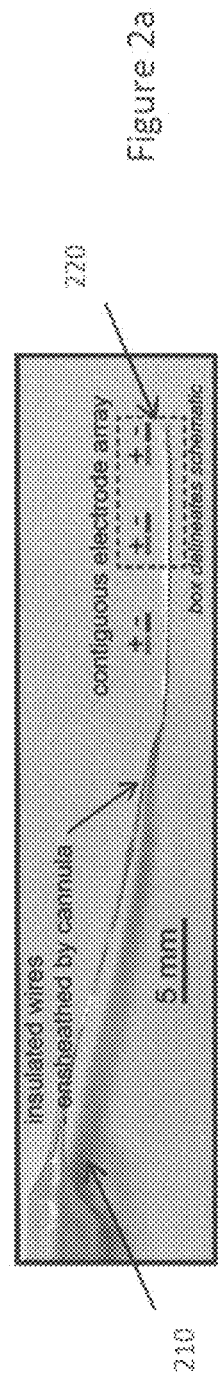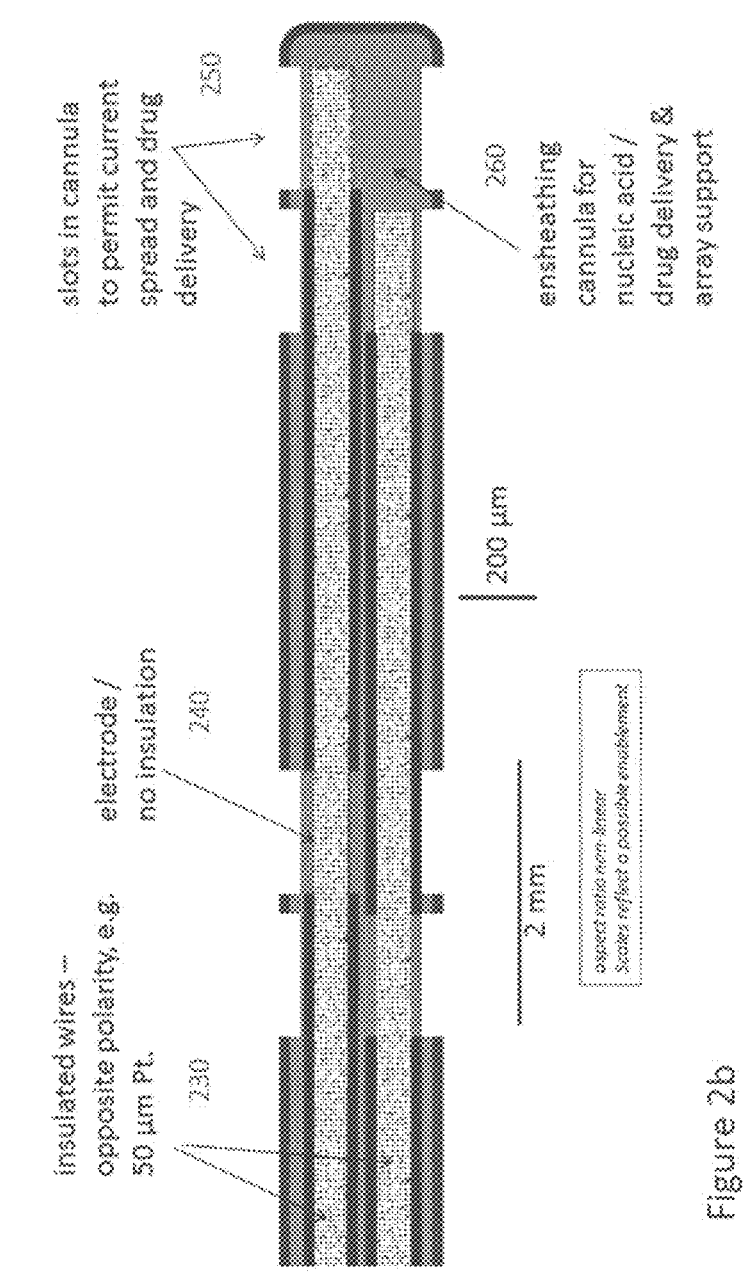

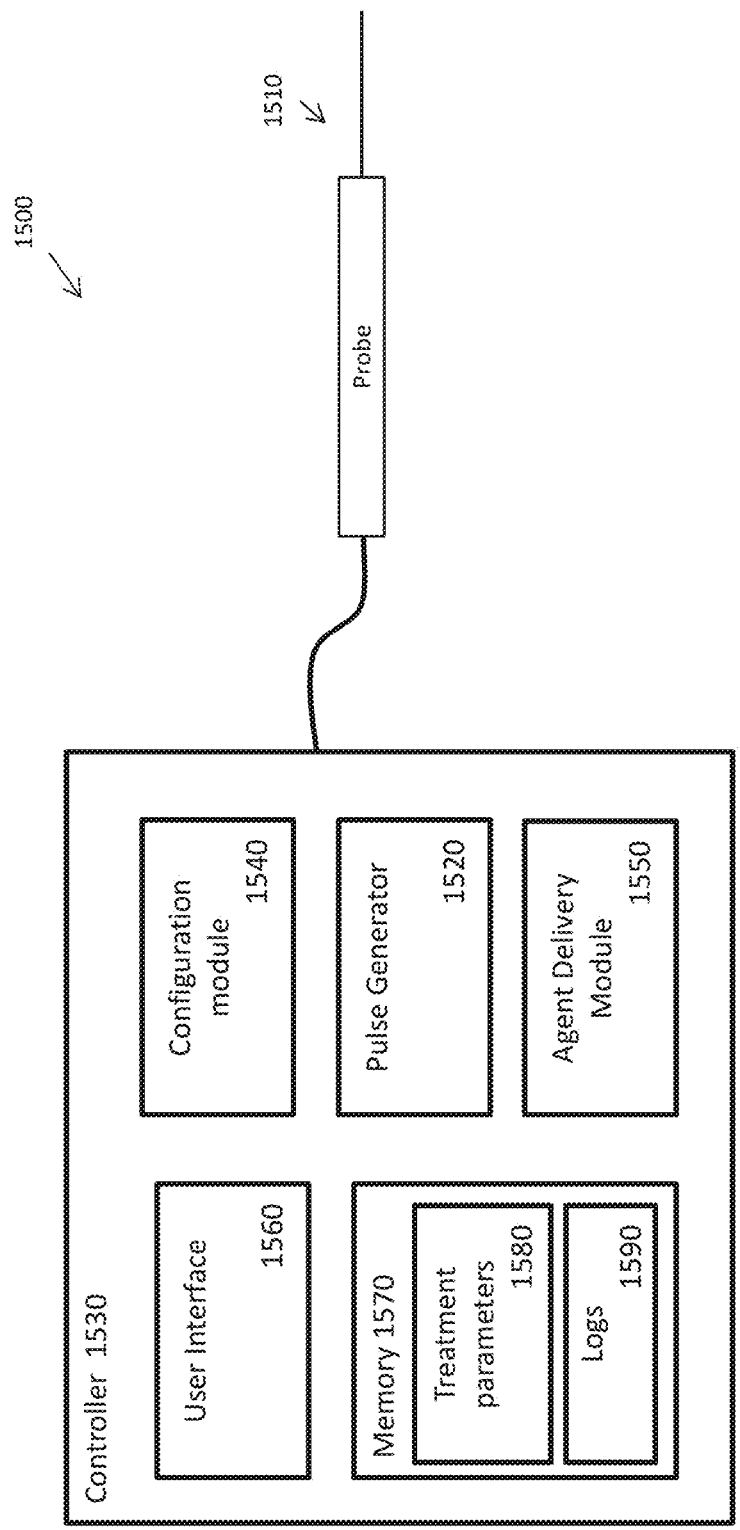

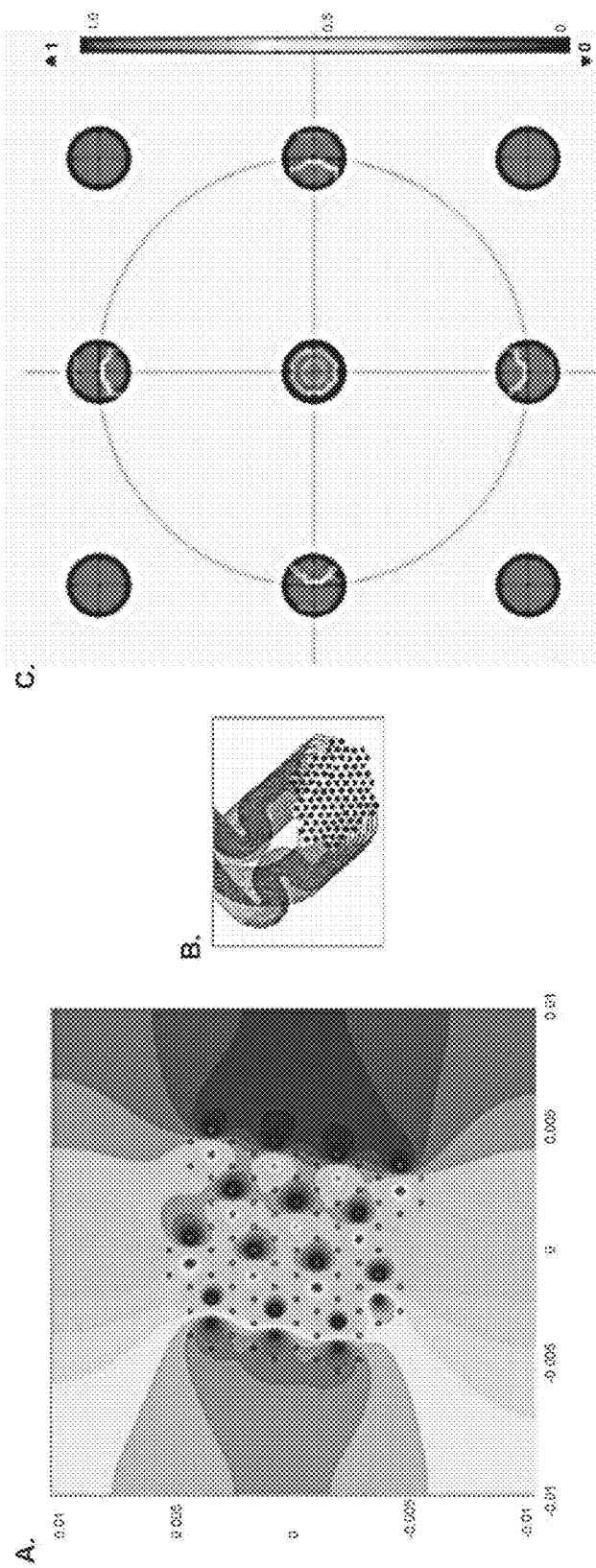

Figure 16

Model of electric fields arising from array-based electric field focusing for gene electrotransfer utilising central electrodes in an hexagonal array (770 μm electrode pitch), with a simple return electrode (A). Fabrication layout (B). C. Electric field potentials on the surface of nine cells modelled as 10 μm diameter spheres distributed above one of the electrodes in the hexagonal array.

ELECTROPORATION SYSTEM FOR CONTROLLED LOCALIZED THERAPEUTICS DELIVERY

TECHNICAL FIELD

The present invention relates to a system for controlled therapeutic molecule delivery to targeted groups of cells within tissues using electroporation. Examples of applications of the system are for delivery of DNA, therapeutic molecules or other agents into cells using electroporation where the electrodes are integrated within an array that is inserted into the tissue and cells targeted for electroporation are adjacent to, rather than between the electrodes.

BACKGROUND TO THE INVENTION

Electroporation is a technique used in molecular biology where an electrical field is applied to cells in order to increase the permeability of the cell membrane, thereby allowing chemicals, drugs, or DNA to be introduced into the cell. The underlying principle is that an electric field generated by a high voltage pulse between two electrodes causes a transient dielectric breakdown of the plasma membrane of cells within the high intensity electric field, enabling DNA or other molecules to enter the cells.

Conventional electroporation uses electric fields between physically separated electrodes resulting in a direct current path through tissue between the electrodes. An electroporation technique described by the inventors in previous international patent applications numbers WO2011/006204 and WO2014/201511 provides for electroporation using an electric field that is asymmetric in relation to an array of electrodes driven, such that local current paths between elements of the electrode array generate electric fields which vary from positive to negative potentials in the vicinity of the array, and produce transient electroporation of cells in the neighbourhood of the array.

This electroporation technique was described by the Inventor and his team in the paper "Pinyon J L, Tadros S F, Froud K E, Wong A C Y, Tompson I T, Crawford E N, Ko M, Morris R, Klugmann M, Housley G D (2014) Close-field electroporation gene delivery using the cochlear implant electrode array enhances the bionic ear. Science Translational Medicine 6, 233ra54. DOI. 10.1126/scitranslmed.3008177. (publ. 23 Apr. 2014) in this paper the term "close-field electroporation" (CFE) was coined as a label for the technique. The technique was also described in detail in International patent application publication no WO2014/201511 the disclosure of which is incorporated herein by reference, in its entirety. In the course of this work, the inventors discovered that utilising an electric field adjacent the electrode array could achieve transfection of cells in the vicinity of the array using lower cumulative charge than required to achieve transfection of the same number of cells using open field electroporation where target cells or tissue are placed in a direct current path between electrodes. Further, it was discovered that the efficiency of cell electroporation varies relative to the position of the electrodes within the field.

SUMMARY OF THE INVENTION

According to a first aspect there is provided an electroporation system comprising: an electroporation probe comprising at least two contiguous electrodes configured to be temporarily inserted into biological tissue for electroporation treatment; and a pulse generator electrically connected to the probe and configured to drive the electroporation probe using a sequence of one or more electric pulses to cause current transmission through the probe and induce a non-uniform electric field in the biological tissue proximate the probe electrodes.

In an embodiment, the non-uniform electric field includes electric field gradients in the range of 50 $\mu V/\mu m$ to 1500 $\mu V/\mu m$.

In an embodiment, the electrodes are relatively elongate along the direction of contiguity, wherein the electrode circumference is less than the electrode length. An embodiment of the probe comprises at least one pair of contiguous electrodes, each electrode having a length of 1 mm or less. An embodiment of the probe comprises a linear electrode array. Alternative embodiments of the probe include two or three dimensional arrays of electrodes.

An embodiment of the electroporation system further comprises a controller configured to allow selective control of the pulse generator to control the sequence of pulses delivered via the probe. In an embodiment the controller is further configured to allow a selection of electrodes to be driven. Embodiments of the controller can be configured to measure properties of the tissue surrounding the array.

In an embodiment the controller is configured to control electrical pulse parameters for the sequence of pulses based on carrier solution characteristics. The controller can be configured to calculate the electrical pulse parameters based on a target electric potential gradient in the induced non-uniform electric field. In an embodiment electrical pulse parameters are controlled for current regulated pulse delivery. In this embodiment current amplitude for use with saccharose-based carrier solution is determined based on saccharose type and concentration. In another embodiment electrical pulse parameters are controlled for voltage regulated pulse delivery. In this embodiment voltage amplitude for use with saccharose-based carrier solution is determined based on saccharose type and concentration.

In an embodiment the probe includes electrical recording capability to aid placement and timing of gene electrotransfer such as resistance measurements and electrophysiology measurements.

In an embodiment the controller is configured to measure operating characteristic for a treatment environment with the probe inserted in the treatment environment. The controller can be further configured to predict induced field voltage during pulse delivery based on the measured operating characteristics. The controller can be configured to determine electrical pulse parameters for pulse delivery based on the measured operating characteristics. In an embodiment the controller is configured to trigger electrical pulse delivery based on the measured operating characteristics.

Embodiments of the electroporation probe further comprise at least one therapeutic agent delivery structure. In some probe embodiments, the therapeutic agent delivery structure includes a fluid delivery structure. For example, the fluid delivery structure can include any one or more of: integrated fluid chambers, microfluidics pathways, and a cannula.

In some alternative embodiments the therapeutic agent delivery structure includes a material carrying the therapeutic agent for delivery. For example, the therapeutic agent can be any one or more of: embedded within the material, coating the material or encapsulated within the material. In some embodiments the material allows uncontrolled release of the therapeutic agent into the biological tissue.

In some embodiments the system further comprises a therapeutic delivery controller configured to control delivery of the therapeutic agent to the biological tissue. In an embodiment the therapeutic delivery controller is configured to control delivery of the therapeutic agent based on the sequence of electrical pulses.

An electroporation probe comprising at least two contiguous electrodes configured to be temporarily inserted into biological tissue for electroporation treatment and connectable to a pulse generator, the electrodes configured to induce a non-uniform electric field in the biological tissue proximate the probe electrodes when driven using a sequence of one or more electric pulses causing current transmission through the probe.

In an embodiment, each electrode has a length of 1 mm or less and an electrode circumference less than the electrode length.

An embodiment of the probe includes two parallel insulated wires with at least one pair of contiguous electrodes provided by adjacent uninsulated regions of each wire. In an embodiment the probe comprises a cannula for therapeutic agent delivery and the wires are provided within the cannula. The cannula can be perforated in the region of the electrodes to allow therapeutic agent delivery in the region of the electrodes.

According to another aspect there is provided an electroporation system controller comprising a system processor and memory, the controller being configured to determine a sequence of one or more electric pulses and electrical pulse parameters for the pulse sequence to, when applied to an electroporation probe, induce a non-uniform electric field in biological tissue proximate the probe electrodes for an electroporation treatment.

The electrical pulse parameters for the sequence of pulses can be determined based on carrier solution characteristics. The controller can be configured to calculate the electrical pulse parameters based on a target electric potential gradient for the induced non-uniform electric field.

The electrical pulse parameters can be determined for current regulated pulse delivery. In this instance current amplitude for use with saccharose-based carrier solution is determined based on saccharose type and concentration. Alternatively the electrical pulse parameters can be determined for voltage regulated pulse delivery. In this instance voltage amplitude for use with saccharose-based carrier solution is determined based on saccharose type and concentration.

The controller can be further configured to measure operating characteristic for a treatment environment with a connected probe inserted in the treatment environment. In this embodiment the controller can be further configured to predict induced field voltage during pulse delivery based on the measured operating characteristics. The controller can be configured to determine electrical pulse parameters for pulse delivery based on the measured operating characteristics. The controller can be configured to trigger electrical pulse delivery based on the measured operating characteristics.

In an embodiment the controller is further configured to model electroporation treatment outcomes for one or more sequences of pulses and electrical pulse parameters based on electroporation probe configuration, target treatment area and carrier solution.

BRIEF DESCRIPTION OF THE DRAWINGS

An embodiment, incorporating all aspects of the invention, will now be described by way of example only with reference to the accompanying drawings in which:

FIG. 2 shows a prototype probe in accordance with an embodiment of the invention, FIG. 15 shows a block diagram of a system embodiment, FIG. 16 shows an example of a two dimensional array and modelled electrical field.

DETAILED DESCRIPTION

Figure 1:
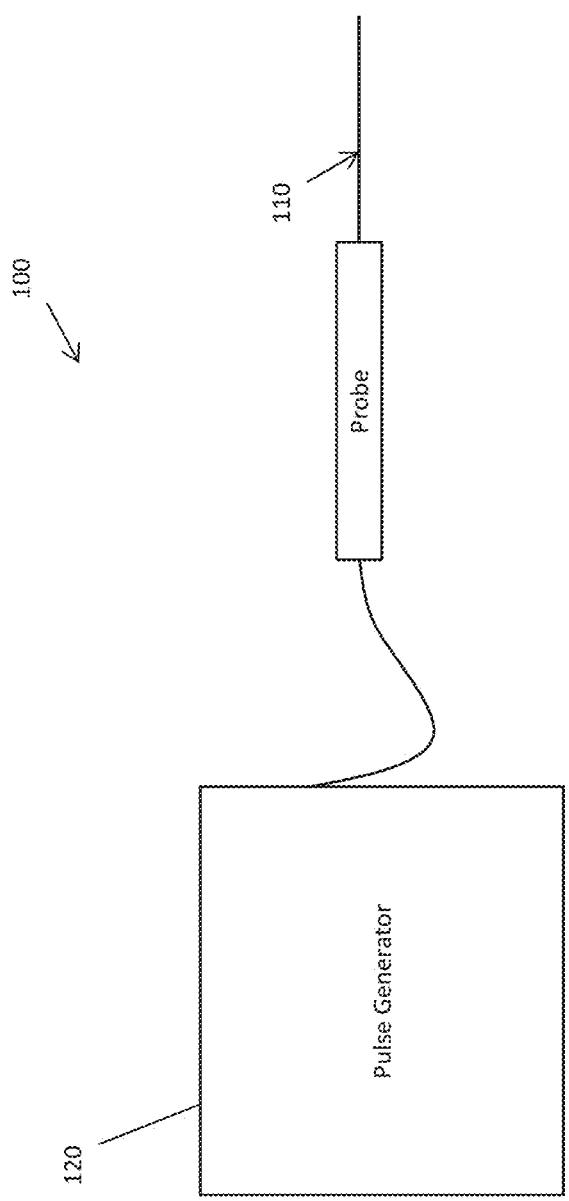
FIG. 1 is an exemplary block diagram of an electroporation system in accordance with an embodiment of the invention.

Embodiments of the present invention provide an electroporation system for acute use. An embodiment of the invention, as shown in FIG. 1, provides an electroporation system 100 comprising an electroporation probe 110 having at least two contiguous electrodes configured to be temporarily inserted into biological tissue for electroporation treatment, and a pulse generator 120 electrically connected to the probe and configured to drive the electroporation probe using a sequence of one or more electric pulses to cause current transmission through the probe and induce a non-uniform electric field in the biological tissue proximate the probe electrodes.

In related work of the inventors, they previously described 'close-field electroporation' (CFE) of cells for delivery of DNA and other molecules (Pinyon et al. Science Translational Medicine, April, 2014). CFE can be achieved by passing current locally between electrodes which are physically contiguous, so that the electric fields radiate out from the array to expose cells to the field, rather than passing current between electrodes where the target cells are placed between the electrodes and hence within the direct current path. The latter can be described as "open-field electroporation". In the Pinyon et al. study, an array of electrodes, embodied as a cochlear implant bionic prosthesis, was used for delivery of DNA to the cochlea. This was undertaken in vitro—where DNA was injected into the scala tympani fluid space of the cochlea and then the cochlear implant was inserted into that space and a few electrical impulses were applied to the array, resulting in the electroporation-based gene delivery to mesenchymal cells adjacent to the array. The cochlear implant was then removed and the tissue placed into tissue culture for several days. The transduced cells were then imaged based on green fluorescence protein (GFP) reporter expression, which was driven by a naked (plasmid) DNA gene cassette. CFE gene delivery was then demonstrated in vivo using the same procedure—acute insertion of the array for gene delivery—and then with chronic implantation of the array—where the gene delivery was undertaken at the time of implantation and then the array was left in the cochlea for subsequent used for conventional electrical stimulation of the auditory nerve.

In the course of this work, the inventors discovered that close field electroporation could achieve transfection of cells proximate the array using lower cumulative charge than required to achieve transfection of the same number of cells using open field electroporation. Further, the inventors discovered that the efficiency of cell electroporation varied relative to the position of the electrodes within the field. Further to these discoveries, the inventors have identified improved transfection in regions of non-uniformity of the electric field compared with regions where the electric field is uniform. The inventors have also discovered that characteristics of the carrier solution for the therapeutic agent can also affect the efficiency of cell electroporation. Utilising these discoveries the inventors have developed techniques for controlling characteristics of the electroporation electric field to thereby enable predictable cell transfection outcomes in targeted tissue regions. The systems and methods developed by the inventors utilise the variables, including any one or more of: array configuration, stimulation pulse pattern characteristics, and carrier solution characteristics, to control the electric field characteristics for an electroporation treatment process.

Electric Field Control for Electroporation

Figure 4B:
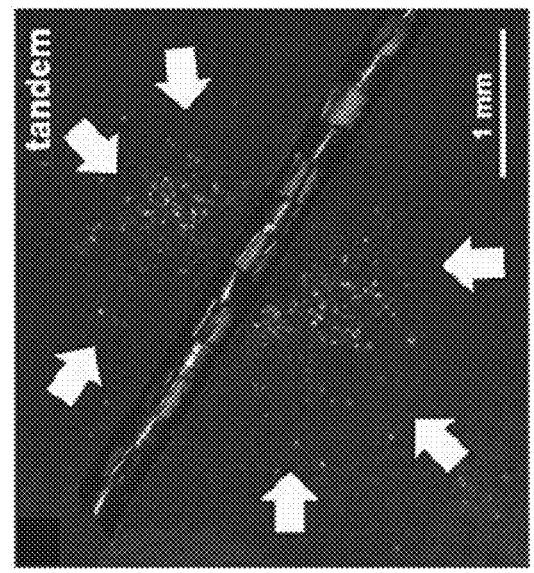
FIGS. 4a-4c show a mapped electric field and cell transformation results using a tandem array configuration.
Figure 4C:
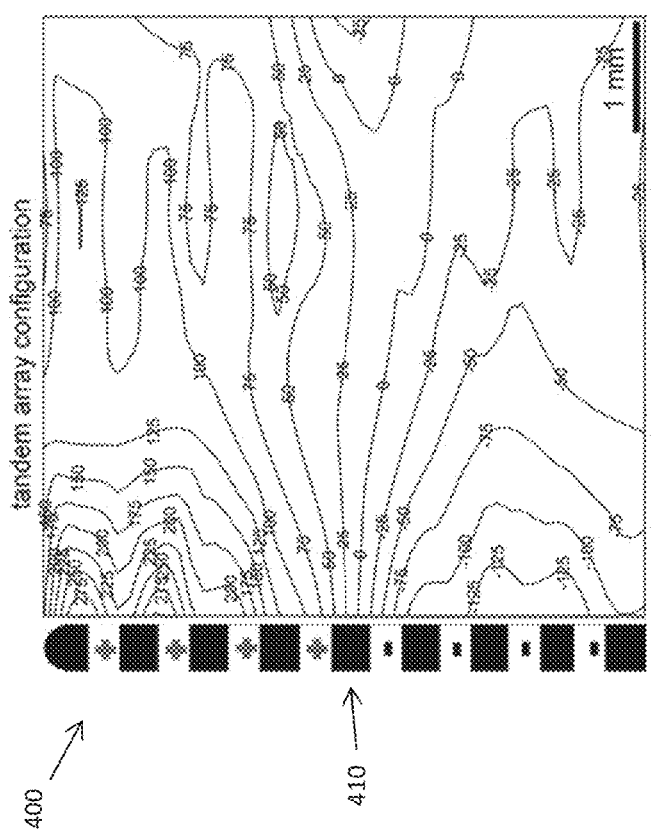
Figure 4A:
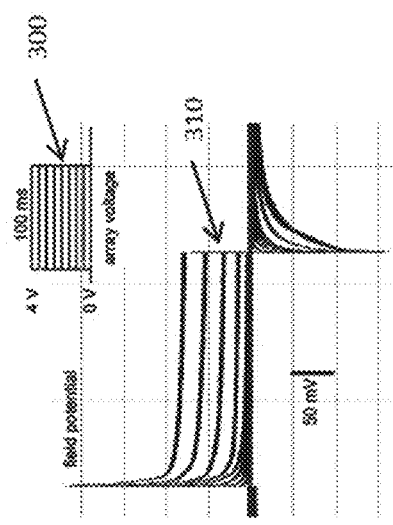
Figure 5B:
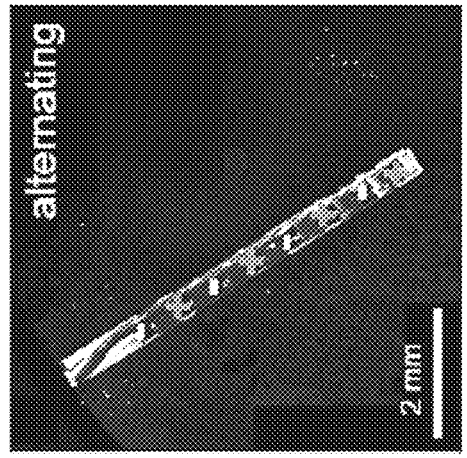
FIGS. 5a-5c show a mapped electric field and cell transformation results using an alternating array configuration.
Figure 5C:
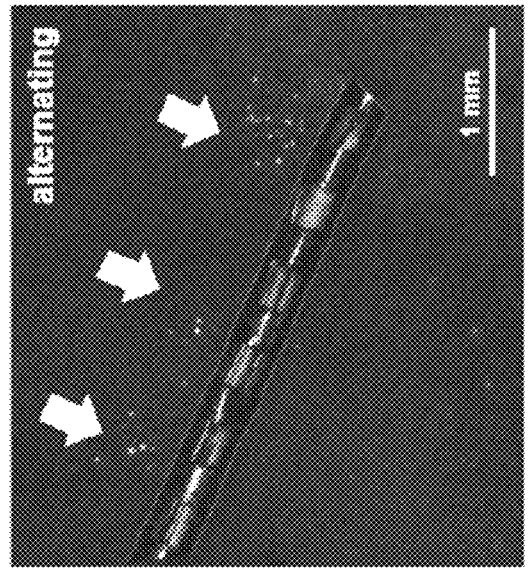
Figure 5A:
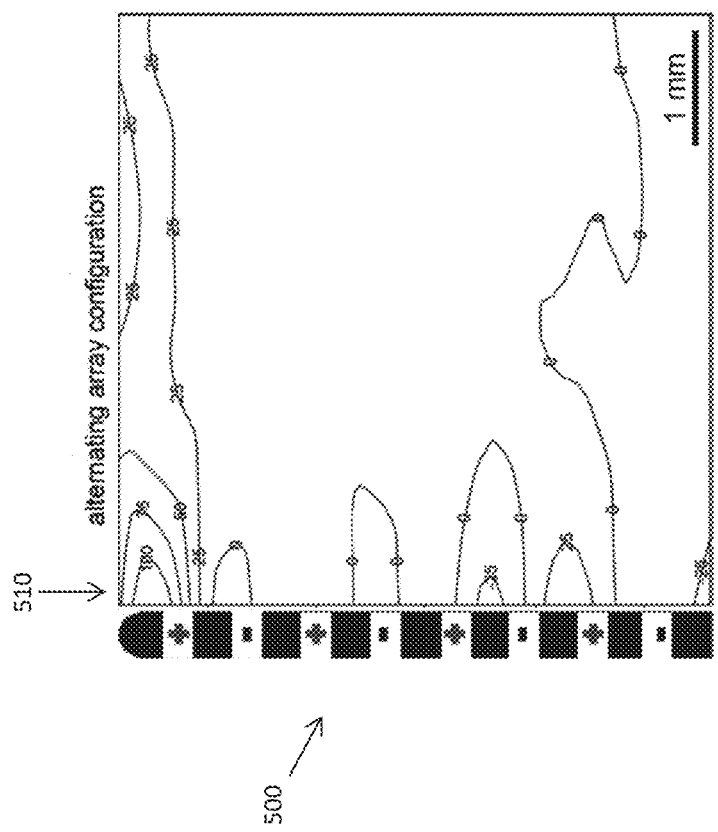
Figure 6B:
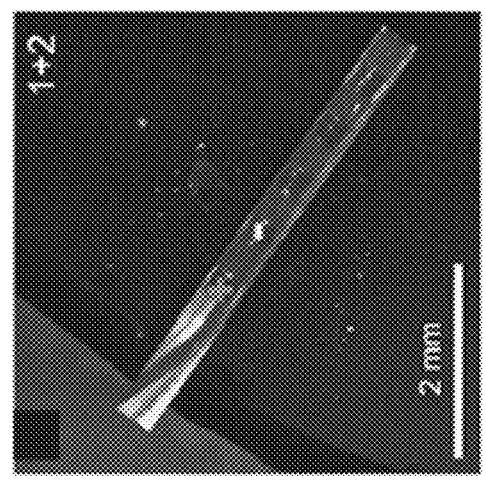
FIGS. 6a-6b show a mapped electric field and cell transformation results using a 1+2 array configuration.
Figure 6A:
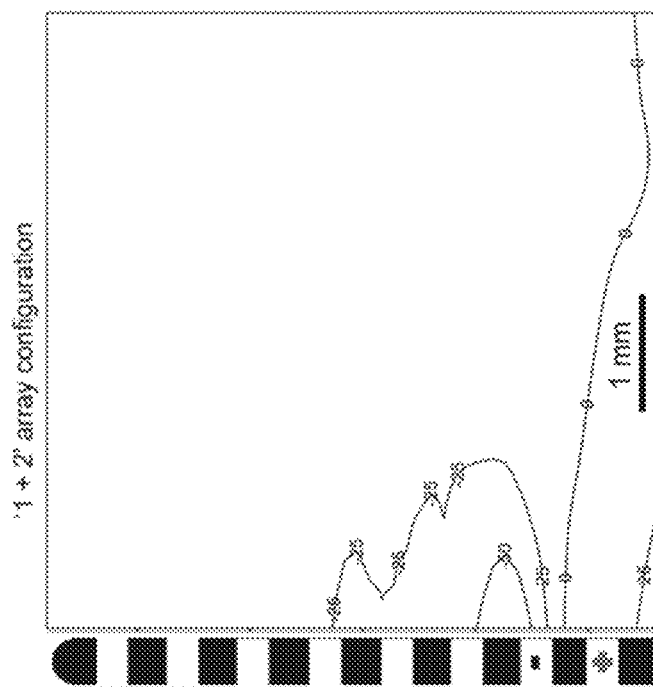
Figure 7B:
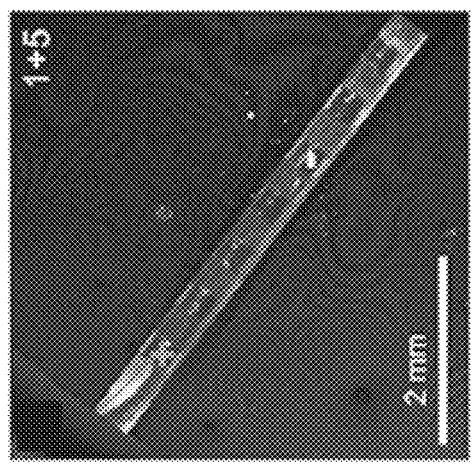
FIGS. 7a-7b show a mapped electric field and cell transformation results using a 1+5 array configuration.
Figure 7A:
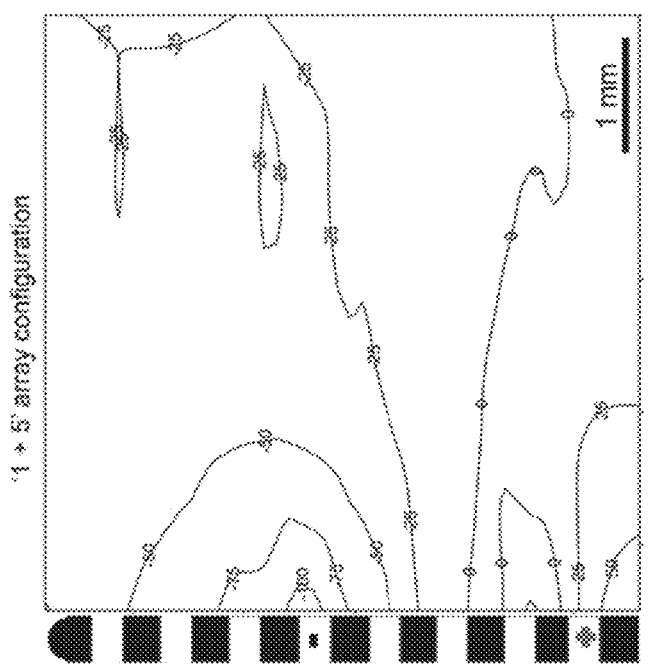
Figure 8B:
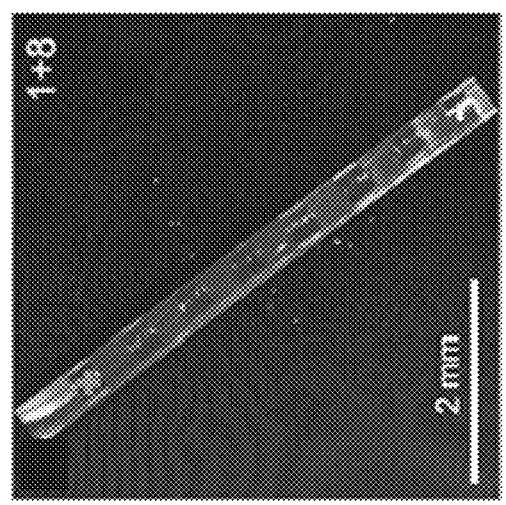
FIGS. 8a-8b show a mapped electric field and cell transformation results using a 1+8 array configuration.
Figure 8A:
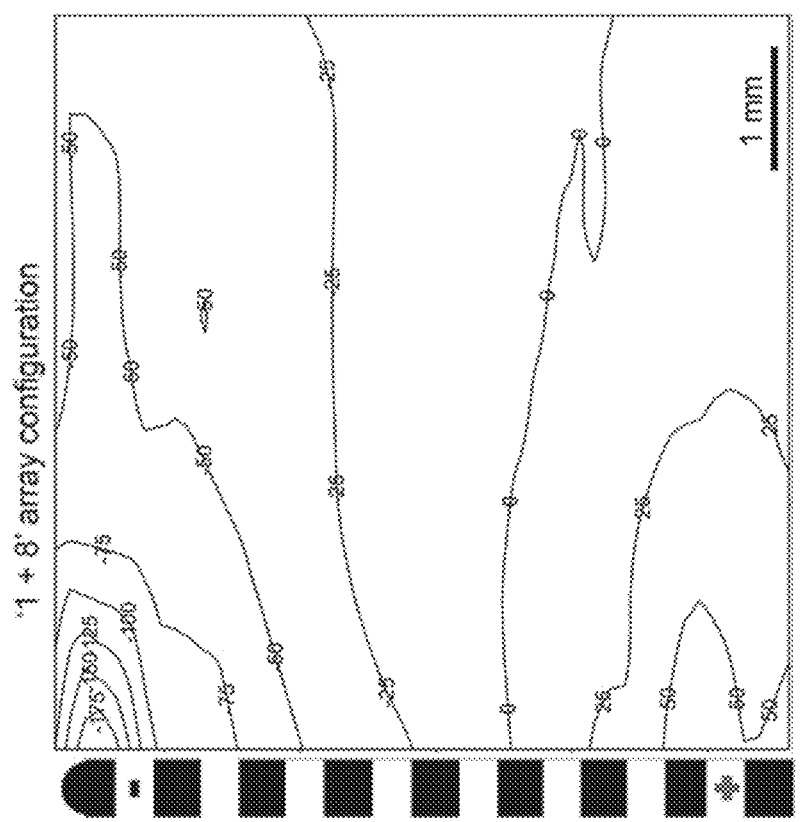

The electroporation technique of the present invention targets cells adjacent the array of electrodes, where the electric field is shaped around the array by the combination of current sources (anodes) and current returns (cathodes). FIGS. 4a, 5a, 6a, 7a and 8a show examples of mapped electric field potentials resulting from different anode and cathode configurations for an eight electrode array and FIGS. 4b, 4c, 5b, 5c, 6b, 7b and 8b show resulting distributions of cell transformations after electroporation for each array configuration. The 8 electrodes within the array were configured as anodes and cathodes in the following combinations:

Tandem—four juxtaposed cathodes then four juxtaposed anodes, all elements with 300 µm separation, total length 5 mm (illustrated in FIGS. 4a-c);

Alternating—alternating cathodes and anodes within 300 µm separation, total length 5 mm (illustrated in FIGS. 5a-c);

1+2—a single anode and a single cathode within 300 μm separation (illustrated in FIGS. 6*a-b*);

1+5—a single anode and a single cathode with 2.45 mm separation (illustrated in FIGS. 7*a-b*); and 1+8—a single anode and a single cathode with 4.55 mm separation (illustrated in FIGS. 8*a-b*).

FIGS. 4*b*, 5*b*, 6*b*, 7*b* and 8*b*, show for comparison the effect of the array configuration on electroporation-mediated gene delivery, with all array configurations driven using a pulse sequence having the parameter set: 40V, 10 pulses, 50 ms duration, and 1 pulse/sec. Although all array configurations produced significant cell transductions, there was a significant effect on transformation efficiency due to array configuration, with variation in the space between anode and cathode, and in the number and pattern of anodes and cathodes. The 1+2 array driving configuration resulted in a spherical field of cells ~1 mm diameter, with the active electrodes at the centre (FIG. 6*b*). The alternating array driving configuration produced a linear bias to the field of transfected cells, extending the length of the array (~5 mm; 81.8±11.3 GFP-positive cells) as shown in FIGS. 5*b* and 5*c*. The 1+5 and 1+8 array driving configurations yielded smaller average numbers of transformed cells, which had a low-density distribution (FIGS. 7*b* & 8*b*). The transfection efficiency of the tandem configuration was significantly higher than any other configuration (FIGS. 4*b* and 4*c*) and the pattern was spherical in shape centred around the midpoint of the array, which was the confluence point between the four anodes and four cathodes. Testing by the inventors showed that the charge delivery required to achieve efficient cell transduction was least when the array was configured for anodes and cathodes ganged together as bipoles ('tandem' configuration).

Figure 3:
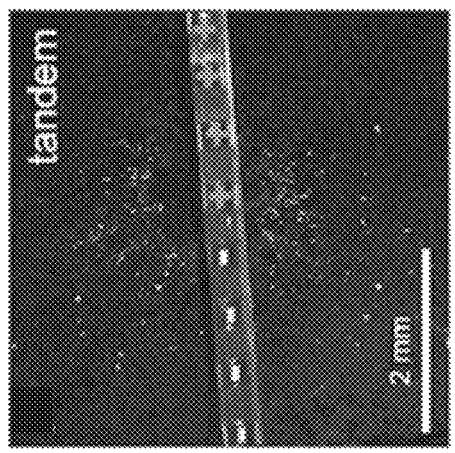
FIG. 3 shows a pulse and traces of field potentials recorded using a tandem array configuration.

FIGS. 4*a*, 5*a*, 6*a*, 7*a* and 8*a*, show, for comparison, the electric field mapped for each array configuration, the field potential were measured at the end of a 100 ms 4V pulse 300 applied to the array, shown in FIG. 3. FIG. 3 also shows traces 310 of field potentials recorded with 0.5 v steps up to 4V (100 ms duration) using the tandem array configuration. The 'tandem' configuration permitted significantly greater transduction efficiency compared with the equivalent number of electrodes wired in 'alternating' configuration. This study also demonstrated that smaller bipolar electrode configurations were less efficient (1+2, 1+5, 1+8). The reason that the 'tandem' array configuration shows unanticipated efficiency of cell transduction is attributed to the geometry of electric field focusing (FIG. 4*a*). The tandem array 400 exhibited the highest electric field contour density, with the null position tracking from the junction between the anodes and cathodes 410 (FIG. 4*a*). In contrast, despite utilising an equivalent number of electrodes, the alternating array configuration 500 had lower electric field density gradients, distributed along the array with the peak at the end of the array 510 (FIG. 5*a*). Given the spherical GFP positive field of cells centred around the null point of the 'tandem' array (FIGS. 4*b* and 4*c*; orthogonal to the point 410 between electrodes 4 & 5 in FIG. 4*a*), the data indicate that it is the electric field across the cell, rather than the absolute step change in electric potential, that drives electroporation and DNA uptake. The cell distributions for the other array configurations showed similar association with the measured electric field, and the drop off in number of GFP positive cells in the 1+2>1+5>1+8 was correlated with the broadening in the electric field relative to the electrodes.

The electric fields around the arrays were closely correlated with the spatial mapping of transformed cells. Thus, the cell transduction was dependent upon the electric potential gradient across the cell, rather than the absolute voltage. This is most evident with the contour map for the tandem configuration using 0.9% saline solution, where the null region in the field migrates orthogonally to the array between electrodes 4 and 5 (FIG. 4*a*). The field contour lines are steepest about this line and are maintained in a spherical shape which corresponds to the transduced cell maps. The magnitudes of the electric potential measurements are greatest at either end of the tandem array, but more uniform. As the distance separating the bipolar electrodes increased the field density declined, as evidenced by comparing results for the 1+2, 1+5 and 1+8 arrays in FIGS. 6*b*, 7*b*, and 8*b* respectively.

Figure 10:
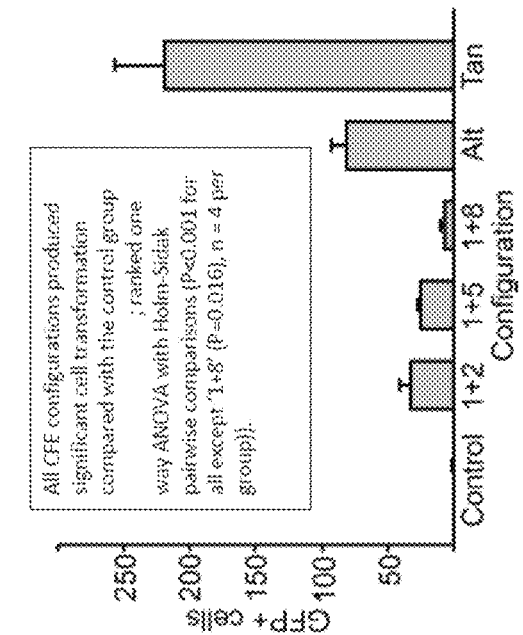
FIG. 10 shows a comparison of cell transformations of FIG. 9.
Figure 9:
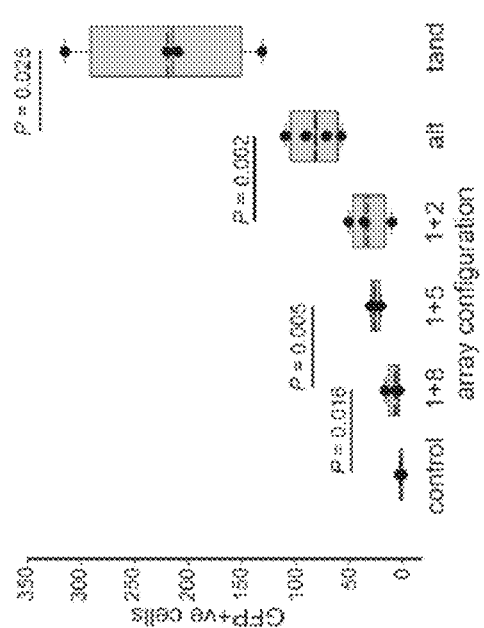
FIG. 9 shows a statistical comparison of nuclear-localised GFP fluorescence, which indicates cell transformed adjacent the array, for each array configuration.

Comparative results for each array configuration were also statistically analysed. FIG. 9 shows a statistical comparison of nuclear-localised GFP fluorescence, which indicates cells transformed by electroporation, for each array configuration from the examples of the transduction field for the different electrode array configurations (indicated). The box plots show median (line), mean (dashed line), 25% and 75% boundaries overlayed with the data (n=4 per group) of cells transformed. FIG. 10 shows a comparison of cell transformations of FIG. 9. All array driving configurations produced significant cell transformations compared with the control group, with the lowest number of transformation from the 1+8 configuration.

Figure 12:
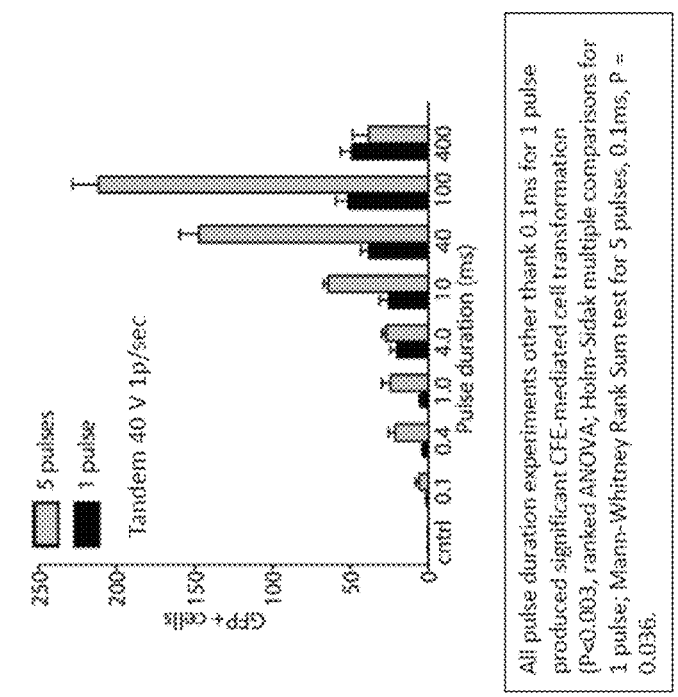
FIG. 12 shows comparative results for pulse duration and number of pulses for the tandem array configuration.
Figure 11:
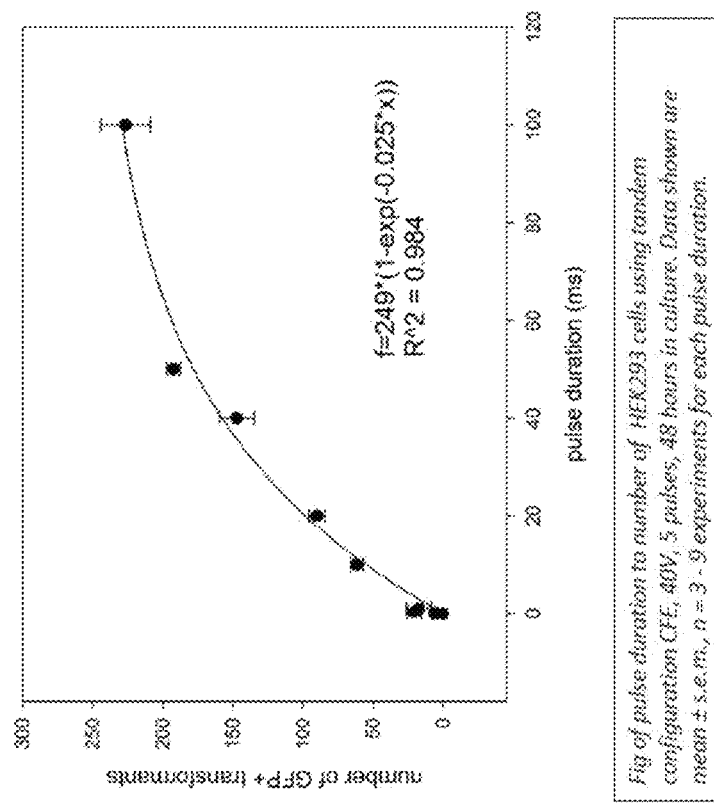
FIG. 11 shows the relationship between pulse duration and number of transformed cells using the tandem array configuration.

FIG. 11 shows the relationship between pulse duration and number of transformed cells using the tandem array driving configuration, 40V, 5 pulses, 48 hours in culture. FIG. 12 shows comparative results for pulse duration and number of pulses for the tandem array configuration. All pulse duration experiments other than 0.1 ms for 1 pulse produced significant electroporation-mediated cell transformation ($P<0.004$; ranked ANOVA; Holm-Sidak multiple comparisons for 1 pulse; 237 Mann-Whitney Rank Sum Test for 5 pulses, 0.1 ms; $P=0.026$; n=6 per group). Cell transduction was maximum at 100 ms pulse duration. Five pulses produced significantly greater transduction than 1 pulse (2 way ranked ANOVA, 10 ms-400 ms indicating a significant interaction between pulse number and pulse duration; $P<0.001$). With a single pulse, there was no difference between 40 ms (38.3±5.1 cells), 100 ms (51.7±7.8 cells; n=6) and 400 ms (49.2±6.9 cells; n=6) ($P>0.05$; Holm-Sidak multiple comparisons), whereas with the 5 pulse treatment, 40 ms (147.2±12.4 cells) and 100 ms (211.7±16.6 cells) pulse durations produced significantly greater cell transformation than the other durations ($P=0.003$; $P<0.001$ respectively). The 400 ms pulse duration with 5 pulses resulted in a 5.5 fold decline from maximum (38.3±10.2 cells; n=6 per group) ($P<0.001$; ranked 2 way ANOVA, Holm-Sidak multiple comparisons). It is believed that this is due to electrolytic toxicity (discussed further below). Test by the inventors indicated that separation of pulses between 50 ms and 1 s for two×40 ms pulses, or five×40 ms pulses, had no effect on the level of cell transduction.

These results demonstrate that pulse duration is a key determinant of the cell transduction process, with an optimum around 100 ms. Direct measurement of electric potentials within the field with increasing voltage steps shows some initial decay from peak due to the faradaic capacity of the platinum electrodes (FIG. 3). At voltages>2 V, sustained electric potentials/field develop, approaching steady state by ~100 ms. This is compatible with the concept that a sustained voltage gradient across the cells is required for efficient micro domain electroporation. The electric fields recorded by the inventors (illustrated in FIGS. 4*a*, 5*a*, 6*a*, 7*a*, and 8*a*) provide a relative representation of the fields which were generated, as the isolated voltage sensor used for electric field measurement in these experiments was unsuitable for recording at the applied voltages associated with DNA uptake (gene electrotransfer). However, above 2.5 V the electric potential measurements in the field (close to the second anode) increased linearly with increasing voltage, and at 4 V the maximum sustained potentials approached ~±250 mV immediately adjacent to the distal ends of the anode and cathode in the 'tandem' configuration. Extrapolating to a 20 V pulse, which is efficient for gene delivery, the immediate voltage sampled at this location in the field is likely to approach±2250 mV. In the 'tandem' array, the effective diameter of the field of GFP positive cells was ~50% of the array (2.5 mm), which indicates that the electric field would be ~1125 mV/2.5 mm=4.5 V/cm. Hence at a cellular level, the effective pancellular field gradients are ~450 µV/µm. It should be appreciated that the induced electric field is non-uniform, thus cannot be simply measured, for example in V/cm or for us uV/um etc. The inventors therefore sampled voltages or potentials in the field which have been represented using contour graphs, and from these graphs it is clear that the estimates of field strength depend upon location relative to the array.

Figures 13, 14:
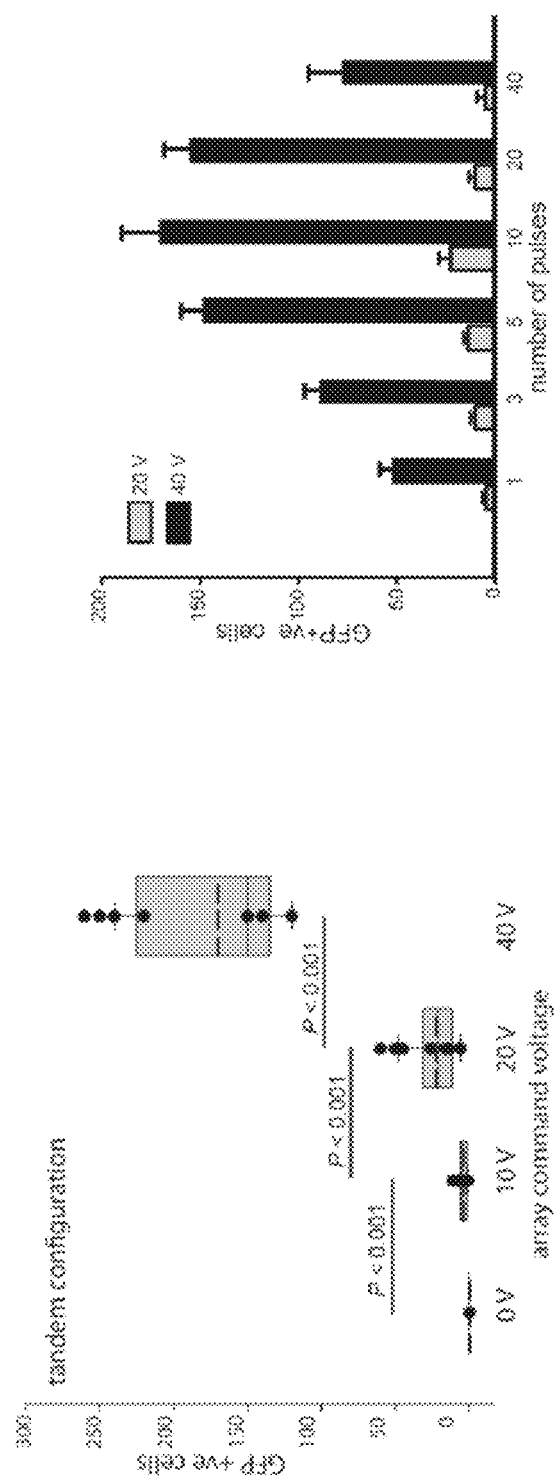
FIG. 13 shows the effect of voltage amplitude on cell transformation with tandem electrode configuration electroporation.
FIG. 14 shows the effect of pulse number on transduction efficiency with tandem electrode configuration electroporation.

The inventors have also shown that numbers of transformed cells increased significantly with increasing pulse amplitude. FIG. 13 shows the effect of voltage amplitude on cell transformation with tandem electrode driving configuration electroporation. Electroporation was delivered using 10 pulses at 40 ms duration, a pulse rate of 1/s, with varying voltage. The 40 V amplitude produced more than 40 times greater transformation than the 10 V amplitude (196.7±18.5 versus 5.9±1.1 for 10 V and 32.3±6.3 for 20 V; n=9 per group). No transformed cells were detected in the six control experiments (GFP plasmid, no electroporation). The perimeters of the fields of GFP-positive HEK293 cells were determined for the 40 V group to estimate density (29±2 cells/mm$^2$, n=6). The overall density of HEK293 cells was established using DAPI fluorescence (5097±333 cells/mm$^2$). Hence transduction efficiency was approximately 0.6%, which reflects a fall-off towards the perimeter. As is evidenced from the results in FIG. 13 around 10 V is required to reliably achieve cell transfection, with increasing voltage increasing the number of transfected cells.

FIG. 14 shows the effect of pulse number on transduction efficiency with tandem electrode configuration. Electroporation was delivered using 20V and 40V pulses with 40 ms duration and varying the number of pulses. The graph shows the average number of transfected cells per experiment. At 40V all pulse numbers (1, 3, 5, 10, 20, 40) resulted in significantly greater transduction than the control (no electroporation); ranked ANOVA, multiple comparisons versus control group (Holm-Sidak method; P<0.001 above 1 pulse; P=0.031 1 pulse; n=6 per group, except for the 5 pulses group (n=9)), with 5, 10 and 20 pulses providing the maxima (range 147-170 cells) with no significant difference between these treatments (ANOVA, Holm-Sidak comparisons). At 20V, sets of 3, 5, 10 and 20 pulses resulted in significantly greater transduction than the control (no electroporation); ranked ANOVA, multiple comparisons versus control group (Holm-Sidak method; P<0.003; n=6 per group). The peak number of GFP-positive cells averaged 22 for 10 pulses. There was a decline in transfected cell numbers at 40 pulses for both 20 V and 40 V. In addition, the inventors observed propidium iodide fluorescence close to the electrode array position, which is a marker of cell permeability and cell toxicity. This finding suggests that the roll-off in cell transformation is probably attributable to electrolytic and mechanical disruption of the cell monolayer associated with gassing, which was evident as fine bubbles on the surface of the electrodes after the electroporation sequence. On this basis, higher charge deliveries were not undertaken.

The inventors have shown in FIGS. 9 to 14 that the number of transfected cells can be controlled by array configuration, voltage, and pulse parameters. The study by the inventors has shown that the charge delivery required to achieve efficient cell transduction was least when the array was configured for anodes and cathodes ganged together as bipoles ('tandem' configuration). The 'tandem' configuration permitted significantly greater transduction efficiency compared with the equivalent number of electrodes wired in 'alternating' configuration. The study also demonstrated that smaller bipolar electrode configurations were less efficient (1+2, 1+5, 1+8). The reason that the 'tandem' array configuration shows unanticipated efficiency of cell transduction is attributed to the geometry of electric field focusing. The 'tandem' array showed the highest electric field adjacent to the electrodes compared with the other configurations. Given the spherical GFP positive field of cells centred around the null point of the 'tandem' array, orthogonal to the point between electrodes 4 & 5, this indicates that it is the electric field (gradient in voltage) across the cell, rather than the absolute step change in electric potential that drives electroporation and DNA uptake. Configuring the electrode array to produce a predictable electric field can therefore enable targeting of a specific region of cells within a tissue for electroporation treatment. Controlling the electrical parameters of the electroporation stimulation signal can then be utilised to influence the number of cells transfected in the targeted region. Thus the inventors have developed a method and system enabling predictable control (referred to as "dial up" control) of electroporation treatment outcomes and demonstrated enablement for gene electrotransfer.

It should be appreciated that for electroporation treatment of live patients the electrical stimulation parameters (i.e. voltage and current) applied may need to be limited to avoid harmful treatment side effects. Further, the "safe" parameters for the electrical stimulation may vary between patients, for example based on any one or more of type of tissue being treated, region of the body, age of patient (i.e. elderly or infants), health of the patient, potential interference with other treatments, surgical equipment or implants (i.e. pacemakers) etc.

Electroporation is still considered problematic for therapeutic gene delivery due to the low efficiency, trauma from placement of electrodes into tissues, and the typically high voltages that are required to enable DNA uptake. This can be perceived as a noxious stimulus, affecting the target organs and tissues, and may also impact on DNA stability. Study of the electroporation process at the single cell level has revealed that the transfection efficiency follows a different relationship to the electroporation efficiency with regard to the electric fields. For example, a study using suspended Chinese hamster ovary (CHO) cells demonstrated that field strengths of 200 V/cm were sufficient for electroporation, but 400 V/cm was required for transfection based on expression of a reporter transgene. A study of DNA uptake into skeletal muscle showed benefit from a combination of short duration (100 µs) "high voltage gradient" (800 V/cm) and longer duration (100 ms) "low voltage gradient" (8 V/cm) pulses to respectively permeablize and electrophoresis the DNA across the plasma membrane. Studies using fluorescently labelled DNA indicate that while the cells are permeabilized on both sides across the electric field, the (TOTO-1-labelled) plasmid-DNA only entered the cells on the cathode side. The permeabilization of the cell membrane occurs in the short time domain of the voltage pulses (typically in the μs-ms range), while recovery of cell integrity occurs over minutes. This is consistent with the propidium iodide fluorescence imaging of the inventor's testing, which was performed 30 minutes after electroporation and indicated that membrane integrity was restored in the transduced cells. Pulse amplitude affects the rate at which the cell membrane becomes permeable and the area of the membrane that is electroporated; pulse duration and pulse number affect the degree of permeabilization. The permeabilization process depends upon the electric field causing charge redistribution on the cell membrane that occurs faster than the capacitance time constant of the cell. Thus cell geometry is crucial, with mammalian cells requiring lower voltages than the smaller bacterial cells. In any case, it has been suggested that the applied voltages need to cause transmembrane potentials of ~200 mV or more for electroporation gene delivery. To achieve such a transient change in transmembrane potential, typically high field strengths are required in the macro domain for cell suspensions and tissue transfection (e.g. ~1.2 kV/cm, equivalent to 480 V with a 4 mm electrode gap). The inventor's data using saline carrier solution indicate that the field potentials required for electroporation and gene delivery can be achieved using applied voltages ~100 times less with array-based micro domain electroporation (close field electroporation), than those required for macro domain electroporation (open field electroporation). This is consistent with the reduction in applied voltages reported for electrotransfer of DNA in chick embryo neurodevelopment studies with very closely apposed electrode pairs (1 mm exposure, 4 mm separation, 3-5×50 ms pulses at 25 V); approximating a micro domain 1+5 array configuration. The inventor's field potential measurements show that the electric field compression, and hence electrotransfer, increases as the anode and cathode separation is minimized within the bionic array.

Clinical measures that utilize implantable bionic prostheses such as cochlear implants and deep brain stimulators are by their nature amenable to the incorporation of complementary gene therapy via 'close-field' electroporation. The inventors have also devised acute treatment probes, control systems and methodologies to deliver controlled and/or customised electroporation treatment. This has potential to provide a much safer and more targeted genetic enhancement than can currently be provided by other approaches, such as viral vectors or lipofection. In some embodiments the electrode array—based gene delivery can be via adaptation of existing bionic neural prosthesis. It is also envisaged that custom electrode arrays may be developed to extend the control of the shape and extent of the transduced field of cells.

The key parameters for controlling outcomes of electroporation are pulse intensity (voltage), pulse duration, pulse number, inter-pulse interval, physical array configuration, polarity of the electrodes in the array, the carrier solution composition and DNA concentration. Controlling these parameters enables control of the electric field and thereby enables control of the region and density of the electroporation outcome, for example for gene delivery to a target region of cells proximate the electrode (also referred to as "dial-up" control). Embodiments of the invention practically apply these parameters to provide an electroporation system configured to induce controlled non-uniform electric fields for electroporation, and particularly producing electric field gradients orthogonal to the electrode array. Controlling the electric field geometry enables cells within specific regions relative to the array to be targeted for treatment. The key influence on field geometry is the array configuration. Controlling the electroporation pulse parameters (i.e. intensity, pulse width, inter-pulse interval and number of pulses) controls the number of cells transfected in the targeted region, where carrier solution composition and DNA concentration were also found to affect the electric field geometry.

With regard to potential tissue damage, in the study performed by the inventors the highest charge deliveries resulted in electrolytic action and significant physical disruption to the HEK293 cell monolayer due to gassing. This is a result of the Faradaic current limits of the platinum electrodes, which was estimated as a minimum effective charge delivery of ~25 $mC/cm^2$, in saline carrier, where the μpseudocapacity of the platinum electrodes for reversible charge delivery is ~210 $\mu C/cm^2$. Thus even with inert electrodes such as platinum, possible electrochemical damage to cells may be a factor when relatively long pulse durations, high voltages and long pulse trains are utilized, with potential changes in pH arising from production of $H^+$ at the anode and $O_2$ or $Cl_2$ gas, and OH production at the cathode from reduction of water. Tissue (Joule) heating may also be associated with electroporation and both raise cell temperature and potentially destabilise DNA. Translation of bionic array-based gene therapy applications would need to be achieved below charge delivery levels that could damage cells in the neighbourhood of the electrode array. As have been demonstrated above, by configuring the electroporation array geometry to generate electric field gradients in a target region can enable effective electroporation outcomes using lower charge deliveries than known methods. A combination of array configuration and delivery pulse pattern can be calculated for a required treatment and the improved efficiency available can reduce risks of potential tissue damage.

Figure 27:
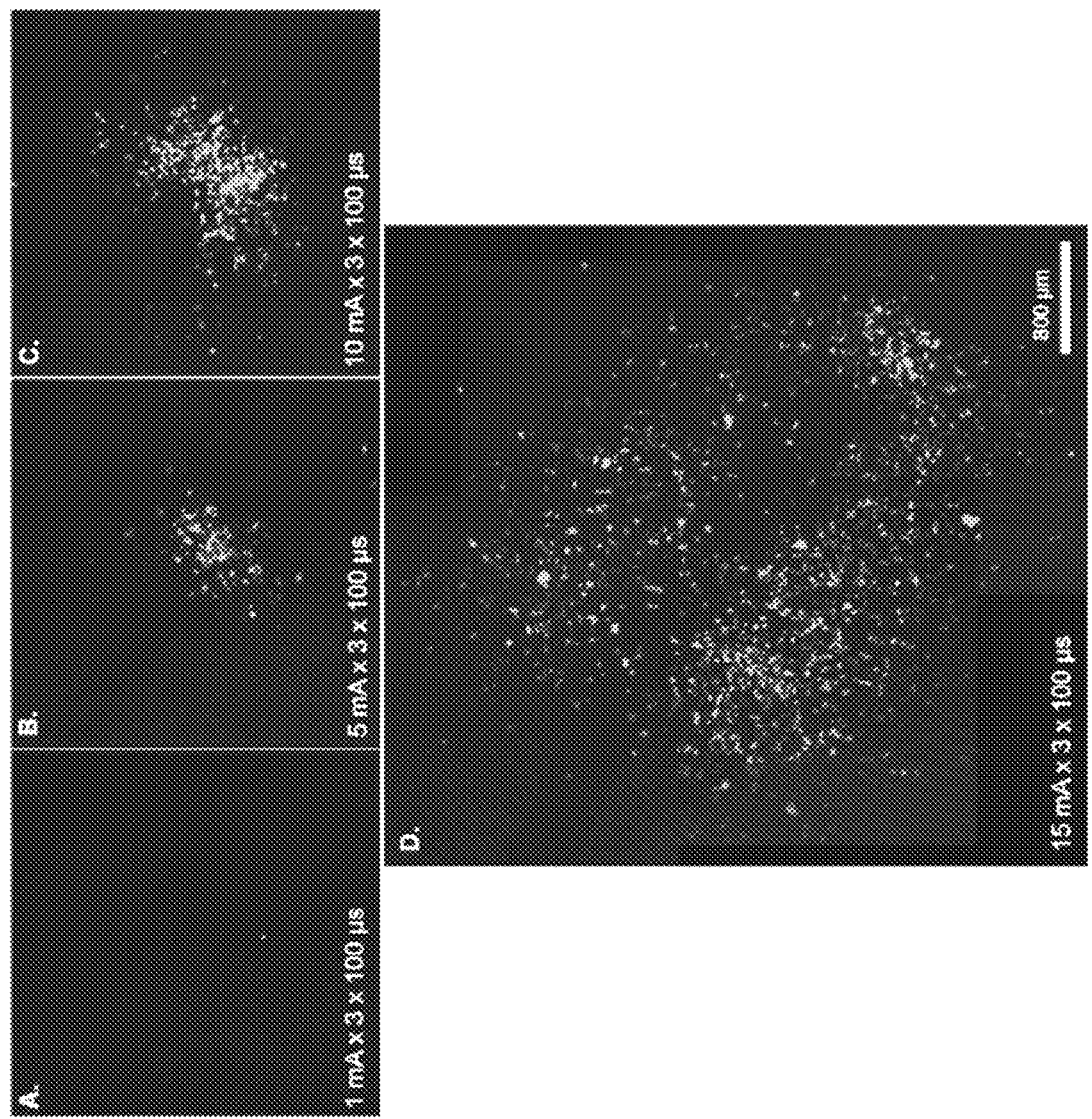
FIG. 27 is a set of photographs A-D showing Fluorescence images of GFP expression by HEK293 cells.

The inventors have also shown that characteristics of the carrier solution for the therapeutic agent, as well as the properties of DNA, can also influence the generated electric field characteristics and efficiency of electroporation outcomes. In particular the inventors have shown that the use of saccharose carrier solutions can provide increased resistance and alterations to electric field geometry in proximity to the array, and therefore electric field intensity close to the array compared with physiological saline-based solutions. Thus, the carrier solution is another parameter that may be treated as a variable when determining controlling parameters for tailoring electroporation treatment. The inventors have established that use of saccharose carrier solutions with DNA enable a reduction in the minimum effective charge for gene electrotransfer by $10^3$ (~25 $\mu C/cm^2$, in which case gassing at the electrodes was not visible), evident in the example using 100 μs pulses at 15 mA (FIG. 27).

The carrier solution composition can particularly influence the electric field intensity generated via regulated current delivery of electroporation stimulation pulses to the array, and therefore affect the electroporation and gene electro-transfer into cells. The choice of carrier solution can also influence electroporation outcomes under voltage regulated conditions.

Cell electroporation and gene electrotransfer is typically undertaken using voltage pulses of controlled amplitude (constant voltage power supply). In embodiments of the present invention, a sucrose solution was used as the carrier for DNA to achieve close-field gene electrotransfer into cells via a constant current source. The sucrose solution was found to enable a significant reduction in current required to generate an electric field (voltage) external to the electrode array of sufficient amplitude and duration to achieve improved efficiency electroporation of cells and DNA electrotransfer for controlled gene delivery. For example, the increased resistance across the electrode array due to use of a 10% concentration (isotonic) sucrose was shown to be approximately tenfold, relative to use of physiological saline-based solutions. This reduced the current required for voltage pulse-dependent electroporation by a corresponding ~30 fold. This was found to be effective for gene electrotransfer in both an in vitro HEK293 cell monolayer model example and in an in vivo model in the cochlea and brain.

Figure 23:
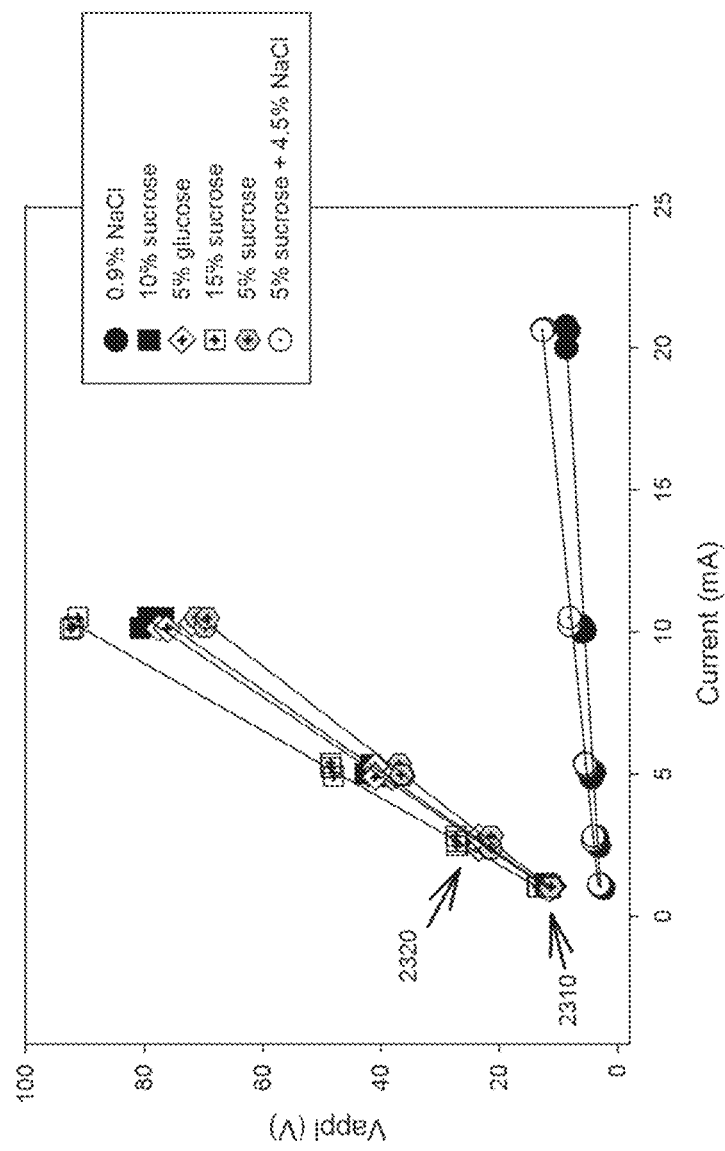
FIG. 23 shows effect of carrier solution composition on voltage applied (Vappl) to the electrode array for a range of constant current pulses of 100 ms duration.
Figure 24:
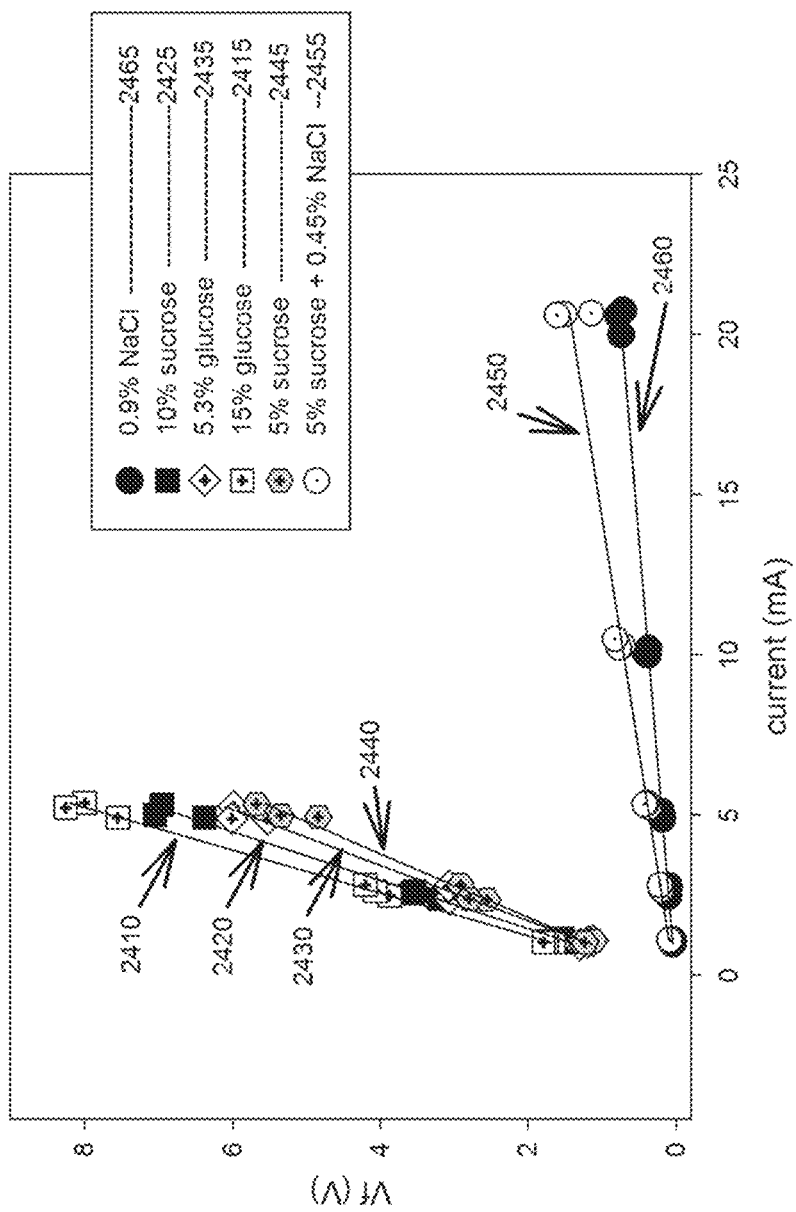
FIG. 24 shows plots of measured induced field results for a selection of carrier solutions during constant current pulses.

The influence of carrier solution on electroporation under regulated current conditions is discussed below with reference to FIGS. 23 to 25 which show results of measurement of local fields under constant current control with varying saccharose carrier solutions compared with a normal saline solution reference. FIG. 23 shows effect of carrier solution composition on voltage applied (Vappl) to the electrode array for a range of constant current pulses of 100 ms duration. Pulse measurements at ~95 ms. The cochlear implant array was wired with four anodes ganged and four cathodes ganged (tandem configuration).

The inventors used custom isolated amplifiers (electrode monitoring system) for recording current and voltage at the electrode array and measurement of the voltage within the electric field adjacent to the electrodes relative to a reference ground. Both the electrodes of the array and measurement probes were constructed of platinum. The inventors used solutions of varying concentration of sucrose or glucose and saline, including combinations thereof. Constant current was delivered using a Digitimer DS5 isolated constant current stimulator. The current pulses were controlled using an Axon Instruments 1440 interface with Clampex software. Current pulses were varied between 100 µs to 100 ms duration and were of varying amplitude up to 50 mA. Outputs of current and voltage from the Digitimer DS5 stimulator were recorded through this interface (100 kHz sampling rate per channel for 5 channels) along with independent measurements of the applied current, voltage at the electrode array, and voltage at a point within the electric field, via the custom built electrode monitoring system.

The array used for these tests was a Cochlear Ltd 8 node array (Cochlear Ltd. Part number Z60274) with 350 µm width platinum rings where there apical four electrodes were ganged together as anodes and the next four electrodes were ganged together as cathodes in the 'Tandem' configuration as describe above. Tests demonstrated, as shown in FIG. 23, that Sucrose (5%, 10%, 15%) and glucose (5.3%) solutions (buffered with 0.5 mM NaOH; osmolarities respectively: 154, 326, 520, 315 mOsm, measured with a micro-osmometer (Fiske model 210)) caused a large increase in the voltage at the array electrodes ($V_{applied}$) compared with normal saline (0.9% NaCl; 296 mOsm) or a combination of saline (0.45%) and sucrose (5%) (310 mOsm) for a given constant current pulse.

It is significant that all saccharose-based carrier solutions yielded voltages within the range of effective gene electrotransfer (~10 V) with 1 mA of current. Saline-based solutions required >20 mA of current to achieve this. Based on triplicate measurements, one way analysis of variance (ANOVA) statistical analysis was initially undertaken by comparing data for 1 mA applied, where the measured $V_{applied}$ where closest matched. There was a statistically significant difference between carrier solutions (P<0.001); Holm-Sidak pairwise comparison (α=0.05 for significance) indicated all saccharose carriers generated higher applied voltages than saline-containing solutions as shown in Table 1.

TABLE 1

Comparison of bionic array $V_{applied}$ with saccharose-based carrier solutions against normal saline.

| Group Name | N | Mean | Std Dev | SEM |
|---|---|---|---|---|
| 0.9% saline | 3 | 2.692 | 0.225 | 0.130 |
| 5% sucrose | 3 | 11.181 | 0.159 | 0.0916 |
| 10% sucrose | 3 | 11.794 | 0.389 | 0.225 |
| 15% sucrose | 3 | 13.539 | 0.0725 | 0.0418 |
| 0.45% sal & 5% sucr | 3 | 3.147 | 0.0412 | 0.0238 |
| 5.3% glucose | 3 | 11.456 | 0.463 | 0.267 |

| Comparison | Diff of Means | t | P | P < 0.050 |
|---|---|---|---|---|
| 15% sucrose vs. 0.9% saline | 47 | 48.584 | <0.001 | Yes |
| 15% sucrose vs. 0.45% sal & | 10.391 | 46.543 | <0.001 | Yes |
| 10% sucrose vs. 0.9% saline | 9.103 | 40.771 | <0.001 | Yes |
| 5.3% glucose vs. 0.9% saline | 8.765 | 39.257 | <0.001 | Yes |
| 10% sucrose vs. 0.45% sal & | 8.647 | 38.730 | <0.001 | Yes |
| 5% sucrose vs. 0.9% saline | 8.489 | 38.024 | <0.001 | Yes |
| 5.3% glucose vs. 0.45% sal & | 8.309 | 37.216 | <0.001 | Yes |
| 5% sucrose vs. 0.45% sal & | 8.034 | 35.983 | <0.001 | Yes |
| 15% sucrose vs. 5% sucrose | 2.358 | 10.560 | <0.001 | Yes |
| 15% sucrose vs. 5.3% glucose | 2.082 | 9.327 | <0.001 | Yes |
| 15% sucrose vs. 10% sucrose | 1.744 | 7.813 | <0.001 | Yes |
| 10% sucrose vs. 5% sucrose | 0.613 | 2.747 | 0.069 | No |
| 0.45% sal & vs. 0.9% saline | 0.456 | 2.041 | 0.180 | No |
| 10% sucrose vs. 5.3% glucose | 0.338 | 1.514 | 0.288 | No |
| 5.3% glucose vs. 5% sucrose | 0.275 | 1.233 | 0.241 | No |

$V_{applied}$ (measured in volts) during a 1 mA, 100 ms current pulse; Between Group variation P < 0.001, One Way ANOVA with Holm-Sidak Pairwise Comparisons.

As shown in the graph of FIG. 23, there was no significant difference in $V_{applied}$ (mean=11.48 V) between sucrose or glucose at 5-10% at the 1 mA level. However, analysis of $V_{applied}$ based on 2 mA×100 ms pulses 2320 resolved differences evident from FIG. 23 (mean±s.e.m; 5% sucrose=21.5±0.05 V; 5.3% glucose=22.9±0.52 V; 10% sucrose=23.4±0.42 V; 15% sucrose=27.2±0.03 V; P<0.05); where only 10% sucrose and 5.3% glucose were indistinguishable (P=0.336). With regard to the saccharose-based carriers, the increase in $V_{applied}$ with increasing current was approximately ohmic, allowing calculation of resistance from the respective slopes using linear regression best fits ($R^2$>0.98): 0.9% saline=299 0; 0.45% saline+5% sucrose=480 Ω; 5% sucrose=6.30 kΩ; 10% sucrose=7.16 kΩ; 15% sucrose=8.50 kΩ; 5.3% glucose=6.94 kΩ.

Analysis of the electric field for 1 mA×100 ms pulses was undertaken from a reference position ~500 µm orthogonal to the second from apical anode of the cochlear implant array. These data indicated that increases in voltage at the electrodes (Vappl) with saccharoses resulted in greater electric potentials in the field (Vf). The graph of FIG. 24, shows plots of measured induced field results for a selection of carrier solutions during constant current pulses. In FIG. 24 plot 2410 is of measured results for a 15% sucrose carrier solution 2415, plot 2420 is of measured results for a 10% sucrose carrier solution 2425, plot 2430 is of measured results for a 5.3% glucose carrier solution 2435, plot 2440 is of measured results for a 5% sucrose carrier solution 2445, plot 2450 is of measured results for a 5% sucrose+0.45% NaCl carrier solution 2455, and plot 2460 is of measured results for a 0.9% NaCl carrier solution 2465. These results show that saccharoses drive larger bionic array-induced field voltages than saline-based carrier solutions during constant current pulses. Measured field voltages (Vf) 2410, 2420, 2430, 2440 were significantly greater with saccharose carrier solutions 2415, 2425, 2435, 2445 than solutions containing NaCl 2455, 2465. Voltages were measured ~500 μm orthogonal to the second anode electrode of a cochlear implant array wired with four anodes ganged and four cathodes ganged.

Table 2 shows comparison of field voltages based on a One Way ANOVA for 2.5 mA current pulse.

TABLE 2

Comparison of field voltage (Vf) with saccharose-based carrier solutions against NaCl carriers.

| Group Name | N | Missing | Mean | Std Dev | SEM |
|---|---|---|---|---|---|
| 0.9% saline | 3 | 0 | 0.102 | 0.00514 | 0.00297 |
| 5% sucrose | 3 | 0 | 2.750 | 0.181 | 0.105 |
| 10% sucrose | 3 | 0 | 3.431 | 0.197 | 0.114 |
| 15% sucrose | 3 | 0 | 4.042 | 0.166 | 0.0958 |
| 0.45% sal & 5% sucr | 3 | 0 | 0.201 | 0.0142 | 0.00820 |
| 5.3% glucose | 3 | 0 | 2.985 | 0.137 | 0.0791 |

| Comparison | Means | t | P | P < 0.050 |
|---|---|---|---|---|
| 15% sucrose vs. 0.9% saline | 3.940 | 34.371 | <0.001 | Yes |
| 15% sucrose vs. 0.45% sal & | 3.841 | 33.506 | <0.001 | Yes |
| 10% sucrose vs. 0.9% saline | 3.329 | 29.040 | <0.001 | Yes |
| 10% sucrose vs. 0.45% sal & | 3.229 | 28.175 | <0.001 | Yes |
| 5.3% glucose vs. 0.9% saline | 2.883 | 25.148 | <0.001 | Yes |
| 5.3% glucose vs. 0.45% sal & | 2.783 | 24.283 | <0.001 | Yes |
| 5% sucrose vs. 0.9% saline | 2.648 | 23.104 | <0.001 | Yes |
| 5% sucrose vs. 0.45% sal & | 2.549 | 22.239 | <0.001 | Yes |
| 15% sucrose vs. 5% sucrose | 1.291 | 11.267 | <0.001 | Yes |
| 15% sucrose vs. 5.3% glucose | 1.057 | 9.223 | <0.001 | Yes |
| 10% sucrose vs. 5% sucrose | 0.680 | 5.936 | <0.001 | Yes |
| 15% sucrose vs. 10% sucrose | 0.611 | 5.331 | <0.001 | Yes |
| 10% sucrose vs. 5.3% glucose | 0.446 | 3.892 | 0.006 | Yes |
| 5.3% glucose vs. 5% sucrose | 0.234 | 2.044 | 0.123 | No |
| 0.45% sal & vs. 0.9% saline | 0.0991 | 0.865 | 0.404 | No |

$V_f$(measured in volts) during a 1 mA, 100 ms current pulse; Between Group variation P <0.001, One Way ANOVA with Holm-Sidak Pairwise Comparisons.

Figure 25:
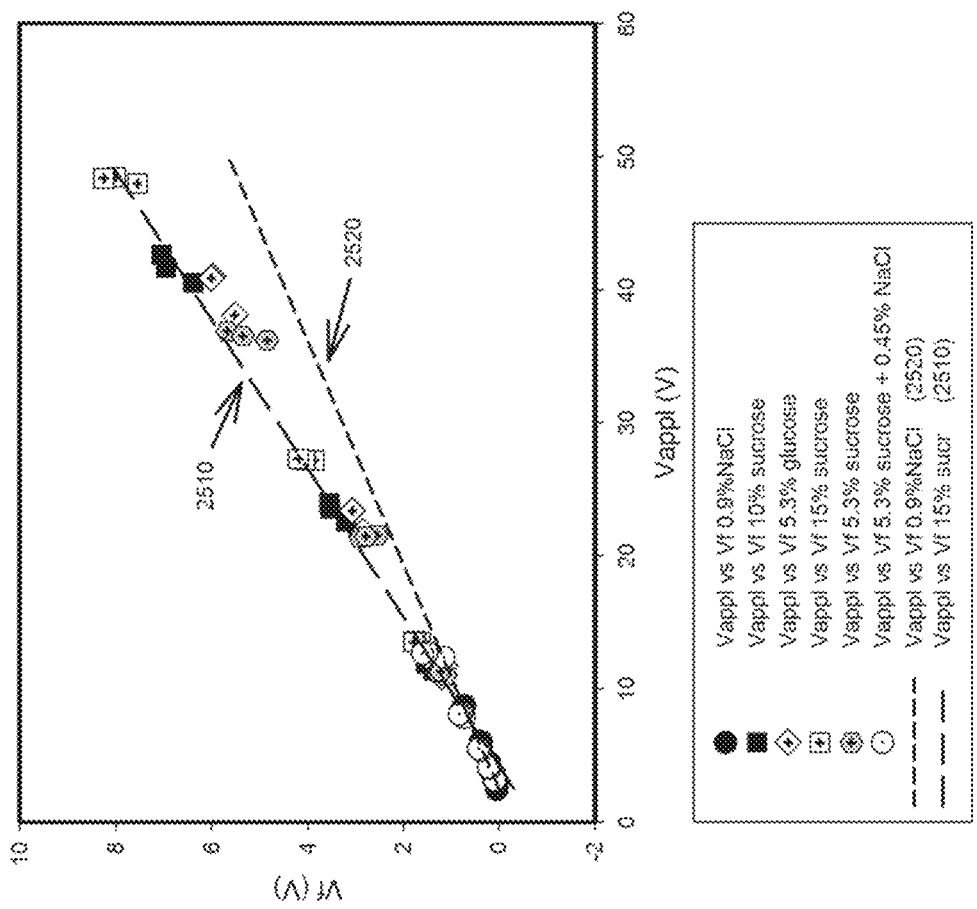
FIG. 25 is a graph of the electric potential measured in the field (Vf), adjacent to anode 2 of the bionic array, resulting from voltage applied (Vappl) to the array with saccharose— and NaCl—based carrier solutions.

FIG. 25 is a graph of the electric potential measured in the field (Vf), adjacent to anode 2 of the bionic array, resulting from voltage applied (Vappl) to the array with saccharose— and NaCl—based carrier solutions. As shown in FIG. 25 the plot 2510 of Vappl versus Vf indicated that the growth functions for saccharose-based carriers were approximately one third greater than that 2520 of NaCl-containing carriers for a given applied voltage. With 15% sucrose, Vf increased by 0.179×Vappl. ($R^2$=0.995 linear regression best fit), whereas in 0.9% NaCl, the Vf growth function was 0.119× Vappl. ($R^2$=0.978).

FIG. 25 shows that applied voltage with saccharose-based carriers generated approximately 33% greater field strength, based on a point measurement of voltage sampled in the field (Vf) for a given applied voltage than carrier solutions containing NaCl. Short dashed line 2520 is extrapolated linear regression best fit based on data from 0.9% NaCl carrier (Vf=−0.293+0.119×Vappl); long dashed line 2510 is best fit for 15% sucrose carrier (Vf=−0.751+0.179×Vappl). Applied voltages were obtained by using constant current pulses (100 ms) at 2.5 mA, 5 mA, 10 mA, 20 mA.

These data indicate that a higher close-field electric potential occurs with saccharose carriers than could be inferred by extrapolating from voltages applied to bionic arrays in saline-based carrier solutions. This indicated that required electric fields to achieve electroporation outcomes may be induced using lower voltage and current stimulation signals where saccharose-based carrier solutions are used than saline-based solutions. Further, the type and concentration of saccharose will also influence the induced field voltage.

Figure 26:
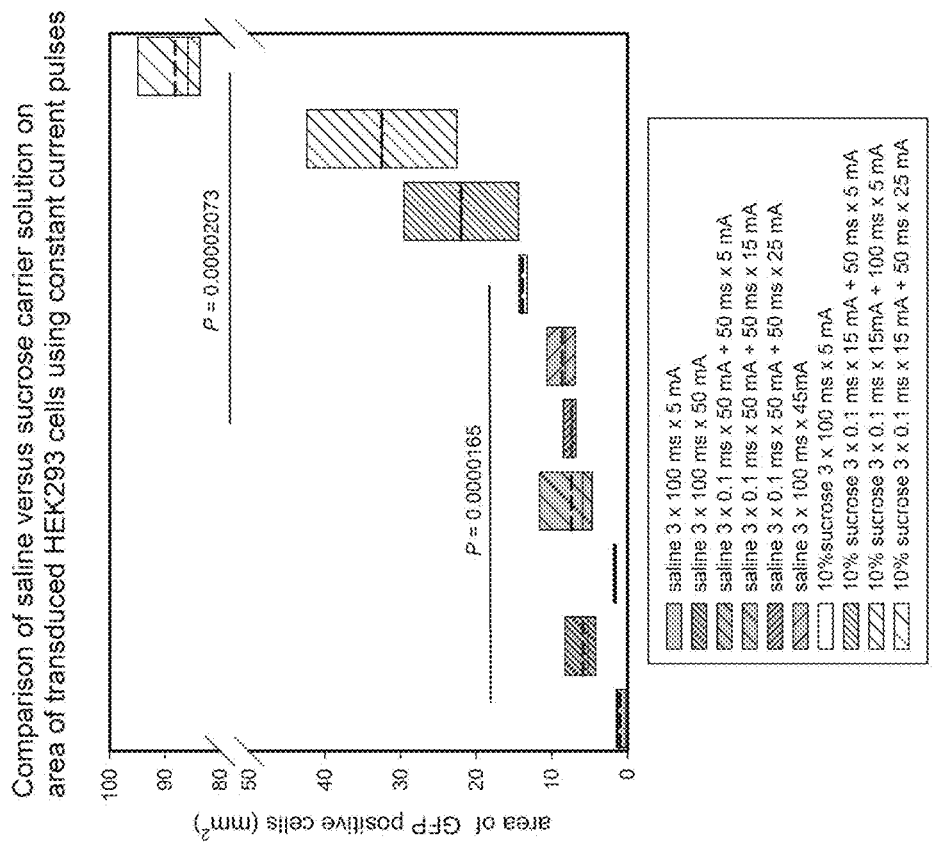
FIG. 26 shows a comparison of saline versus sucrose carrier solution on area of transduced HEK293 cells using constant current pulses.
Figure 28:
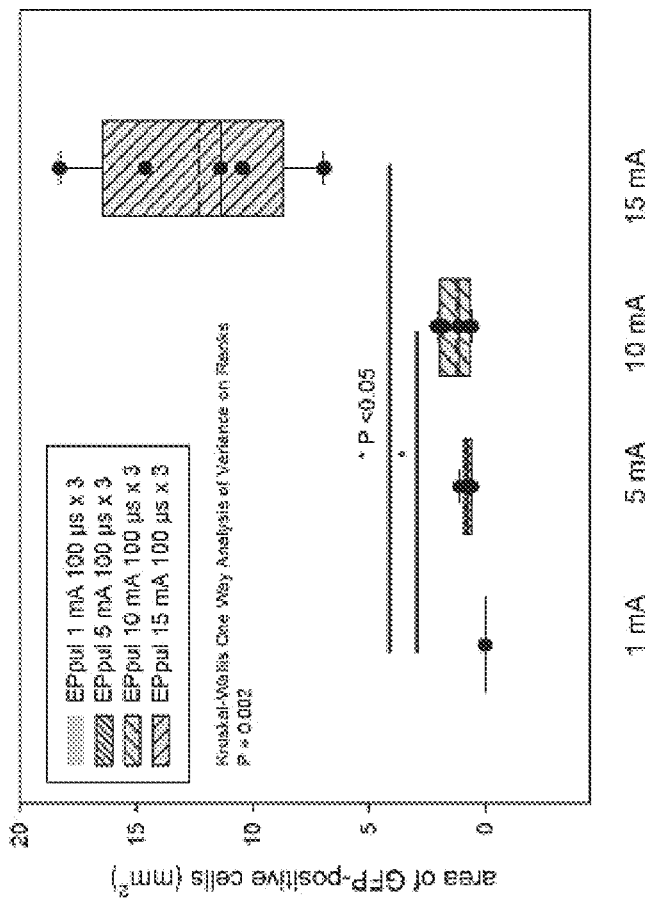
FIG. 28 is a boxplot showing areas of transfected cells (25% and 75% data boundaries with 95% confidence limits; individual data overlay; dashed lines indicate mean, median indicated as a solid line).

Further testing was performed using constant current pulses for close-field gene electrotransfer compared with constant voltage pulses. The results of this study are shown in FIGS. 26 to 28. The study established current pulse parameters for gene electrotransfer using a bionic electrode array and saccharose carrier versus saline solutions and compared these data with gene electrotransfer using constant voltage pulses. Naked GFP reporter plasmid DNA (2 μg/μl) was used to provide a readout of gene electrotransfer in confluent HEK293 cells on coverslips using an eight note cochlear implant array wired in Tandem configuration.

FIG. 26 shows a comparison of saline versus sucrose carrier solution on area of transduced HEK293 cells using constant current pulses. Of note, 3×5 mA of 100 ms duration, with 900 ms pulse gaps pulses, in 0.9% (normal) saline, produced an average field of GFP positive cells of 1.0±0.4 $mm^2$ (mean±s.e.m., n=3). The same pulse parameters using 10% sucrose as carrier solution resulted in an average area of 13.9±0.6 $mm^2$ (P=0.0000165, two tailed t-test), reflecting the higher electric field for the same current amplitude.

Effect of the use of dual pulse modes was investigated using three brief (100 μs) electroporation pulses of high amplitude (50 mA for saline, 15 mA for 10% sucrose), with 100 μs separation, followed by three×100 ms gene electrotransfer pulses of lower current amplitude (5 mA, 15 mA and 25 mA for saline; 5 mA and 25 mA for sucrose carrier). FIG. 26 indicates that the inclusion of the three brief electroporation pulses significantly increased the area of transduced cells in the presence of sucrose carrier, but not with the saline carrier. The inventors believe that this is because the maximum achievable electroporation applied voltages were higher in the sucrose solution. For example, comparing the 13.9 $mm^2$ area arising from 3×100 ms×5 mA pulses in 10% sucrose carrier, as above, with 32.5±9.9 $mm^2$ using 3×100 μs×15 mA then 3×100 ms×5 mA (n=2). The maximum area of electroporated cells, 88.1±9.9 $mm^2$ was achieved using 10% sucrose solution carrier with 3×100 μs×15 mA then 3×50 ms×25 mA (n=3), which compared with the maximum dual pulse protocol with saline (3×100 μs×50 mA then 3×50 ms×25 mA (n=3) that resulted in an area of 7.5±0.5 $mm^2$ (n=3) (P=0.00002073).

The effect of brief (100 μs) electroporation pulses was examined separate to the paired pulse protocol. The results of this testing are shown in FIGS. 27 and 28, showing the effectiveness of 100 μs electroporation pulses on plasmid gene electrotransfer in HEK293 cells. Areas of transfected cells increased progressively with increasing current pulse amplitude. Three constant current pulses were separated by 100 μs inter-pulse periods. 10 and 15 mA pulse amplitudes resulted in gene expression significantly greater than the 1 mA pulses (ranked ANOVA and Dunn's posthoc pairwise comparisons). FIG. 27 is a set of photographs A-D showing Fluorescence images of GFP expression by HEK293 cells. FIG. 28 is a boxplot showing areas of transfected cells (25% and 75% data boundaries with 95% confidence limits; individual data overlay; dashed lines indicate mean, median indicated as a solid line). The tests were performed with GFP reporter plasmid DNA (2 μg/μl) in 10% sucrose carrier. The electrical pulses were applied to an eight electrode cochlear implant array wired in Tandem configuration. Current was delivered through a Digitimer DS5 constant current stimulator driven through an analogue controller interface.

In this case just the 3×100 μs pulses separated by 100 μs intervals was used at 1 mA, 5 mA, 10 mA and 15 mA. In 10% sucrose carrier, the 1 mA pulses were ineffective (Mean=0.0009±0.0003 $mm^2$; P=0.0648—two tailed one-sample t-test, n=3; but 5-15 mA pulses produced progressively larger areas of GFP positive HEK293 cells (FIG. 28); range 0.769±0.077 mm$^2$ (5 mA; P=0.000172, two tailed one-sample t-test, n=6) to 12.329±1.927 mm$^2$ (15 mA; P=0.00306, two tailed one-sample t-test, n=5). These data are remarkable in that 100 µs pre-pulses up to the maximum output of the constant current power supply (50 mA) did not affect gene-electrotransfer efficiency in saline carrier compared with the ms pulse data (FIG. 26). The results are also highly significant in that the area of transfected cells obtained with the 3×100 µs×15 mA pulses (12.33±1.927 mm$^2$) was equivalent to that achieved with 3×100 ms pulses at 5 mA (13.87±0.325, n=3) (P=0.570, two-tailed t-test indicates no significant difference between these conditions). The difference in charge transfer of the pulse trains to achieve equivalent gene expression in 10% sucrose carrier is considerable (1.5×10$^{-3}$ C for the 3×100 ms×5 mA condition, vs 4.5×10$^{-6}$ C for the 3×100 µs×15 mA condition), with the higher current level affording a considerable reduction in overall charge required for gene electrotransfer.

Figure 30:
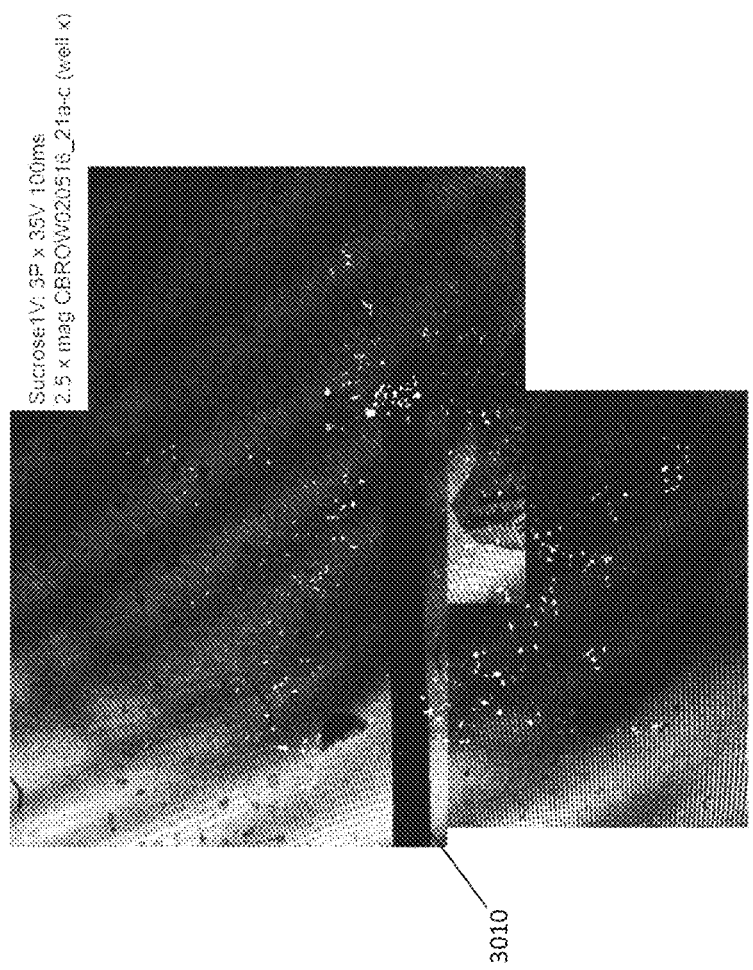
FIG. 30 is a photograph of the electrotransfer outcome for the 35 V 100 ms pulses using a 10% sucrose carrier solution.
Figure 29:
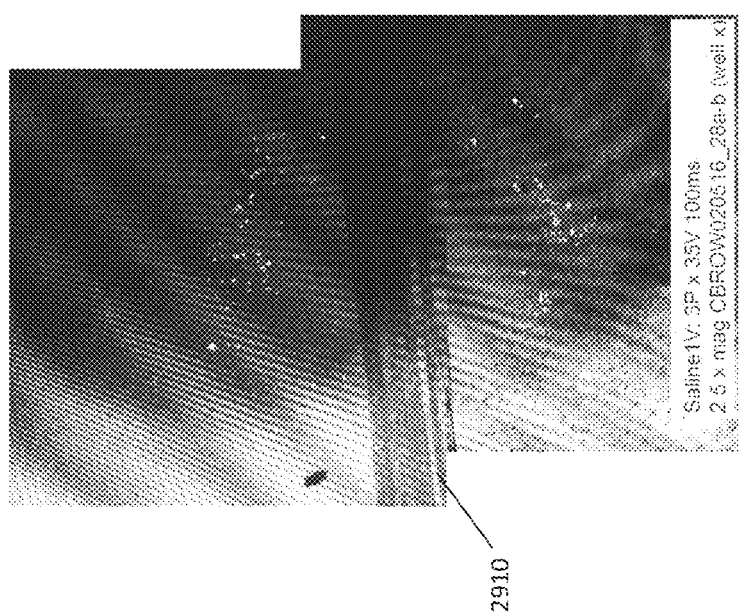
FIG. 29 is a photograph of the electrotransfer outcome for the 35 V 100 ms pulses using a saline carrier.
Figure 31:
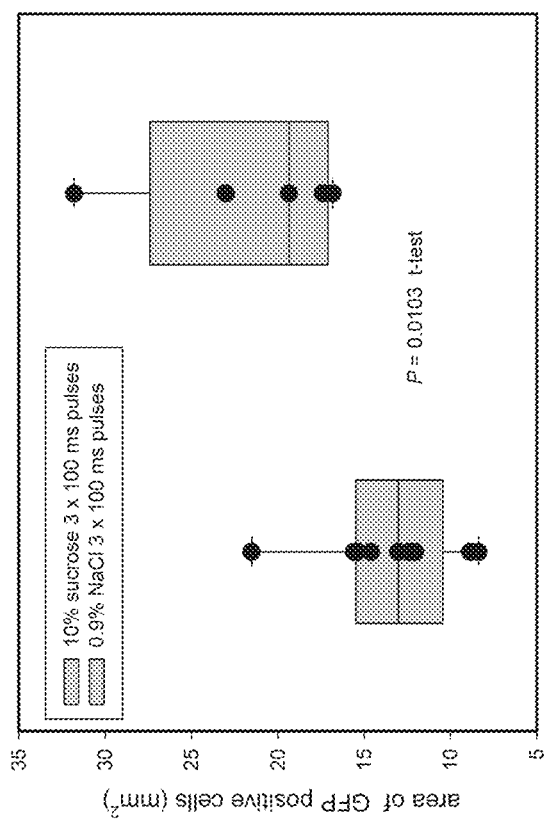
FIG. 31 is a graphical comparison of saline (0.9% NaCl) carrier solution versus 10% sucrose carrier solution on the area of transduced HEK293 cells using constant current matched to deliver 35V applied voltage at the tandem configured array.

The maximum current amplitude (50 mA) was capable of delivering ~35 V applied to the tandem configured eight node cochlear implant array in normal saline; this applied voltage was obtained with 10% of the current with 10% sucrose carrier (see FIG. 31). Here we compared the effect of 35 V applied at the electrodes with constant current in normal saline (0.9% NaCl (n=4) including with TRIS buffer (n=5); 3×100 ms×50 mA) against use of 10% sucrose carrier (3×100 ms×5 mA, n=5). A two tailed t-test indicated a significant (P=0.0103) increase in area of transduced cells with use of sucrose carrier, despite the matching of applied voltage, suggesting an effect of sucrose to enhance gene electrotransfer beyond the increase in electrode voltage from the change in resistivity of the solution. The comparative results of the electrotransfer are shown in FIGS. 29 to 31. FIGS. 29 and 30 are photographs of examples of areas of GFP positive HEK293 cells transduced in saline (0.9% NaCl) and 10% sucrose using constant current pulses matched to produce 35 V applied at the tandem configured eight node cochlear implant array. FIG. 29 is a photograph of the electrotransfer outcome for the 35 V 100 ms pulses using a saline carrier, and FIG. 30 is a photograph of the electrotransfer outcome for the 35 V 100 ms pulses using a 10% sucrose carrier solution. The current pulses were 3×100 ms (50 mA for NaCl carrier of FIG. 29 and 5 mA for sucrose carrier of FIG. 30). Each region of interest is 4.85 mm$^2$ and the position of the electrode array is marked 2910, 3010. Note the larger area of transduced cells with the sucrose carrier on FIG. 30. FIG. 31 is a graphical comparison of saline (0.9% NaCl) carrier solution versus 10% sucrose carrier solution on the area of transduced HEK293 cells using constant current matched to deliver 35V applied voltage at the tandem configured array. Statistical comparison used a two-tailed t-test.

The inventors have also performed testing comparing electrical fields with and without DNA, using sucrose and saline carriers. This testing used the cochlear implant array (8 node, tandem configuration) imaged on the microscope stage and the field voltage (Vf) was sampled 0.5 mm perpendicular to electrode position 2 (second anode from apex) using an isolated voltage amplifier with an insulated Pt electrode, referenced to a Pt electrode in the bath. Vf was measured relative to a range of 100 ms current pulses of varying amplitude applied to the electrode array. The voltage at the electrodes (Vappl) was measured as the output from the constant current power supply (Digitimer DS5). Vappl and Vf were compared with and without Salmon sperm DNA (Thermo Fisher; 2 µg/µl, average 2 kB fragments) included in the carrier solution.

Results of this testing demonstrated that adding DNA to saccharose carrier solution reduces resistivity whereas DNA added to the saline carrier increased the resistance. Measurements of resistivity (based on current flow for applied voltage) are shown in Table 3 and the effect of the resistance is evident in FIG. 32 as the difference in slopes of the applied voltage (Vappl) versus current data.

TABLE 3

Resistivity of sucrose and saline carrier solutions.

| Carrier | Resistance with DNA (2 µg/µl) | Resistance without DNA |
| --- | --- | --- |
| 10% sucrose | 9.550 kΩ* | 13.220 kΩ* |
|  | 10.773 kΩ | — |
| 0.9% Saline | 0.260 kΩ* | 0.222 kΩ* |
|  | 0.235 kΩ | 0.193 kΩ |

The carrier solutions all included 0.5 mM NaOH pH adjustment.
*indicates direct measurement using Napagene CU1; other measurement via slope of linear regression best fit ($R^2$ = 0.89 – 1.0). Constant current pulses (100 ms) were applied to the tandem array via a Digitimer DS5 stimulator.

Figure 32:
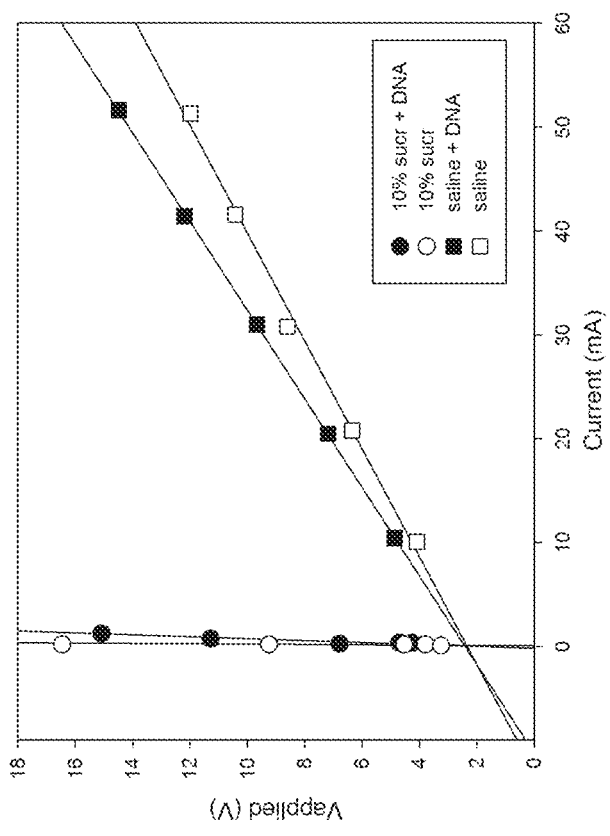
FIG. 32 shows a plot of applied voltage achieved at tandem array for varying current pulse input across sucrose vs saline carriers with and without salmon sperm DNA (2 µg/µl).
Figure 33:
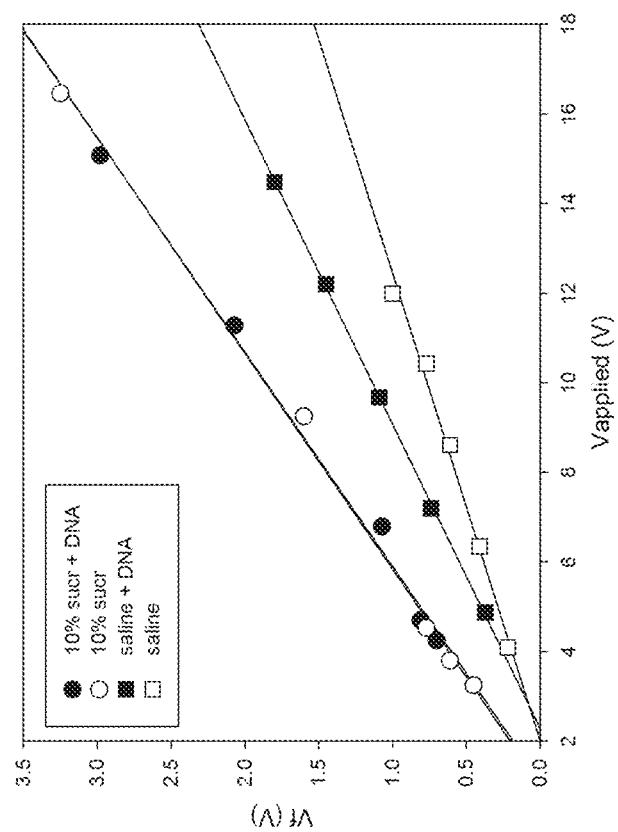
FIG. 33 shows field voltages generated by different tandem array applied voltages, measured 0.5 mm lateral to anode 2.

FIGS. 32 and 33 show the effect of salmon sperm DNA (2 µg/µl) on Vappl and Vf in normal saline (0.9%) and 10% sucrose (both buffered with 0.5 mM NaOH). FIG. 32 shows a plot of applied voltage achieved at tandem array for varying current pulse input across sucrose vs saline carriers with and without salmon sperm DNA (2 µg/µl). FIG. 33 shows field voltages generated by different tandem array applied voltages, measured 0.5 mm lateral to anode 2. Sucrose and saline carriers were compared, with and without salmon sperm DNA (2 µg/µl). FIG. 33 shows that with 10% sucrose carrier, irrespective of DNA, Vapplied generates a similar Vf (Vf for10% sucr+DNA=−0.237+(0.209*Vappl-10% sucr+DNA; $R^2$=0.993); Vf 10% sucr without DNA=−0.214+(0.208*Vappl 10% sucr; $R^2$=0.997)). In the case of 0.9% saline with DNA, the best fit provides a slope of 0.147 V/V (Vf sal+DNA=−0.336+(0.147*Vapp saline+DNA; $R^2$=1.0), whereas without DNA the slope is 0.0958 V/V (Vf saline without DNA=−0.193+(0.0958*Vapp sal no DNA; $R^2$=0.989).

Raster Measurement of Electric Field Along the Array Using Sucrose

Figure 35:
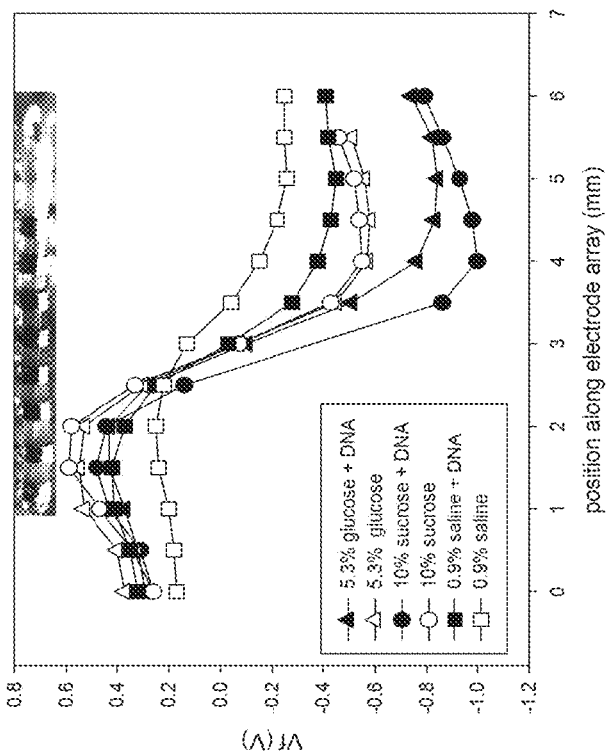
FIG. 35 shows a raster scan of voltages sampled in the field (Vf) measured along the array 0.5 mm distant to the surface.
Figure 34:
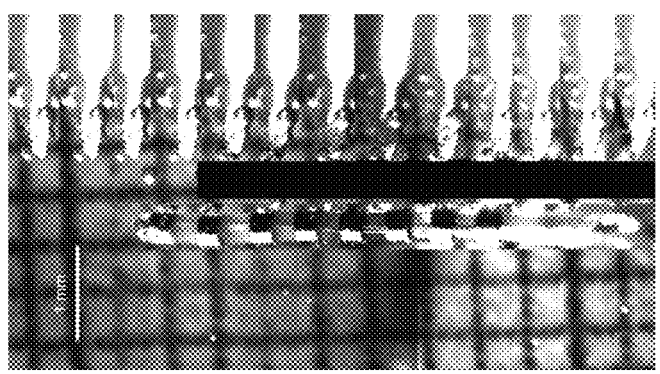
FIG. 34 is an image showing configuration for sampling of electric field (Vf) measured at regular intervals along the array.

The Vf for 10% sucrose carrier (without DNA) solution was measured along the length of the tandem array using 5 V constant voltage pulses (100 ms; AM Systems 2200 stimulator) (FIGS. 34 and 35). FIG. 34 is an image showing configuration for sampling of electric field (Vf) measured at regular intervals along the array. The image is a composite showing overlay of the Vf sampling electrode at the various positions along the length of the cochlear implant array. FIG. 35 shows a raster scan of voltages sampled in the field (Vf) measured along the array 0.5 mm distant to the surface. The electric field strength is highest in the mid-region of the array (evident in FIG. 35 as steepest change in voltage versus distance along the array). Electrodes 1-4 were ganged as anodes, electrodes 5-8 were cathodes (Tandem array configuration). Glucose, sucrose and normal saline carriers are compared with and without DNA. The electric field map for 10% sucrose carrier solution (no DNA) is shown as FIG. 36 using 40 V pulses (100 ms). This highlights the compression of the field around the null position between the ganged anodes and cathodes of the tandem array.

As shown in FIG. 35, the field strength with 5.3% glucose or 10% sucrose was higher than that of 0.9% saline. The presence of DNA (2 µg/µl) adds appreciably to the field strength for all carriers. The increase in field strength for a common applied voltage (Vappl=5 V) in the saccharose carrier solutions is commensurate with the noted increase in area of GFP positive HEK293 cells evident with these carriers compared with saline carrier. The maximum field strengths (slopes of the plots between 2 mm and 3.5 mm in FIG. 35) were: 5.3% Glucose+DNA=6.4 V/cm (max Vf change=1.785−(0.640 V/mm*max field pos); 10% Sucrose+DNA=8.86 V/cm (max Vf change=2.269−(0.886 V/mm*max field pos); 0.9% saline+DNA=4.46 V/cm (max Vf change=1.304−(0.446 V/mm*max field pos). Rank order of Field strength due to carrier including DNA: 10% sucrose>5.3% sucrose>0.9% saline.

Figure 36:
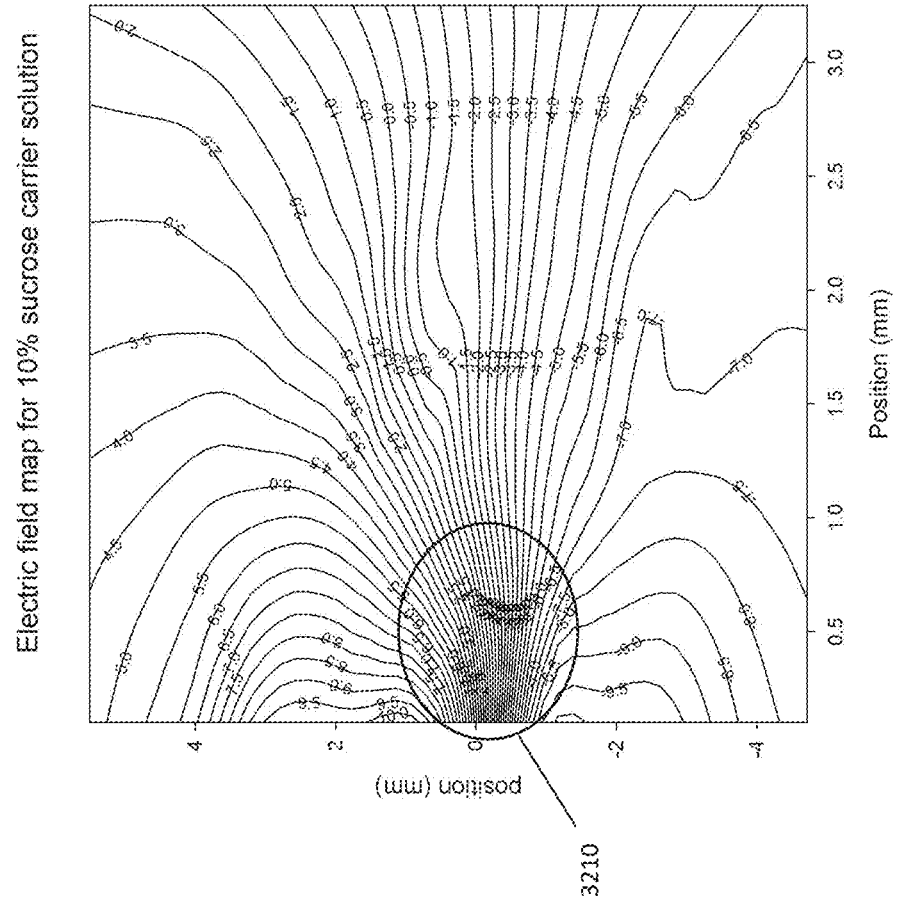
FIG. 36 shows a 2D electric field map of the right side (hemifield) for a tandem configuration electrode array in 10% sucrose carrier solution (no DNA) using 40 volts applied (AM systems 2200 constant voltage stimulator).

FIG. 36 Shows a 2D electric field map of the right side (hemifield) for a tandem configuration electrode array in 10% sucrose carrier solution (no DNA) using 40 volts applied (AM systems 2200 constant voltage stimulator). Y axis is position along the array relative to the null point between anode 4 and cathode 1. The electrode array is 5.5 mm in length; upper region consisted of four electrodes ganged as anodes (+ve), basal half had four electrodes ganged as cathodes (-ve). The most intense region of the field 3610 is orthogonal to the null point of the array which is the mid-region of the array (position 0 on the y axis).

Figure 37:
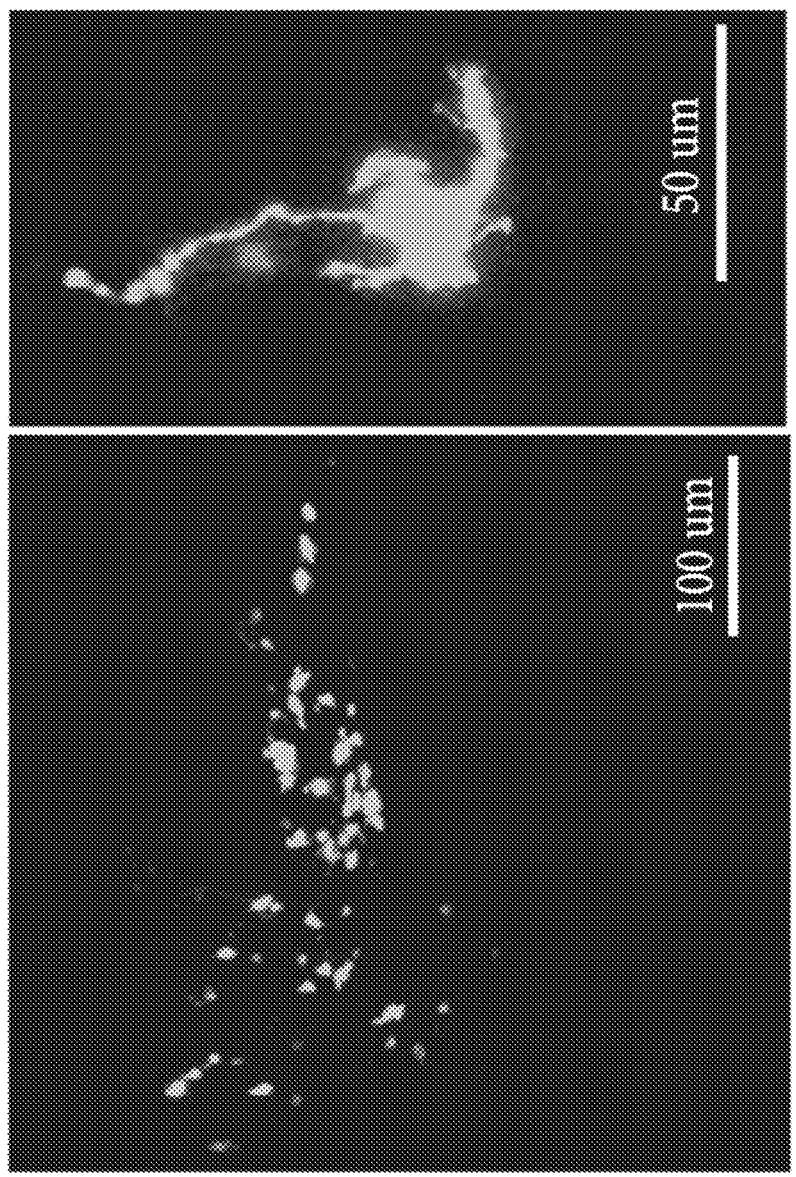
FIG. 37 shows GFP positive neurons in the guinea pig dorsal brainstem (nucleus tractus solitarius region) 7 days after gene electrotransfer of the plasmid GFP reporter DNA construct.

FIGS. 37 to 40 demonstrate enablement of the use of constant current pulses and sucrose carrier solution for bionic array-based gene electrotransfer in vivo. FIG. 37 is a set of in vivo image of GFP fluorescence in a group of neurons in the guinea pig dorsal brainstem (nucleus tractus solitarius region) achieved using 10% sucrose carrier solution with a bionic array wired in Tandem configuration. Plasmid reporter DNA was the μCBA-eGFP (2 μg/μl). Tissue was imaged after fixation (4% paraformaldehyde) 7 days after gene electrotransfer using constant current pulses 3×10 mA×100 ms pulses (Vappl=35 V).

Figure 38:
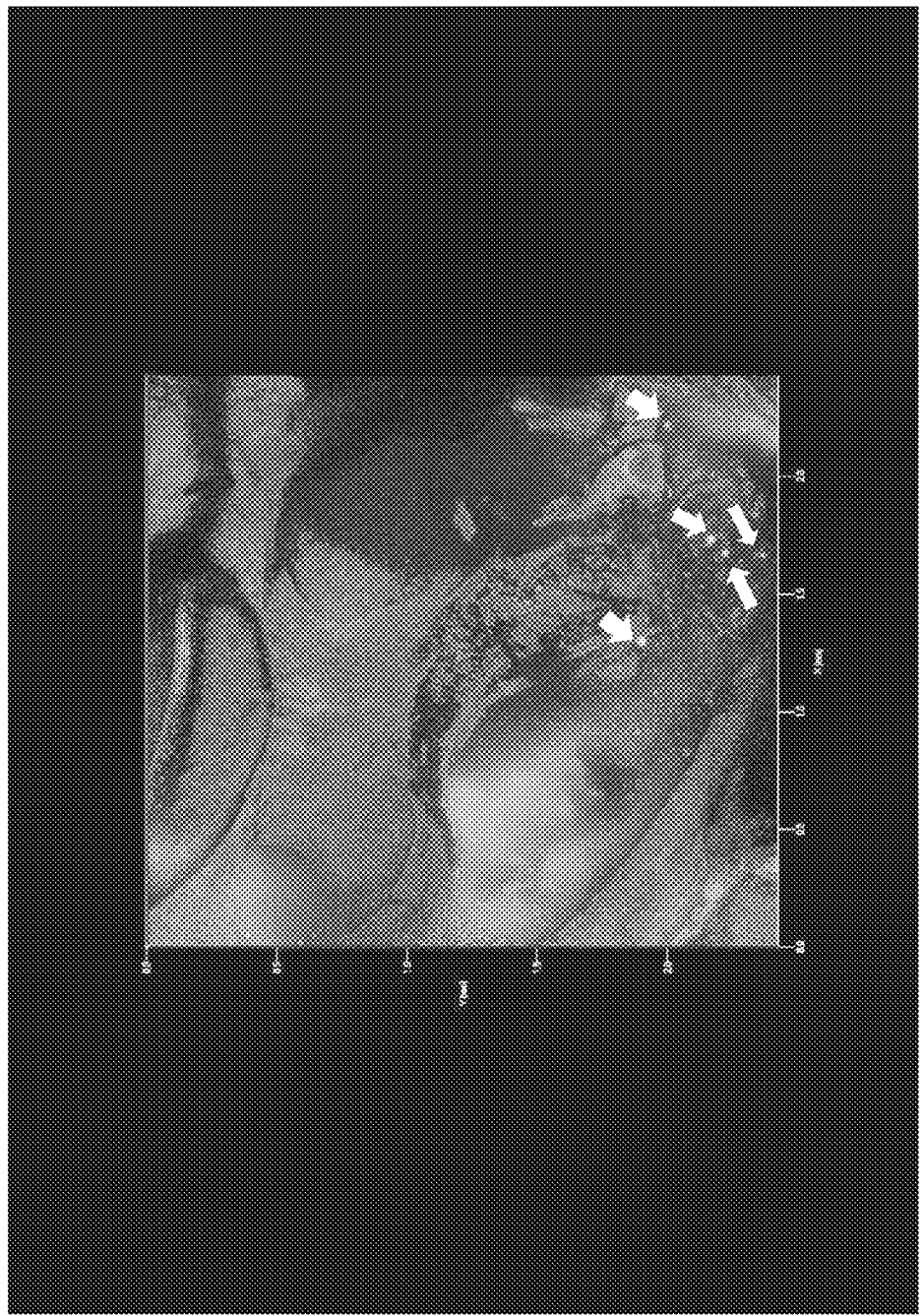
FIG. 38 is an in vivo image of cochlear gene delivery with sucrose carrier (GFP labelled mesenchymal cells lining scala tympani) four days after gene electrotransfer using 3×2 mA×100 ms pulses (Vappl=20 V).
Figure 39:
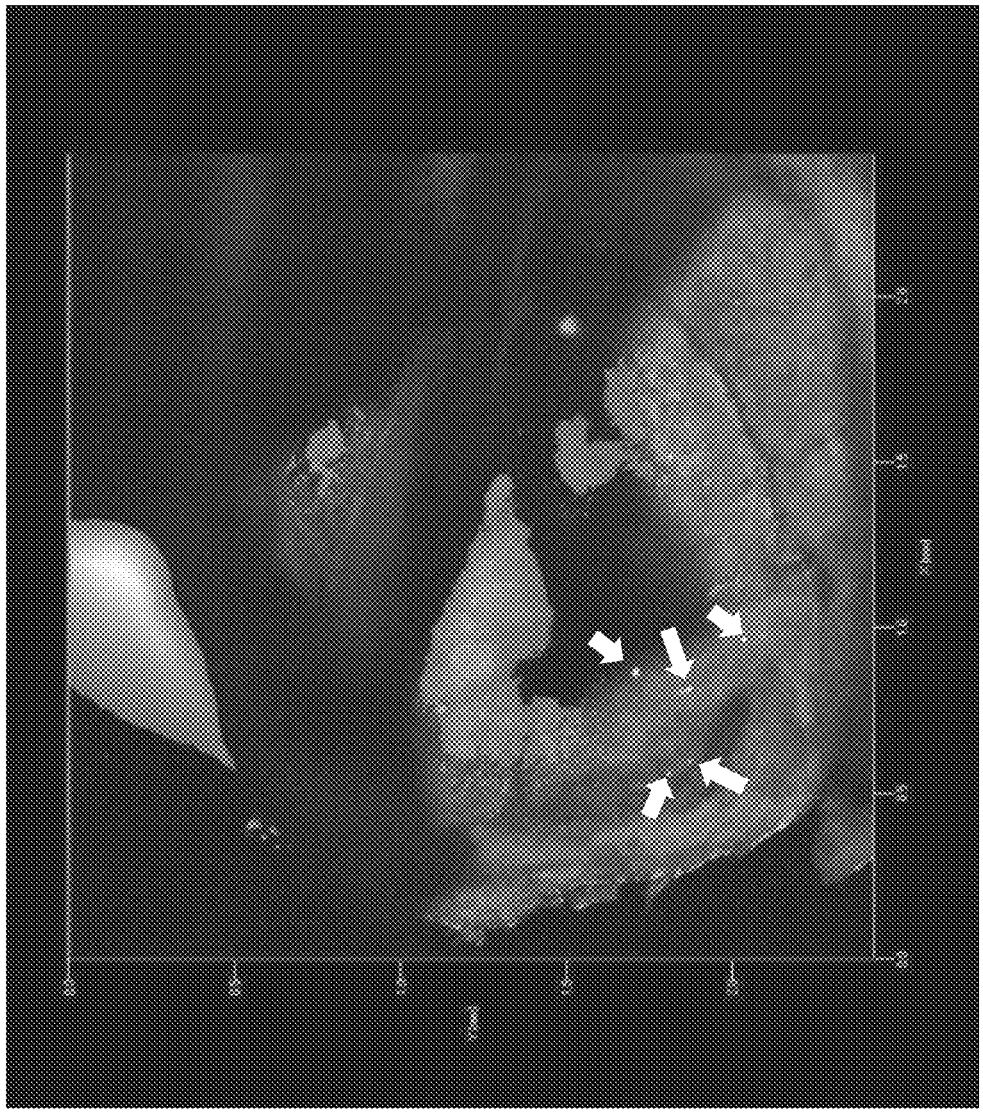
FIG. 39 is an in vivo image of cochlear gene delivery with sucrose carrier (GFP labelled mesenchymal cells lining scala tympani) four days after gene electrotransfer using 3×1 mA×100 ms pulses (Vappl=12 V) via a constant current power supply (Digitimer DS5 stimulator).

The images in FIGS. 38 and 39 are in vivo images of cochlear gene delivery with sucrose carrier (GFP labelled mesenchymal cells lining scala tympani). DNA was μCBA-eGFP plasmid (2 μg/μl). Tissue was imaged after fixation with 4% paraformaldehyde 4 days after gene electrotransfer with a bionic array wired in Tandem configuration; 10% sucrose carrier. Hemisectioned cochlea four weeks decalcification. These figures show GFP positive guinea pig cochlear mesenchymal cells (green) lining the basal turn of scala tympani. The experiment for the data shown in FIG. 38 used 3×2 mA×100 ms pulses (Vappl=20 V) and experiment for the data in FIG. 39 used 3×1 mA×100 ms pulses (Vappl=12 V) via a constant current power supply (Digitimer DS5 stimulator).

As discussed above, controlling the geometry of the electric field enables spatial targeting of a region for electroporation treatment and the intensity of the electric field, Vf, induced by the electroporation pulses controls the number of cells transfected. Selection of carrier solution and DNA concentration can enable variation of field intensities and influence field geometry. In particular saccharose-based carrier solutions have been shown to enable driving electroporation stimulation pulses to use lower current and voltage amplitudes to achieve cell transfection than for saline-based carrier solutions. Thus the cumulative charge delivered to achieve cell transfection can be reduced by choice of carrier solution. This can have advantages such as reduced risk of electromechanical toxicity during treatment, and reduction in stimulation pulse delivery requirements. Embodiments of systems and methods for providing controlled electroporation are discussed in further detail below.

Embodiments of the system can enable more efficient transfection of DNA, therapeutic molecules or other agents. Embodiments of the present invention are directed to an electroporation probe and system configured to generate non-uniform orthogonal electric fields in one or more target regions for electroporation. Embodiments of the system enable focusing of electric fields within parameters that enable cells to take up naked DNA.

Overview of System Embodiment

A simple embodiment of an electroporation system of the invention is illustrated in the block diagram of FIG. 1. The system 100 comprises an electroporation probe 110 and a pulse generator 120. The electroporation probe or array 110 configured to be temporarily inserted into biological tissue for electroporation treatment and has at least two contiguous electrodes. Preferably the spacing between each pair of contiguous electrodes driven as an anode and cathode is less than one mm, in order to induce high electric field gradients between the pair of electrodes.

The pulse generator 120 is electrically connected to the probe and configured to drive the electroporation probe using a sequence of one or more electric pulses to cause current transmission through the probe and induce a non-uniform electric field in the biological tissue proximate the probe electrodes. The pulse generator 120 can be either voltage or current controlled to supply a sequence of one or more pulses of controlled magnitude and duration to the probe 110. The pulse generator is not limited to a single source producing a single series of pulses. For example, there could be multiple current sources and sinks activated simultaneously on various electrodes to shape the field.

The shape of the electric field is influenced by the physical configuration of the electrodes and polarities for driving the electrodes by the pulse generator. Further, varying the pulse duration, magnitude, number of pulses and carrier solution will affect the number of cell transformations. The pulse duration, magnitude and number of pulses may be controlled based on the therapeutic agent carrier solution provided for the treatment and desired treatment outcomes. Thus, by varying the electrode array configuration for the probe and how the array elements (electrodes) are driven by the pulse generator the shape of the electric field can be controlled, enabling targeting of specific tissue for electroporation. It is envisaged that electroporation probes can be produced having a variety of configurations, each suitable for use to produce a different shaped field. Thus, probes can be tailored for specific clinical applications or even specific patients. The physical configuration of the probe electrode array provides one aspect for control of the electric field, the other aspect of configuration is connection of electrodes as anodes and cathodes. In some embodiments the pulse generator or an electroporation controller may be adapted to selectively configure the electrode array elements as anodes and cathodes.

Control of the electric field and driving pulses allows regulation of the spatial field of transduced cells in terms of the size and shape of the field and the density of transduced cells within the field. Put another way, embodiments of the invention enable "dial-up" control of local directed gene delivery. Another variable in control of gene delivery is the carrier solution. Is should be appreciated that in some applications the carrier solution may be a variable when determining a gene therapy treatment, with the choice of carrier solution being selectable by the clinician. However, it should be appreciated that the carrier solution may also be preselected, for example by a manufacturer, and only one or a small number of carrier solution options made available to the clinician for selection. In an example of an embodiment of the electroporation system suitable for DNA delivery, the probe electrodes and driving pulses are configured to produce a non-uniform electric field orthogonal to the array including electric field gradients in the range of 50 μV/μm to 1500 μV/μm. Other electroporation applications may have different target field parameters, for example, suitable to different types of cells and therapeutic agents, and all such variations are contemplated within the scope of the present invention. It envisaged that embodiments of the electroporation system of the invention can be configured suitably for different types of treatments and target cells by modifying the probe configuration and driving parameters to produce electric fields with targeted non-uniformity parameters. The driving parameters can also be chosen based on the carrier solution to be used. The system may serve to deliver a broad range of molecules to cells by creating the focused electric fields which transiently permeabilize the cell membrane to permit molecular translocation.

Details of Probe/Electrode Array Configurations

An aspect of the system is an interface or probe 110 comprising an array of electrodes which can be inserted into biological tissue to deliver a shaped electric field capable of causing electroporation of the cells in a controllable manner relative to the spatial configuration of the electrode array. Electroporation probes 110 of the present invention are designed for temporary insertion into biological tissue for the purpose of gene delivery, or delivery of other therapeutic molecules via transient electroporation of cells.

An embodiment provides a non-implantable 'electroporation gene delivery probe' (EGD-P). This probe, which consists of an array of two or more electrodes, which when driven acutely by electrical pulses from a pulse generator (voltage or current source) will enable electroporation of cells adjacent to the probe. Preferably the separation between electrodes is less than 1 mm. An example of a prototype probe is shown in FIG. 2a and a corresponding schematic shown in FIG. 2b. The electroporation probe comprises two or more electrodes which are physically connected for insertion into tissue (not separated by tissue) and are configured to focus the electric fields generated by passing current from one or more electrodes to the other(s) for the purpose of close-field electroporation delivery of molecules, particularly DNA. The prototype probe 210 comprises two conductive insulated wires ensheathed by a cannula with the electrode array 220 formed in the distal tip of the probe 210. FIG. 2b is a schematic illustrating the electrode array configuration in more detail. The two insulated wires 230 extend through the length of the probe to the tip. Along sections of the wire the insulation is removed 240 to form the electrode. As is shown in FIG. 2b insulation can be removed from a section of each wire juxtaposed in the longitudinal direction of the probe to form contiguous electrode pairs. In the embodiment shown the electrode pairs are formed in a section approximately 2 mm long with less than 1 mm separation between the electrodes. The number and spacing of the electrode pairs can be chosen for the target treatment field area. In particular this embodiment uses sub mm separation between anode and cathode poles within the array—to target the treatment field in the region of the electrode pairs. Multiple electrode pairs can be used along the length of the probe to extend the target treatment area along the probe. In this embodiment each wire will be driven using a different polarity, so the electrodes along one wire will be anodes and electrodes on the other wire the cathodes. For example, where the wires are electrically connected to positive and negative terminals of the pulse generator respectively.

In this embodiment the cannula can also be used for delivery of the therapeutic agent (DNA, drug or other molecules) and in the region of the electrodes the cannula is perforated to permit therapeutic agent delivery and provide a current path. In the case of electrodes ensheathed by a cannula or other material that has electrical insulation properties, the electrical conductance of the probe may be controlled by the physical or material properties of the port associated with the electrode. It should be appreciated that this embodiment allows delivery of the therapeutic agent to the target area for electroporation between the electrodes and contribute to the shaping of the electric fields generated by the array. In some embodiments the therapeutic agent delivery may be controlled in conjunction with the electroporation. The configurations of the probe's array of electrodes enable control of the shape and density of the field of transformed cells. This device will enable 'dial-up' transcellular therapeutics delivery, ideal for localized gene therapy.

It should be appreciated that the dimensions of the portion of the probe designed for insertion into tissue can have a very narrow diameter (for example less than 200 μm in the prototype shown) allowing minimally invasive treatment. The probe may also be configured to have physical properties to aid insertion into tissue, for example a balance of stiffness and flexibility to allow controlled placement while being compliant with the biological tissue. The device is compliant with respect to tissue, such that its physical properties permit insertion into tissue whilst maintaining a desired shape, or responding to mechanical stress within the tissue to adopt a shape which enables the positioning of the electrodes within the array in close proximity to the target cell population within the tissue. The cannula will be configured to deliver a therapeutic agent solution and may be constrained by properties of the solution, for example molecule size, solution viscosity etc. In some embodiments the therapeutic agent solution may be chosen to be suitable for delivery via the probe. For example, low viscosity solutions may be chosen for some types of treatments (for example, neonatal, paediatric or neurology treatments) to allow smaller probes with narrower catheters to be used; this may include lower viscosity saccharoses, such as iso-osmolar glucose over sucrose carrier.

The probe comprises two or more electrodes which are physically connected for insertion into tissue and are configured to focus the electric fields generated by passing current from one or more electrodes to the other(s) for the purpose of electroporation delivery of molecules, particularly DNA. In preferred embodiments the electrode array is configured such that the electric fields are constructed to establish electric field gradients in the range of 50 μV/μm to 1500 μV/μm irrespective of reference potential at a distance of 150 μm from the electrode surface. In a preferred embodiment the electrodes consist of a minimum of two adjacent electrodes with electrode dimensions typically 1 mm in length, and <1 mm in circumference.

The probe electrodes may be configured in a linear array, or spread across a surface to form a two dimensional array or even a three dimensional array, for example a planar, curved/conformal surface respectively. A two or three dimensional array configuration may also be provided using a plurality of linear probes each carrying an electrode pair.

In an embodiment a two dimensional array may be formed on a flexible sheet to allow shaping of the array to tissue during implantation.

The electric field shaping may be regulated by the wiring of varying configurations of anodes and cathodes within the electrode array, in which case the electrodes may be of smaller physical dimensions, (<1 mm length/circumference >50 μm length/circumference). For example, transformation of cells with DNA may be achieved in a vector in parallel with a linear array using relatively closely spaced alternating anode and cathode electrodes, while spherical shaped fields of transformed cells extending orthogonally to a linear array may be achieved using elongate anodes and cathodes or by driving sets of adjacent electrodes together (ganged) as anodes and cathodes and passing current locally between the electrodes.

The electroporation gene delivery probe (EGD-P) is conceived as a class of medical device—establishing a range of electrode array probes which are designed as biological interfaces for acute gene delivery in the broadest range of biological tissues, in vivo, or in cell and tissue culture conditions. For clinical use, the probes would be used acutely, where as a packaged consumable, they are inserted to the target region within a tissue, such as the brain, and by passing current (or alternatively by applying a differential voltage) locally from a subset of electrodes within the array to another subset of the electrodes within the array, generate localized shaped electric fields that enable electroporation and electrophoretic action upon cells in the vicinity of the probe that results in translocation of the therapeutic DNA across the cell membrane of those cells.

The electric field shaping may be regulated by the wiring of varying configurations of anodes and cathodes within the electrode array, in which case the electrodes may be of smaller physical dimensions (<1 mm length/circumference >20 μm length/circumference). For example, transformation of cells with DNA may be achieved in a vector in parallel with a linear array using alternating anode and cathode electrodes, while spherical shaped fields of transformed cells extending orthogonally to a linear array may be achieved by separating anodes and cathodes and passing current locally between the ganged electrodes.

In an embodiment the EGD-P device consists of several electrodes (two or more), in either a linear, 2D or 3D structure. An example of a two dimensional array and modelled electrical field is shown in FIG. 16.

In an embodiment, the electrode array is created from conductive hydrogel materials, separated by areas of low conductance (insulators). The conductive hydrogels can be manufactured on a metal (typically platinum) substrate that has been coated with a layer of conductive polymer and then grown into the hydrogel to create an interpenetrating network. However, other hydrogel embodiments are also contemplated within the scope of the present invention. The conductive nodes have electrical continuity such as to focus electric fields about positions within the array when an electrical potential is provided to the nodes, which are driven together (ganged) to produce a local current return to multiple nodes simultaneously.

In an embodiment the probe may be manufactured with particular configurations of coupling of the array of electrodes so that the gene delivery is tailored to a target field of cells within tissues. For example, linear arrays as discussed above may be formed using insulated wires with gaps in the insulation for the electrodes. In other embodiments electrodes may be printed or grown on a substrate to have a given configuration for a target field shape. In other embodiments electrodes may be formed using networks of wires, insulated, exposed and interconnected in configuration designed to achieve target electric field shape and gradients.

Alternatively, the array may be configurable, for example in an embodiment each electrode may be selectively driven and sets of two or more electrodes ganged together to be driven commonly as anode or cathode to achieve the desired electric field shaping. In an embodiment this can be achieved by electrically connecting the ganged electrodes to be commonly driven as an anode or cathode, alternately each electrode may be individually selectively driven. Causing electrodes to be ganged together may be achieved by physical means, for example by physically connecting electrode wires manually or using a plug-in interface to provide interconnection between electrodes. For example, different reusable interconnection modules may be provided for interconnection between the pulse generator and probe to reconfigure the array by interconnecting different sets of electrodes to achieve different field shapes. This may allow an embodiment where a generic disposable probe comprising the electrode array can be driven using different anode and cathode configurations (ganging) using different interconnection modules/boards between the probe and pulse generator.

Alternatively a configuration module may be provided to allow ganging of electrodes to be configurable under control of a controller, for example the configuration module may operate like a switchboard selectively connecting electrodes as anodes or cathodes. In a simple hardware embodiment this may be a series of manually operable switches, one for each electrode. In another hardware embodiment a set of electronically controllable solid state switches may be used, and this embodiment can enable configuration control by a software based controller. In an embodiment the array may be configurable by a controller which selectively controls polarity and pulses applied to the electrodes in the array to control the generated electric field. Further details of the controller are described below.

Figure 40:
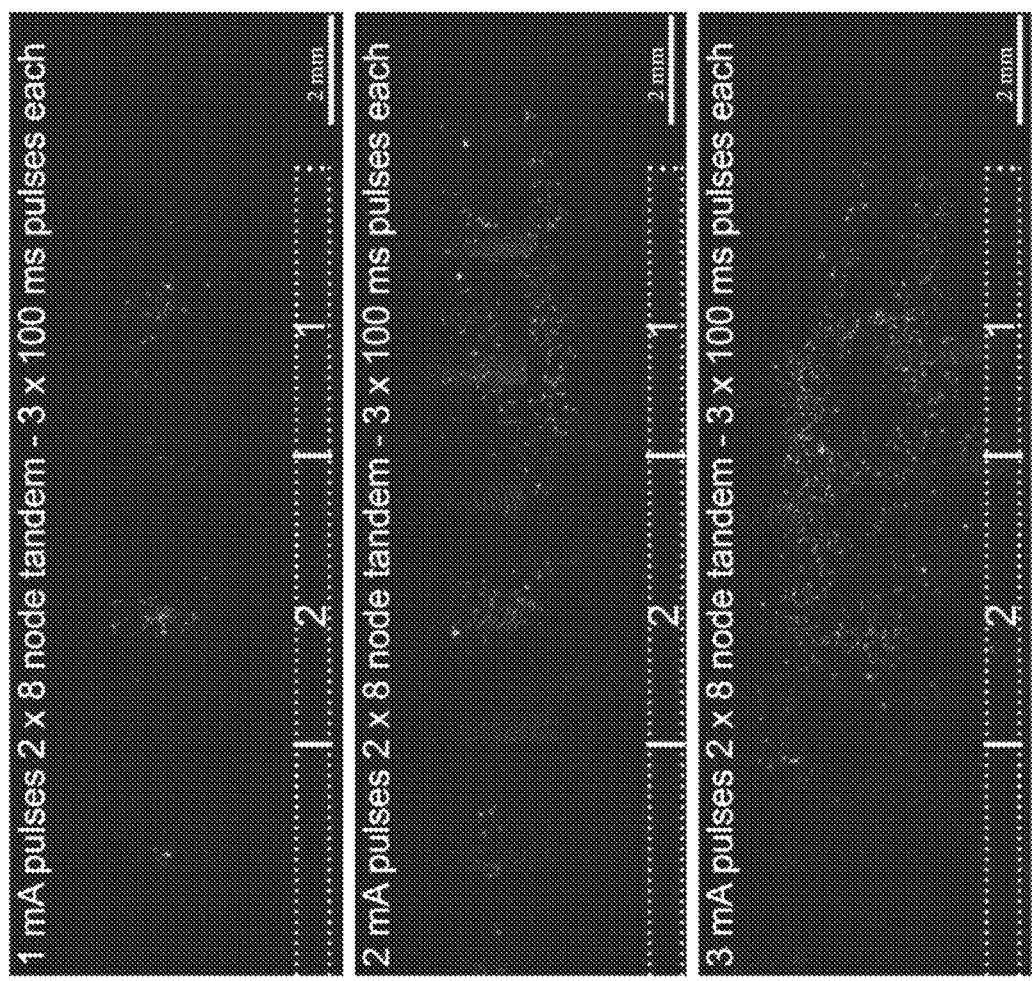
FIG. 40 shows enablement of distributed gene electrotransfer via a gene delivery platform with switchable array configuration, using constant current pulses and sucrose-based carrier solution in HEK293 cell monolayers in vitro.

The set of images in FIG. 40 show enablement of distributed gene electrotransfer via a gene delivery platform with switchable array configuration, using constant current pulses and sucrose-based carrier solution in HEK293 cell monolayers in vitro. Using a progression of current pulses along the array, GFP reporter gene delivery was distributed along the length of the array using the tandem array configuration for focusing an electric field between electrodes 1-4 (anodes) and 5-8 (cathodes). After 3×100 ms×1 mA current pulses were delivered to electrodes 1-8 (or for other studies 2 mA or 3 mA pulses), a switch box was used to shift the active array to a second field position, (electrodes 9-12 for anodes and 13-16 for ganged cathodes) and the particular current pulse protocol was repeated. This produced an extended region of transduced HEK293 cells imaged for GFP fluorescence after fixation at day four. HEK293 cell monolayers were exposed to μCBA-eGFP plasmid (2 μg/μl) and gene electrotransfer utilized 10% sucrose carrier solution. In the examples shown in FIG. 40 the first 3 current pulses (3×100 ms) were delivered to the apical most 8 electrodes (1; where the outline of the array is shown at the bottom of each image so as not to mask the region of transfected GFP positive HEK293 cells) and then a second series of pulses of the same profile were delivered to the adjacent (more basal) 8 electrodes. Tandem array configuration, four adjacent ganged anodes and four adjacent ganged cathodes. The current pulses were 1 mA (Vappl=15 V), 2 mA (Vappl=25 V) or 3 mA (Vappl=35 V) as shown. 10% sucrose carrier; Digitimer DS5 constant current stimulator for current pulse delivery. Imaged at 48 hour post gene electrotransfer. These results demonstrate utilisation of the configurable array to treat a predictable, targeted, region of tissue.

In other embodiments the electric field shaping may be regulated by steering some current to a separate electrode or electrodes, at a distance outside of the electric field that is effective for electroporation-mediated DNA delivery—either completely separate from the array, or at a distance from electrodes activated in the array which are used to define the target gene delivery field (regulated by the gene delivery controller).

Delivery of Therapeutic Molecules, Agent or DNA

The probe may include DNA delivery capability, for example as a coating, by elution from an integrated matrix, or delivery via microfluidics chambering.

In an embodiment the probe is non-implantable this enables embodiments of the probe to also be used for delivery of the therapeutic agent, molecules or DNA. For example, the EGD-P may include packaged DNA which will be released into the target tissue area prior to passing of current between the electrodes to achieve gene delivery. The gene delivery probe may have DNA or molecular delivery capability via integrated fluid chambers (incl. microfluidics pathways, or a cannula) for delivery of therapeutic solutions. The means of DNA delivery may be by direct injection, an embedded cannula within the probe with one or many orifices, microfluidics, or by diffusion (passive or electrically-gated) via the material, for example but not limited to a hydrogel matrix, which is integral to the EGD-P, or by thermal expansion. While multiple drug deliveries from the probe may permit multiple electroporation gene delivery actions within a single procedure, the probe is a non-implantable, single procedure device, effectively a consumable under good manufacturing practice (GMP) certification, preloaded with the therapeutic DNA or RNA gene cassette. When used for gene delivery as an adjunct to an implantable bionics interface, the EGD-P may be smaller in physical dimensions than the implantable electrode array. It is envisaged that the EGD-P will be manufactured for scalable, production with composite materials such as hydrogels and conductive polymer materials, rather than including platinum electrodes used in conventional implanted bionics interfaces. Where the therapeutic delivery means is a hydrogel matrix or coating the carrier material may be chosen to induce target electric field response, similarly to the methodology discussed in relation to carrier solutions above. For example a hydrogel matrix composition may influence the resistivity in the region of the array as the therapeutic agent is released and treatment performed, this material composition providing a controllable variable when determining treatment parameters.

Some probe embodiments can be configured to have more than one agent delivery structure. For example, two cannulas to allow controlled separate delivery of two different drugs, or a combination of a cannula and other drug delivery method i.e. complementary drug eluting coating. Any combination of agent delivery mechanisms is envisaged within the scope of the invention. It should be appreciated that more than one fluid or pharmaceutical delivery mechanism may be provided in the physical device and such structures are not limited to use for only gene therapy agents. For example, other chemicals may be supplied via the delivery mechanism than gene therapy agents. For example, complementary treatment drugs or antibiotics may be delivered via the probe supplementary to the electroporation treatment. In some instances carrier solutions, in particular utilising saccharose carrier solutions without the presence of DNA or other therapeutic agents can provide positive effects on electric field shaping and intensity, therefore in some treatments it may be desirable to deliver a saccharose solution only to achieve target electric field stimulation, independently of any therapeutic agent to delivery. A delivery system controller may be configured to control sequences for delivery of two or more agents or other chemicals/solutions, of which two or more may be delivered concurrently or sequentially. The drug/fluid delivery sequence may be synchronised with a pulse delivery sequence.

It is envisaged that embodiments of the invention may utilise implantable probes. For example an implantable probe may be utilised for a course of gene therapy treatment over a period of time, say several months, and to minimise physical trauma an implantable probe is implanted once for use multiple times during the course of treatment, for example several months or years, then optionally removed. The implantable probe may include the therapeutic agent, for example in a coating or electrically stimulable release mechanism, be configured for connection to a therapeutic agent delivery mechanism. Alternatively implants, for example cochlear implants, may be modified to operate as an electroporation probe in addition to the normal operation of the implant. The implant may be configured to operate only temporarily as a gene delivery probe and permanently in accordance with the implant's primary function. For example, therapeutic agent delivery capability may be added to an implantable device such as by including a cannula that may be temporarily connected to a therapeutic delivery line or by incorporating the therapeutic agent into an electrically stimulable microfluidics release mechanism. The implant may be controlled to switch from regular operation to a gene therapy mode temporarily to provide treatment then resume regular function. In implant embodiments the therapeutic agent carrier solution may be chosen to enable utilisation of low amplitude electroporation pulses to minimise power consumption and/or avoid overloading implant electrodes designed for the primary function when driving the electrodes for gene therapy.

The gene delivery probe may include materials that enable controlled or uncontrolled release of embedded or coated therapeutic molecules. In one embodiment, the gene delivery probe may be assembled as a sheet of insulating material where embedded electrodes in an array are wrapped around a cannula for DNA delivery. The cannula for DNA delivery may be generally porous along the length and the wrapping of the sheet of electrodes (the array) may be porous, to permit delivery of the solution from the central cannula.

The sheet array with or without the cannula may be scalable, with repeated electroporation units typically comprising electrodes configured to transform volumes of tissue extending no more than 5 mm from the surface of the electrodes.

In an embodiment the probe may include a fluid channel such as a cannula or microfluidics to enable movement of the therapeutic (such as DNA) through the device to the space around the device, prior to the electroporation-mediated delivery of the therapeutic molecules across the cell membrane. This may permit multiple iterations of drug delivery and electroporation, or delivery of multiple separated therapeutic agents at various locations, a location being a target field of cells receiving the agent by transient electroporation. In an embodiment the probe includes a delivery actuator operable by a controller to enable the therapeutic agent delivery to be controlled automatically by a controller. For example, this can allow a coordinated sequence of agent delivery and electroporation pulses to be programmed into a controller for automatic execution. It should be appreciated that automated control of both agent delivery and electroporation can provide more precise control and optimisation of treatment. This also allows a trained technician to prepare the required program in consultation with the specialist/surgeon prior to treatment and the treatment performed under automatic control once the specialist/surgeon places the probe in the biological tissue.

In an alternative embodiment the probe may include the therapeutic molecule encapsulated within the material of the device, such that the elution profile of the therapeutic molecule from the interface material is designed to ensure rapid equilibration of the therapeutic molecule within the target field of cells prior to the electroporation. This may include use of hydrogel matrix whose molecular constitution is matched to produce a desired elution rate relative to the diffusion properties of the therapeutic molecular (typically size and charge dependent). In some such embodiments placement of the probe in the biological tissue can trigger the release of the molecules.

Alternatively or additionally release of the molecules may be stimulated by activation of the electrodes. For example, in an embodiment the device may include gated drug delivery, where the therapeutic is retained or released from the matrix material (such as a hydrogel) by a continuous electrical bias potential. Activation of the electrodes to stimulate release of the molecules may utilise a lower power signal (current or voltage controlled) than the electroporation pulse, the signal being sufficient to stimulate release of the molecules to the tissue but insufficient to cause any other biological effect. In the embodiment the molecule release signal and the electroporation pulses may be time sequenced to optimise clinical outcomes.

The probe can be designed as a consumable, to be used as a single-use drug delivery and electroporation probe and may include electrical recording capability to aid placement and timing of gene electrotransfer such as resistance measurements and electrophysiology measurements. The probe will ideally be made from hydrogel components or material which permit robotic fabrication where conductive elements (electrodes) are typically less than 500 $\mu m^3$ in size, and ideally the physical size of the interface occupies less volume than the conventional implantable bionic electrode arrays (such as cochlear implants) which may be implanted into the field after the use of this gene/drug delivery device. Thus, manufacture of the EGD-P will involve scalable array production that is automated, rather than being reliant upon use of conventional electrode materials (e.g. platinum), and manual assembly/wiring. Typically, a hydrogel backbone such as PVA/HEP (heparin) will be bonded to a stratified composite material and conducting polymers such as Poly (3,4-ethylenedioxythiophene) (PEDOT), will be doped within the structure and at the surface (as the electrode nodes).

Controller

Embodiments of the electroporation system can be simple as shown in FIG. 1 having a probe 110 and pulse generator 120, which can be manually controlled or even configured to provide a fixed pulse sequence. For example, a system designed for a dedicated clinical application, where the same parameters are used for all patients, the pulse generator may be configured to deliver a set sequence of pulses. Thus, for each patient a new disposable probe is connected to the pulse generator, inserted into the target tissue, the generator activated to provide the target pulses, the probe removed and discarded. Such a simple embodiment may be applicable for routine commonplace treatments, for example such a treatment may be developed applicable for a routine dermatology treatment.

However, it is envisaged by the inventors that the system may be applicable for many different types of treatments, particularly gene therapy treatments, where customisation of treatment and a high degree of control is desirable. As discussed above, embodiments of the system can include a controller configured to control pulse generation and in some embodiments agent delivery. Embodiments may also provide for the currents passed or voltages applied being time multiplexed so a series of electroporation events may be generated over a short period of time at various sites along the array.

The controller may also be enabled to control array configuration. A controller can be included in the system to facilitate setting and control of the parameters required to produce the desired electric field. In an embodiment the controller may comprise the pulse generator and be configured to provide delivery of electrical current to the gene delivery probe. Both current-controlled and voltage-controlled modes are envisaged for different controller embodiments or and embodiment enabled to selectively operate in voltage controlled mode or current controlled mode. The controller may supply current to pre-configured electrode configurations of anodes and cathodes within the gene delivery probe, or the electrode configuration within the array can be switched manually or via the controller.

The controller incorporating the pulse generator is able to provide voltages to the array electrodes sufficient to achieve the prescribed electric field gradients around the gene delivery probe. The controller may also include control of therapeutic molecule delivery. The controller may be configured to adjust the parameter for the pulse generator based on the carrier solution of the therapeutic agent. For example the carrier solution type may be input to the controller by the operator. Alternatively the controller may be configured to adjust treatment pulse parameters based on a determination of carrier solution properties, for example via a chemical sensor of a therapeutic delivery module or measurement of operating characteristics. In an embodiment the controller may be configured to measure the operating characteristics with the probe placed with the treatment environment (in vivo or in vitro). In an embodiment the controller may be configured to perform a pre-treatment test to determine the apparent resistivity of the array and carrier solution in vivo to predict voltage once electroporation pules are applied. For example, the controller may trigger the pulse generator to generate a short duration low amplitude pulse of known current or voltage and based on measured voltage and current characteristics determine the apparent resistivity. The apparent resistivity may be influenced by the therapeutic agent solution composition, amount of therapeutic agent solution (such as DNA concentration and carrier) surrounding the array, permeability of the tissue surrounding the array to the therapeutic solution and characteristic of the tissue. In some embodiments a carrier solution only (for example a saccharose-based carrier solution without DNA or other therapeutic) may be supplied to locally alter the in vivo electrical characteristics of the tissue for treatment to lower the charge required to achieve desired electroporation outcomes. The controller may be configured to automatically adjust treatment pulse parameters if the measured resistivity characteristics fall outside a tolerance range for the treatment. For example, in the instance of higher than expected resistivity the controller may reduce the driving pulse current amplitude for a controlled current source pulse generator. If the resistance is lower than expected, then the driving pulse amplitude may be increase accordingly. The aim of this adjustment to is to drive the array during the treatment phase to achieve the target electrical field characteristics required to achieve the treatment outcomes. The resistivity measurement may also be used to trigger the electroporation pulse sequence, for example the resistivity may be monitored to determine when an appropriate amount of therapeutic agent solution (and optionally additional carrier solution) is delivered for treatment to commence—i.e. when resistivity of the array reached a threshold value or ceases to change indicating saturation. Thus, feedback from measuring array resistivity pre-treatment may enable improved reliability of treatment outcomes.

A block diagram of a system embodiment including a controller is shown in FIG. 15, the system 1500 comprises the probe and electrode 1510 as described above and a controller 1530. In this block diagram the controller is shown including the pulse generator 1520 however the pulse generator may be a separate piece of equipment. The illustrated embodiment also includes optional features such as a configuration module 1540 to enable control of the array configuration as discussed above; an agent delivery module 1550 to control delivery of the therapeutic agent via the probe; a user interface 1560; and memory 1570 for storing data such as treatment parameters 1580 and treatment logs 1590.

In an embodiment the controller is implemented using a computer system which may comprise the full functionality of the system, or control dedicated hardware components via data connections. Any possible configuration of controller hardware, firmware and software is envisaged within the scope of the invention. In an embodiment the controller functionality may be implemented using a dedicated hardware device, for example a version of a pulse generator modified to provide controller functionality or dedicated hardware device say including hardware logic ASIC (application specific integrated circuit) or FPGA (field programmable gate array), firmware and software implementing the controller functionality. An advantage of a dedicated system can be independence from commercial software platforms and operating systems, this may be advantageous in obtaining regulatory approval and constraining use of the system to the intended purpose. However, a disadvantage of this embodiment may be increased system development and ongoing maintenance costs, and lack of flexibility to take advantage of new technologies or developments in the technical field.

Alternatively, the controller functionality may be provided as a software program executable on a computer system, such as a personal computer, server or tablet, and configured to provide control instructions to an independent pulse generator and other optional hardware such as an agent delivery actuator. A software based controller embodiment executable using commercially available computer hardware is envisaged to provide a specialist with a user interface 1560 to input parameters for the electroporation treatment 1580 that are then stored in memory 1570 for use to drive the pulse generator 1520 and optionally configuration module 1540 and agent delivery module during electroporation treatment delivery 1550. In an embodiment this may comprise the controller analysing a target treatment region parameters and carrier solution parameters; determining appropriate electrode array configuration(s); and defining at least one sequence of pulses calculated based on the relationships discussed above to achieve the target treatment field for each appropriate array configuration. In embodiments where agent delivery is controllable by the controller the controller may also calculate and define agent delivery actuation in the treatment pulse sequence. In embodiments where the array configuration is controllable by the controller the controller also defines the array configuration for implementation by the configuration module. In embodiments where the array configuration is dependent upon selection of fixed array configurations, either a selected probe array configuration may be input to the controller by the specialist/surgeon/clinician or the controller may output probe selection recommendations. If more than one combination of array and pulse sequence is determined to be appropriate to satisfy the treatment requirements the possible combinations may be output to the surgeon/specialist/clinician for selection.

Some embodiments of the controller may provide software to model the treatment. In some embodiments data utilised for modelling may include patient imaging data (i.e. MRI or CT scans) to enable modelled treatment fields to be considered in conjunction with patient data. Modelling data can also include options for therapeutic agent carrier solutions. For example to determine viable or optimal carrier solution parameters to safely achieve desired treatment outcomes via modelling. Alternatively where a limited number of carrier solution options are available, to model potential outcomes for each option to facilitate decision making by the specialist/surgeon/clinician.

It should be appreciated that system functionality provided associated with planning treatment may be complex and utilise sophisticated software models to determine the required data to drive the physical treatment apparatus. But the actual data required to physically execute the treatment can be quite simple—a defined array configuration (which may even be a fixed array), a sequence of timed pulses and optionally signals for controlling agent delivery for the chosen agent solution. Thus, the controller may simply output the sequence data for driving the physical treatment equipment.

Embodiments of the pulse generator 1520 can operate under voltage or current-driven modes. In an embodiment the pulse generator is a stand-alone independent unit having its own power supply independent of the controller. The pulse generator may be in data communication with the controller to enable the controller to program the pulse generator with the pulse sequence. Alternatively, the pulse sequence may be calculated by the controller and loaded into the pulse generator by manual programming or data transfer (for example by direct connection, wireless connection or via physical media such as a portable solid state memory device) and the pulse generator operated independently of the controller for therapy delivery. Isolation of the pulse generator from the controller may be a safety requirement for some systems, in particular enabling the disposable probes to be operated using pulse generators already approved and available for human clinical use. In some countries this may enable independent regulatory approval of the probes for use in conjunction with a selection of commercially available and regulatory approved pulse generators.

Additional Embodiments

In embodiments of the invention all, or the majority, of current is returned within the array. In some embodiments, current steerage may involve diversion of a minority of current to some remote external return electrode(s). Applicable to all the previous configurations described, additional distant return electrodes separate from the array may be used to return a percentage of the applied current and thus change the localized shaping of the electric field and the resultant transformed field of cells. This enables current paths to be dynamically controlled using local (close-field) and far-field balancing technology or by a combination of both—informed by modelling and in vitro and in vivo testing. The current path will be predominantly returned within the electrodes of the array. Current steering may be included via an external controller and circuitry that regulates some external current spread.

Figure 20:
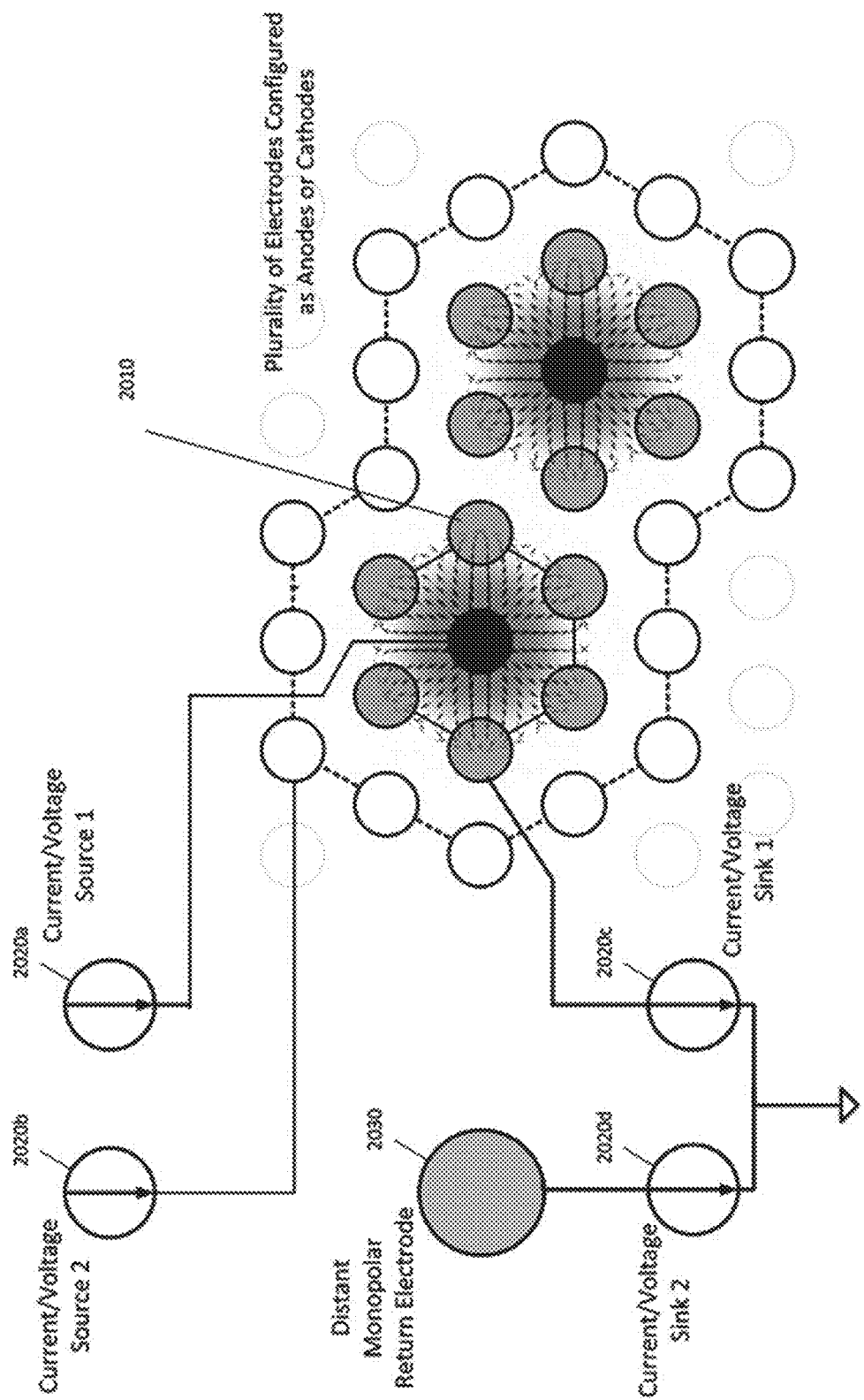
FIG. 20 shows a schematic for quasi-monopolar control of current steering for electric field focusing with 2D electrode arrays.

FIG. 20 shows a schematic for quasi-monopolar control of current steering for electric field focusing with 2D electrode arrays 2010 shown as illustration. Current sources and sinks 2020a-d provide control of the proportion of current diverted from the 2D electrode array to one or more monopolar return electrodes 2030 that are distant to the target cell transduction field.

Figure 21:
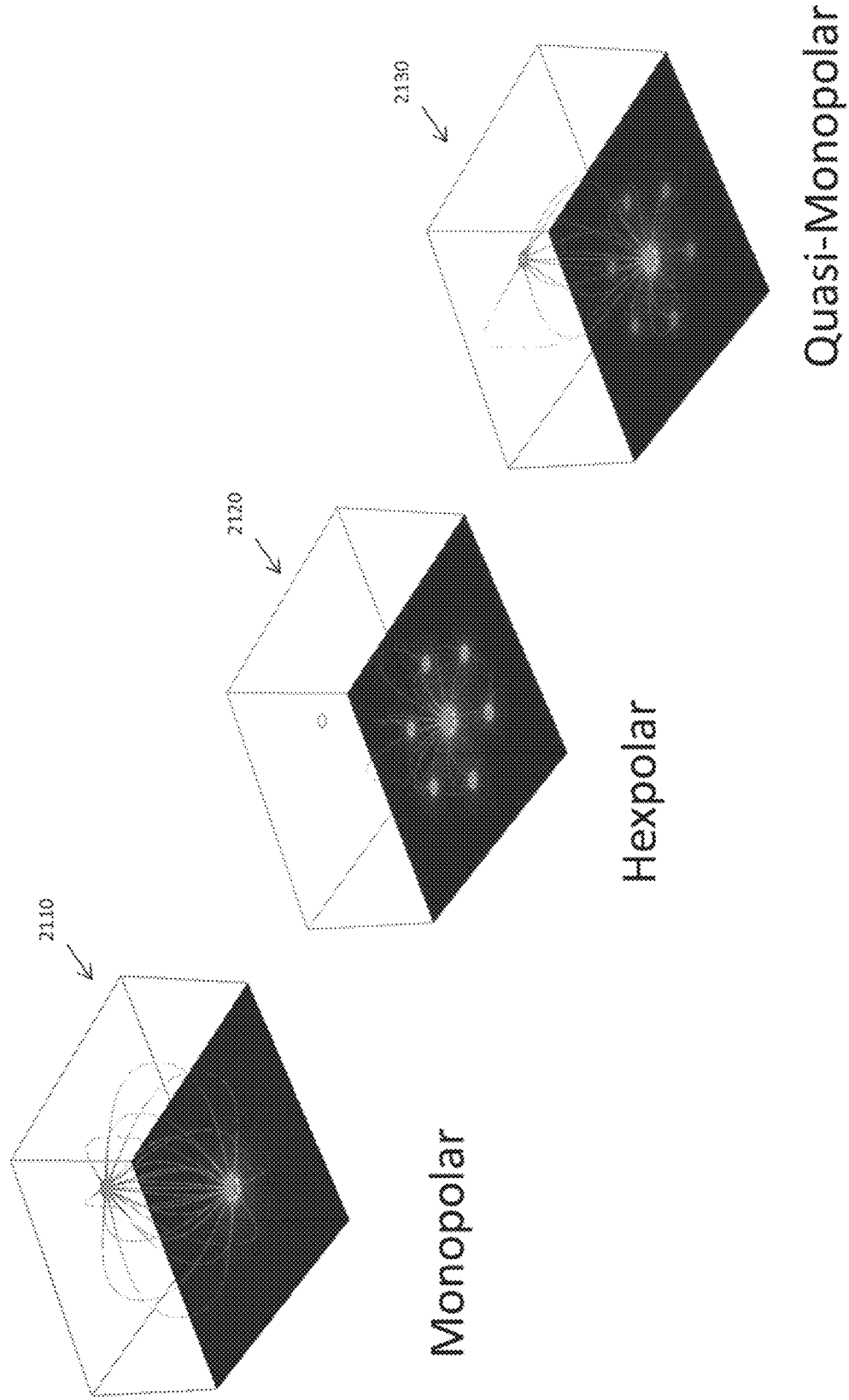
FIG. 21 illustrates examples of current steering dependent upon electrode configuration within arrays.

FIG. 21 illustrates examples of current steering dependent upon electrode configuration within arrays. Monopolar 2110 reflects conventional open-field current paths, while hexapolar 2120 and quasi-monopolar 2130 configurations provide electric field focusing associated with arrays of electrodes that are contiguous, with the target cell population not intervening within the primary electrode array structure. In the case of quasi-monopolar current steering 2130, a minority of the current is diverted to an electrode distal to the contiguous electrode array.

Figure 22:
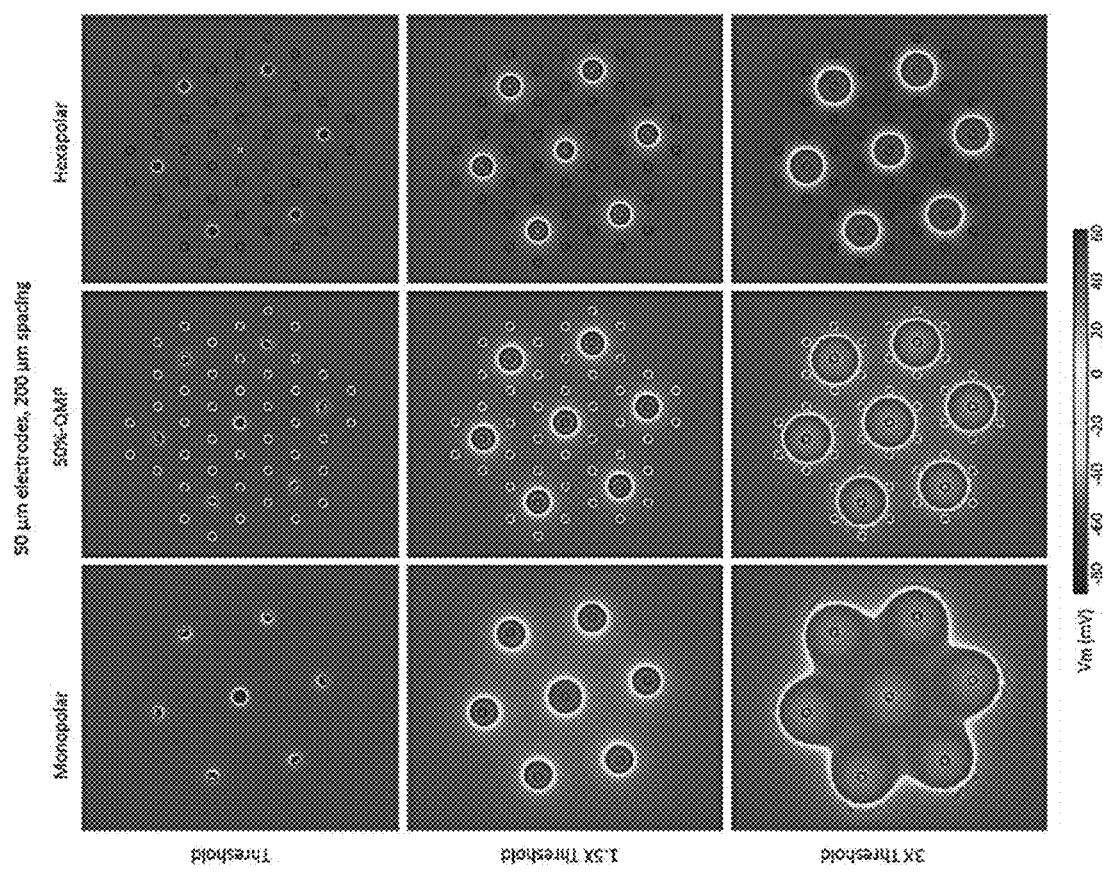
FIG. 22 illustrates examples of stimulation strategies of titrated electric field focusing including monopolar return of current to contiguous electrodes within an array.

FIG. 22 illustrates examples of stimulation strategies of titrated electric field focusing including monopolar return of current to contiguous electrodes within an array, shown in FIG. 22 as a central return electrode surrounded by a hexagonal array of current source electrodes (anodes). QMP—quasi-monopolar current control includes controlled shunting to electrodes distal to the field of cells targeted for transduction. The Hexapolar configuration models distributed current spread within a scalable array.

In an embodiment the probe may have electrode channels which are switchable so that some channels may be used for transient electrical stimulation and other channels used from recording via isolated instruments for the purpose of functionally directed positioning of the device (such as recording from brain regions in the case of CNS delivery—a procedure commonly utilised for location of implantable deep brain stimulation electrode arrays). The device may be configured between stimulus/recording probe and close-field electroporation mode multiple times within one procedure.

Prototype Example and Test Results

Figure 17A:
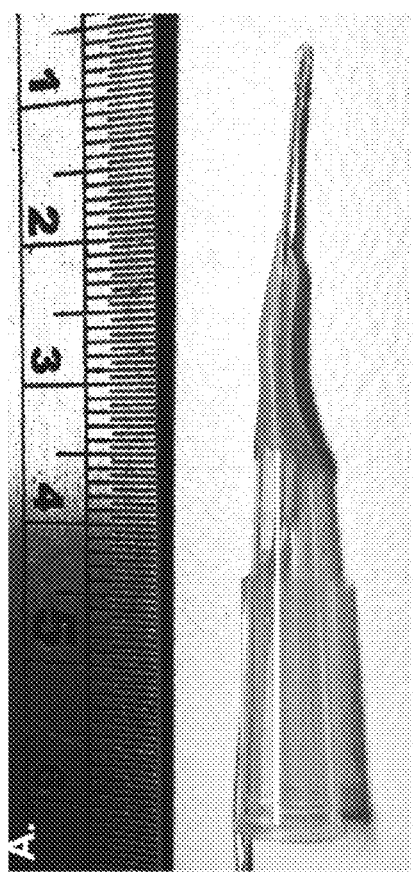
FIGS. 17a-c show details of a prototype probe.
Figure 17B:
Figure 17C:
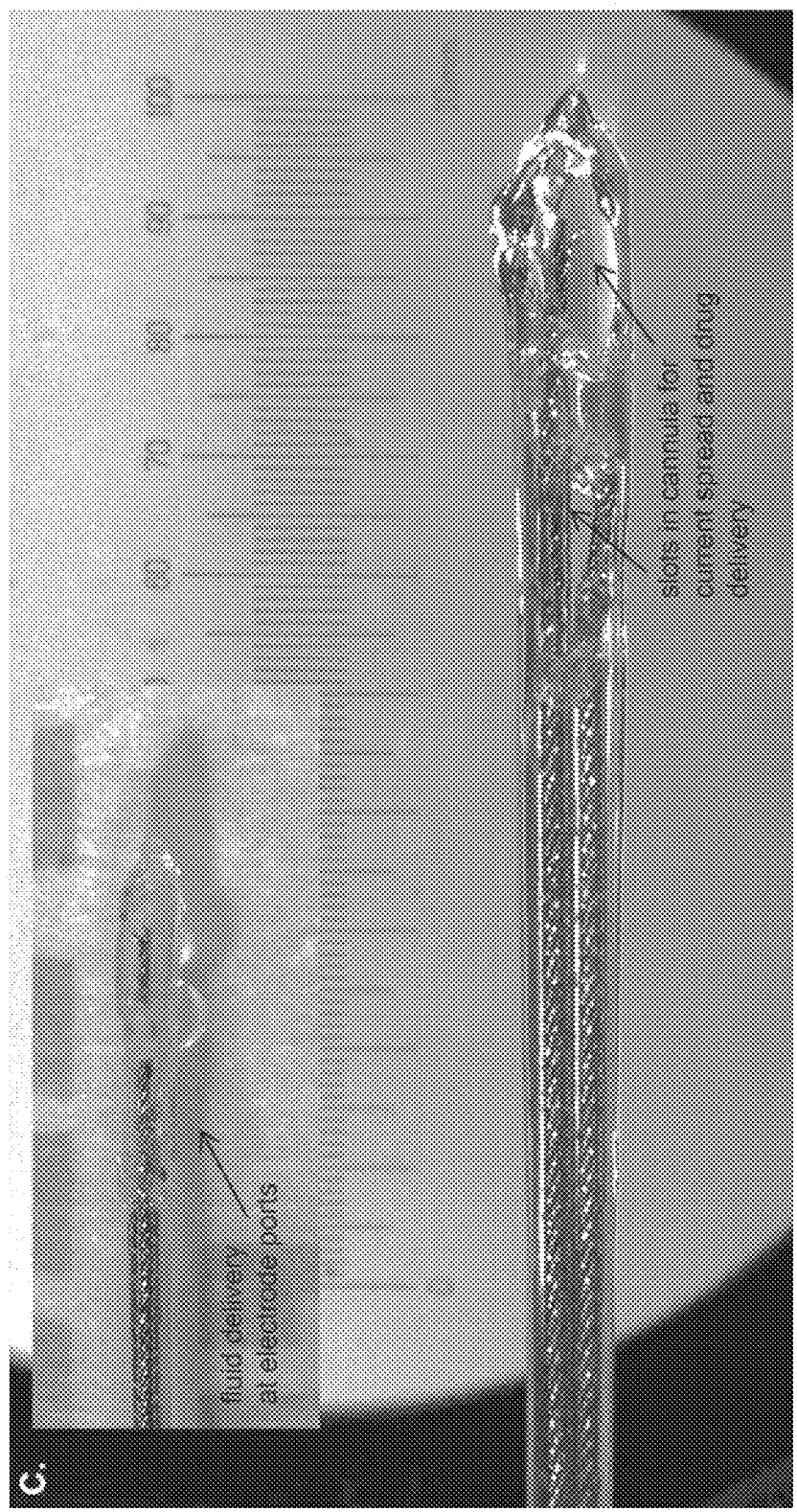

Details of a prototype probe are shown in FIGS. 17a to 17c. The prototype comprises two insulated wires ensheathed in a cannula. Slots are formed in the cannula in the regions where the wire insulation is removed to form electrodes to allow fluid delivery and current spread. In this prototype each wire has a different polarity so the electrodes formed on one wire act as cathodes and the electrodes formed on the other wire as anodes. Test results using the prototype are shown in FIG. 18.

Figure 18:
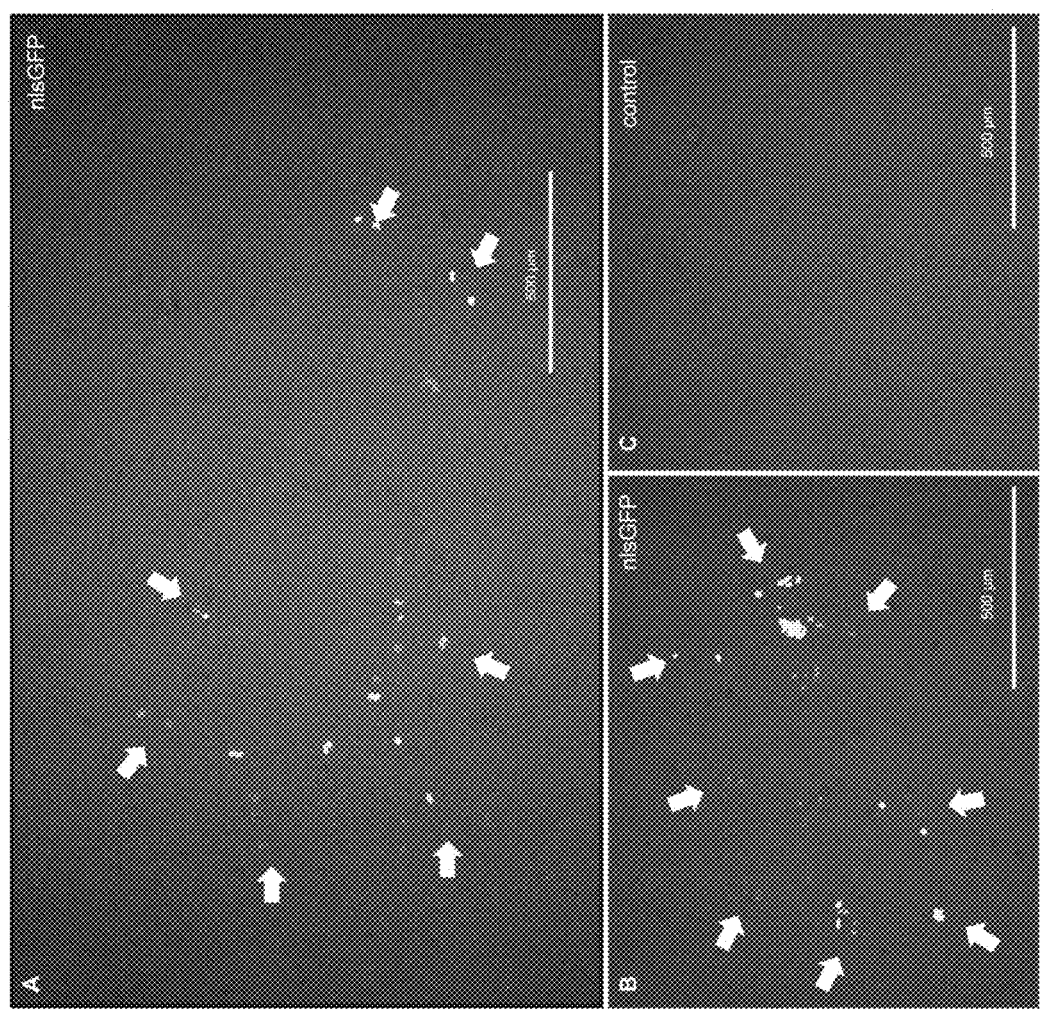
FIG. 18 shows enablement of electroporation gene delivery using the prototype probe of FIG. 17a-c.

FIG. 18 shows enablement of close-field electroporation gene delivery using the prototype cannula-ensheathed linear bipolar electrode configuration shown in FIGS. 17a to 17c. This is evident form nuclear localised green fluorescence protein (nlsGFP) signal in a field of human embryonic kidney (HEK293) cells growing as a monolayer on a coverslip. A&B of FIG. 18 show examples where electrical pulse parameters were: 2×100 ms pulses at 20V. Naked DNA plasmid (CMVp-BDNFx3FLAG-IRES-nlsGFP) in saline carrier solution was applied to the cells as 2 µg/µl, (20 µl) and the gene delivery probe was positioned just above the cell layer. The fields of transduced cells span approximately 2 mm$^2$ (arrows). C of FIG. 18 shows the control (DNA applied to cells with gene delivery probe in position, but no electrical pulses were applied to the probe. Cell culture for 48 hours after DNA delivery. Imaged at 488 nm excitation using confocal LSM.

Figure 19:
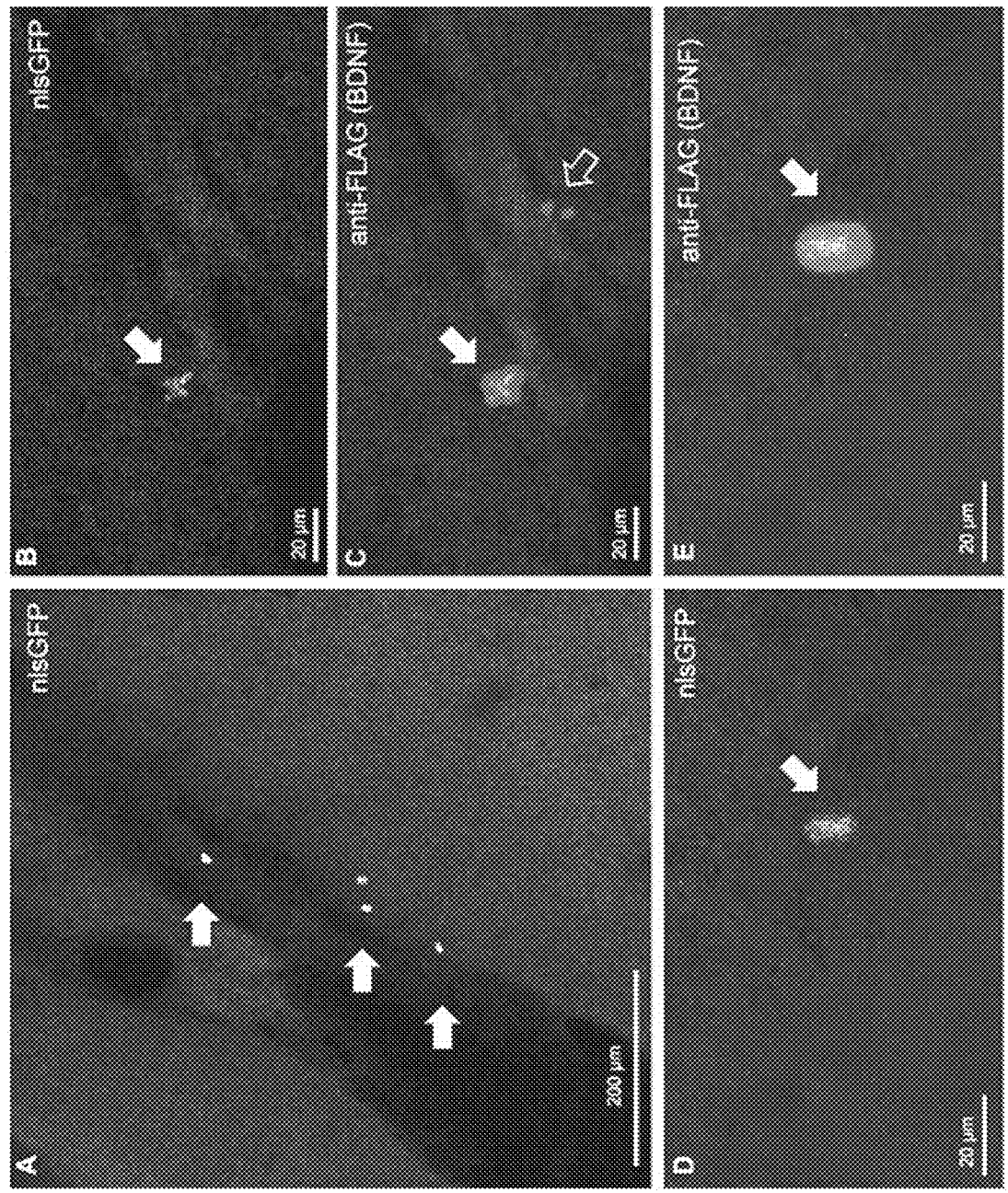
FIG. 19 shows enablement of electroporation gene delivery in guinea-pig CNS using a tandem configuration linear electrode array.

FIG. 19 shows enablement of targeted electroporation gene delivery in guinea-pig CNS using a tandem configuration linear electrode array. A shows a cerebellar cortex cryosection (50 µm) showing nuclear localised green fluorescence protein (nlsGFP) in four neurons (488 nm excitation confocal greyscale image). B&C of FIG. 19 show double labelling of neurons expressing nlsGFP and recombinant brain-derived neurotrophic factor (BDNF-3xFLAG) using immunofluorescence against the FLAG tag. Filled arrows indicate the GFP and BDNF expressing cells—open arrow indicates 2 additional neurons expressing BDNF but with undetectable nlsGFP signal (C has both green and red channels). The vermis region of the cerebellar cortex was given a bolus injection of 10 µl of a naked cDNA plasmid (2 µg/µl) with gene cassette (CMVp-BDNFx3FLAG-IRES-nlsGFP) over approximately 10 seconds and the 8 electrode array was then inserted 5 mm into the injection track and electroporation was performed using the tandem electrode configuration (2×100 ms 15V pulses, 900 ms separation); 3 days survival. D&E of FIG. 19 show nlsGFP (green fluorescence) and overlaid BDNF (anti-FLAG primary antibody with Alexa 594 nm excitation secondary antibody providing red immunofluorescence signal) expression respectively for a neuron within the periaqueductal gray region of the guineapig midbrain following electroporation gene delivery (50 µm cryosection). In this experiment, the plasmid DNA (2 µg/µl) was infused (10 µl, 500 nl/min) 7 mm into the midbrain via the inferior colliculus, using a Microdrive via 27G needle under stereotaxic control. The electroporation was then performed by withdrawing the DNA injection needle and inserting the electrode array as for A-C. The electrode array consisted of a line of eight 350 µm diameter platinum rings with 300 µm separation; with four adjacent electrodes ganged as anodes and the other four ganged as cathodes 2×100 ms pulses at 15 V.

As shown in the above test results embodiments of the present invention can provide predictable gene delivery results. The invention provides a new class of medical device that serves within an intended clinical application of being a disposable single use interface for generating focused electric fields for the purpose of targeted electroporation of cells within biological tissues. The application of electric field shaping electroporation is a new class of gene delivery platform around 'dial-up' control of where and how many cells are transformed with an expression cassette.

Embodiments of the system enables acute 'dial-up' localized gene delivery to small (strategic) groups of cells within a tissue—such as the cells lining the cochlea, or groups of neurons in a prescribed region of the brain. In some embodiments this interface is a single-use device which is non-implantable, and is powered by an external connection to an isolated power supply. The interface includes DNA solution delivery capability, such as microfluidics channels, or by diffusion from a hydrogel or other elution matrix, or by coating.

An advantage of this electroporation system is that the probe is a non-implantable device which may be used to complement implantable bionics, e.g. cochlear implants and brain implants such as the Deep Brain Stimulus electrode arrays; or may act as an acute treatment device, which delivers independent directed gene delivery to a target tissue; or may provide directed delivery of other therapeutic molecules, where delivery involves controlled transient permeabilization of a local field of cells as the drug delivery target.

In some embodiments the electroporation probe is non-implantable, rather it is inserted into the target field for acute delivery of the target molecules via a discontinuous electrical pulse train. This allows greater flexibility in the materials and types of construction used for the probes as these are not required to withstand chronic or repeated use. Further, the probes need not meet regulatory or long-term safety and efficacy requirements for implants.

The aim is to achieve "dial-up" control of the volume of transduced tissue around scalable arrays for directed molecular delivery as a single-use consumable which is an adjunct to bionics implant procedures, and also as a stand-alone treatment, such as localized gene therapy for CNS disorders.

The electrodes can typically be produced from conductive polymers and the physical properties of the interface are such that it can match the physical configuration required for insertion into the target tissue or organ.

The array is not designed to be implantable; as such, rather than the platinum electrodes typically used in bionic arrays, in the EGD-P device, construction materials of preference may be hydrogels, conductive and non-conductive polymers and composites. The probe can be scalable in size and electrode layout (linear, 2D or 3D) and the electrodes are connected and driven (ganged) together in fixed configurations in the array, or externally ganged by an associated controller and driver, to flexibly focus the local electric field.

'Close-field' electroporation provides controllable targeting of gene delivery using naked DNA which is not achievable with other processes. For example, the spatiotemporal control of gene delivery achievable with this micro domain array-based electroporation may offer a refinement of possible viral vector-based treatment of Parkinson's disease by gene therapy targeting neurochemical modulation of the subthalamic nucleus with a glutamic acid decarboxylase (GAD65) DNA construct. Electroporation of naked DNA gene cassettes also has clear advantages over other gene delivery technologies due to the lack of inflammatory responses compared with lipofection or viral vectors, particularly adenovirus, and because the size of the plasmid DNA 379 cassettes is relatively unconstrained.

Embodiments of the present invention may be utilised to induce controlled cell transformation with naked DNA—with 'dial-up' predictability in localized gene delivery and consequent expression of the gene construct being achieved. This control of the site and extent of gene expression are key elements in safe and effective gene therapy approaches for treatments of brain disorders in particular, where therapeutic action is required at specific sites.

It will be understood to persons skilled in the art of the invention that many modifications may be made without departing from the spirit and scope of the invention.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

EXAMPLE 1

In Vitro HEK293 Cell Monolayer Model

In this example the inventors showed efficient electroporation and DNA electrotransfer via an array of microelectrodes, such as a cochlear implant array, when used in conjunction with the sucrose carrier. The sucrose carrier (10%, pH adjusted to 7.3) for a plasmid DNA encoding a GFP reporter (at ~2 µg/µl) was applied to coverslips supporting a monolayer of HEK293 cells. Measurement of the voltage generated at the electrodes due to distribution of current across ganged electrodes in the array was increased by a factor of 10 for a given current, relative to the use of physiological saline solutions (TRIS buffered saline and normal saline (0.9% NaCl). This resulted in high efficiency localized gene electrotransfer of a plasmid encoding a GFP reporter, detected by fluorescence microscopy from 18 hours post electroporation. In contrast, the saline carrier groups exhibited negligible electrotransfer at comparable current levels. When electroporation was undertaken using constant voltage, there also a significant advantage in using the sucrose carrier in that the current required to achieve the set voltage was reduced.

This invention is significant with regard to minimising the current required to obtain efficient gene delivery using bionic arrays, as the gene electrotransfer is highly dependent upon the local field strength in the neighbourhood of the electrode array and use of constant current with sucrose carrier, rather than constant voltage, will enable the greatest gene delivery efficiency for the least charge delivery and hence minimises potential toxicity. Reduction in current required for each electrical pulse under this current-regulated configuration equates to a direct reduction in toxic products arising from the electrochemical interactions of the media with water when the Faradaic capacity of the (platinum) electrodes is exceeded. This includes electrolytic actions at the electrode surface that result in breakdown of water into oxygen and hydrogen, as well as production of other toxic agents due to redox reactions, and also direct caloric effects.

Other considerations of the use of sucrose as a carrier for DNA for electroporation and gene electrotransfer consider sucrose to be protective based on its relative immobility and hence buffering of osmotic stress in transiently ported cells under voltage regulated gene delivery. The differential effect of sucrose discovered here would be undetectable under the voltage-related mode without careful analysis of the current delivery. Whereas the critical factor for efficient gene transfer with bionic array-based close-field electroporation is the localised electric field strength. In this domain, sucrose carrier, utilised with current delivery, enables the necessary field strength for gene delivery at lower charge delivery. The bionic array for close-field gene electrotransfer referred to here consists of an array of two or more sub-millimetre electrodes with submillimetre spacing, wired together in coupled configurations to enable focusing of the electric field in close proximity to the array.

EXAMPLE 2

In Vivo Guinea Pig Cochlea DNA Electrotransfer Example

In this example, a cochleostomy was performed in the isoflurane anaesthetized guinea pig and a plasmid DNA solution coding a GFP reporter (2 µg/µl) was injected into the cochlea using 10% sucrose balanced to pH 7.3 as the carrier. The use of the sucrose carrier solution increased the resistance of the array by tenfold to ~8.5 kohms, from previously reported resistances ~850 ohms using a saline carrier solution. These results were achieved using an eight node bionic array wired in a 'tandem' configuration of 4 adjacent anodes ganged together and four adjacent cathodes ganged together. The gene electrotransfer was performed using a constant current protocol of 3×100 ms pulses at 1 mA. This generated an electrode voltage of ~12 volts, sufficient to establish expression of the GFP reporter by the mesenchymal cells lining scala media. In comparison, with normal saline (0.9%) as the carrier, the voltage achieved would have been 1.2 volts, which is below the reported threshold for gene delivery. Similarly, GFP expression was achieved using 2 mA applied current 6.65 kohm in a separate experiment, where a voltage of ~25 V was elicited. This compares with ~2.5 V should saline be used with this bionic array.

The invention claimed is:

1. An electroporation system comprising:
   an electroporation probe comprising a linear array of at least two contiguous electrodes, with each electrode formed in a longitudinal section along the electroporation probe, the electroporation probe being configured to be temporarily inserted into a biological tissue for electroporation treatment; and
   a pulse generator electrically connected to the electroporation probe and configured to drive the at least two electrodes of the electroporation probe as one or more anodes and one or more cathodes so as to have different anode and cathode regions spaced along the electroporation probe using a pulse sequence of one or more electric pulses to cause current transmission through the electroporation probe, the physical electrode array geometry in combination with the pulse sequence causing generation of a shaped non-uniform electric field having electric field gradients in a target region in the biological tissue proximate the probe electrodes, where for each anode and cathode region, a gap between the anode and cathode focuses electric fields generated by passing current between the anode and cathode such that the electric field induced in the biological tissue is of highest electric field strength orthogonal to the point between the anode and cathode, whereby the electrode array geometry controls non-uniformity by causing variation in electric field strength along the array to spatially target a treatment area in the biological tissue.

2. The electroporation system as claimed in claim 1, wherein the non-uniform electric field includes electric field gradients in a range of 50 µV/µm to 500 µV/µm.

3. The electroporation system as claimed in claim 1, wherein the electrodes are relatively elongate along a direction of contiguity, wherein for each electrode the electrode's circumference is less than the electrode's length.

4. The electroporation system as claimed in claim 3 wherein the two or more electrodes of the electroporation probe comprise at least one pair of contiguous electrodes, each electrode having a length of 1 mm or less.

5. The electroporation system as claimed in claim 1, further comprising a controller configured to allow selective control of the pulse generator to control a sequence of pulses delivered via the electroporation probe.

6. The electroporation system as claimed in claim 5 wherein the controller is further configured to allow selection of electrodes to be driven from the at least two electrodes.

7. The electroporation system as claimed in claim 5 wherein the controller is further configured to control electrical pulse parameters for the sequence of pulses based on carrier solution characteristics.

8. The electroporation system as claimed in claim 7 wherein the controller is configured to calculate the electrical pulse parameters based on a target electric potential gradient in the induced non-uniform electric field.

9. The electroporation system as claimed in claim 7 wherein the controller is configured to measure one or more operating characteristics for the biological tissue into which the electroporation probe is inserted.

10. The electroporation system as claimed in claim 9 wherein the controller is further configured to predict induced field voltage during pulse delivery based on the measured one or more operating characteristics, and to determine electrical pulse parameters for pulse delivery based on the measured one or more operating characteristics.

11. The electroporation system as claimed in claim 9 wherein the controller is configured to trigger electrical pulse delivery based on the measured one or more operating characteristics.

12. The electroporation system as claimed in claim 1 wherein the electroporation probe further comprises at least one therapeutic agent delivery structure.

13. The electroporation system as claimed in claim 12, further comprising a therapeutic delivery controller configured to control delivery of the therapeutic agent to the biological tissue.

14. The electroporation probe comprising a linear array of at least two contiguous electrodes, with each electrode formed in a longitudinal section along the electroporation probe, the electroporation probe being configured to be temporarily inserted into a biological tissue for electroporation treatment and connectable to a pulse generator, the electrodes configured to induce a non-uniform electric field in the biological tissue proximate the probe electrodes when driven as one or more anodes and one or more cathodes so as to have different anode and cathode regions spaced along the electroporation probe using a pulse sequence of one or more electric pulses causing current transmission through the probe, the physical electrode array geometry in combination with the pulse sequence causing generation of a shaped non-uniform electric field having electric field gradients in a target region in the biological tissue proximate the probe electrodes, where for each anode and cathode region, a gap between the anode and cathode focuses electric fields generated by passing current between the anode and cathode such that the electric field induced in the biological tissue is of highest electric field strength orthogonal to the point between the anode and cathode, whereby the electrode array geometry controls non-uniformity by causing variation in electric field strength along the array to spatially target a treatment area in the biological tissue.

15. The electroporation probe as claimed in claim 14, each electrode having a length of 1 mm or less and an electrode circumference less than the electrode length.

16. The electroporation probe as claimed in claim 14, wherein the probe comprises at least one fluid delivery structure for delivery of any one or more therapeutic agents, carrier solutions or other chemicals.

17. An electroporation system controller comprising a system processor and memory, the controller being configured to determine a pulse sequence of one or more electric pulses and electrical pulse parameters for the pulse sequence to, when applied to an electroporation probe comprising a linear array of at least two contiguous electrodes with each electrode formed in a longitudinal section along the electroporation probe with a gap between each electrode, drive the at least two electrodes of the electroporation probe as one or more anodes and one or more cathodes so as to have different anode and cathode regions spaced along the electroporation probe, the physical electrode array geometry in combination with the pulse sequence causing generation of a shaped non-uniform electric field having electric field gradients in a target region in a biological tissue proximate the probe electrodes for an electroporation treatment, where for each anode and cathode region, a gap between the anode and cathode focuses electric fields generated by passing current between the anode and cathode such that the electric field induced in the biological tissue is of highest electric field strength orthogonal to the point between the anode and cathode, whereby the electrode array geometry controls non-uniformity by causing variation in electric field strength along the array to spatially target a treatment area in the biological tissue.

18. The electroporation system controller as claimed in claim 17 wherein the electrical pulse parameters for the sequence of pulses are determined based on carrier solution characteristics and wherein the controller is configured to calculate the electrical pulse parameters based on a target electric potential gradient for the induced non-uniform electric field.

19. The electroporation system controller as claimed in claim 17 further configured to measure one or more operating characteristics for the biological tissue into which a connected electroporation probe is inserted, predict induced field voltage during pulse delivery based on the measured operating characteristics, and determine electrical pulse parameters for pulse delivery based on the measured operating characteristics.

20. The electroporation system controller as claimed in claim 17 further configured to model electroporation treatment outcomes for one or more sequences of pulses and electrical pulse parameters based on electroporation probe configuration, target treatment area and carrier solution.

* * * * *